(12) United States Patent
Brown

(10) Patent No.: US 7,442,704 B2
(45) Date of Patent: Oct. 28, 2008

(54) AMIDE DERIVATIVES

(75) Inventor: Dearg S Brown, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 11/176,327

(22) Filed: Jul. 8, 2005

(65) Prior Publication Data

US 2005/0245551 A1    Nov. 3, 2005

Related U.S. Application Data

(62) Division of application No. 09/936,758, filed as application No. PCT/GB00/00912 on Mar. 13, 2000, now Pat. No. 7,008,945.

(30) Foreign Application Priority Data

Mar. 17, 1999 (GB) .................................. 9906279.6
Nov. 11, 1999 (GB) .................................. 9926667.8

(51) Int. Cl.
A61K 31/517 (2006.01)
C07D 239/78 (2006.01)

(52) U.S. Cl. .................................. 514/266.31; 544/287

(58) Field of Classification Search ............ 514/266.31; 544/287

See application file for complete search history.

(56) References Cited

U.S. PATENT DOCUMENTS

| | | | |
|---|---|---|---|
| 1,903,899 A | 4/1933 | Laska et al. | |
| 1,909,960 A | 5/1933 | Hitch | |
| 3,211,555 A | 10/1965 | Mory et al. | |
| 3,755,332 A | 8/1973 | Wasley et al. | |
| 4,367,328 A | 1/1983 | Bertram et al. | |
| 4,524,168 A | 6/1985 | Wick | |
| 4,749,729 A | 6/1988 | Kohli et al. | |
| 5,710,158 A | 1/1998 | Myers et al. | |
| 6,127,374 A | 10/2000 | Bridges | |
| 6,432,949 B1 | 8/2002 | Brown et al. | |
| 6,455,520 B1 | 9/2002 | Brown et al. | |
| 6,465,455 B1 | 10/2002 | Brown et al. | |
| 6,498,274 B1 | 12/2002 | Brown et al. | |
| 6,548,514 B1 | 4/2003 | Brown | |
| 6,579,872 B1 | 6/2003 | Brown et al. | |
| 6,593,333 B1 | 7/2003 | Cumming | |
| 6,686,467 B2 | 2/2004 | Brown et al. | |
| 6,716,847 B2 | 4/2004 | Cumming | |
| 6,784,174 B1 * | 8/2004 | Cumming ................. | 514/234.2 |
| 6,794,380 B2 | 9/2004 | Brown | |
| 6,821,965 B1 | 11/2004 | Brown et al. | |
| 6,846,827 B1 | 1/2005 | Cumming | |
| 6,956,037 B2 | 10/2005 | Brown et al. | |
| 7,008,945 B1 | 3/2006 | Brown | |
| 7,060,700 B2 | 6/2006 | Brown et al. | |

FOREIGN PATENT DOCUMENTS

| | | |
|---|---|---|
| DE | 522 788 | 3/1931 |
| DE | 28 12 252 | 10/1979 |
| EP | 0 566 226 | 10/1993 |
| EP | 0 635 507 | 1/1995 |
| EP | 0 849 256 A1 | 6/1998 |
| EP | 0 945 443 | 9/1999 |
| JP | 61-204221 | 9/1986 |
| WO | 93/04170 | 3/1993 |
| WO | 95/19774 | 7/1995 |
| WO | 95/35304 | 12/1995 |
| WO | 97/05878 | 2/1997 |
| WO | 97/13771 | 4/1997 |
| WO | 97/32853 | 9/1997 |
| WO | 97/33883 | 9/1997 |
| WO | 98/06715 | 2/1998 |
| WO | 98/22103 | 5/1998 |
| WO | 99/01439 | 1/1999 |
| WO | 99/15164 | 4/1999 |
| WO | 99/59959 | 11/1999 |
| WO | 99/59960 | 11/1999 |
| WO | WO 99/59959 | 11/1999 |
| WO | 00/07980 | 2/2000 |
| WO | 00/07991 | 2/2000 |

(Continued)

OTHER PUBLICATIONS

U.S. Appl. No. 10/424,127, filed Apr. 28, 2003, Brown et al.

(Continued)

Primary Examiner—Kamal A Saeed
(74) Attorney, Agent, or Firm—Morgan, Lewis & Bockius LLP

(57) ABSTRACT

The invention concerns amide derivatives of Formula (Ia) wherein X is —NHCO— or —CONH—; m is 0-3; $R^1$ is a group such as hydroxy, halogeno, trifluoromethyl, cyano, mercapto, nitro, amino, carboxy and carbamoyl; n is 0-2; $R^2$ is a group such as hydroxy, halogeno, trifluoromethyl, cyano, mercapto, nitro, amino and carboxy; $R^3$ is hydrogen, halogeno, (1-6C)alkyl or (1-6C)alkoxy; q is 0-4; and Q is a group such as aryl, aryloxy, aryl-(1-6C)alkoxy, arylamino and N-(1-6C)alkyl-arylamino; or pharmaceutically-acceptable salts or in-vivo-cleavable esters thereof; processes for their preparation, pharmaceutical compositions containing them and their use in the treatment of diseases or medical conditions mediated by cytokines.

(Ia)

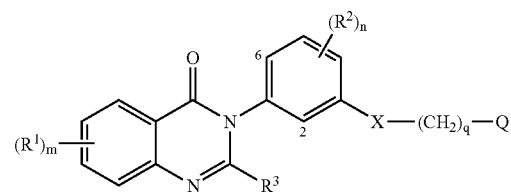

12 Claims, No Drawings

FOREIGN PATENT DOCUMENTS

| WO | 00/12485 | 3/2000 |
|---|---|---|
| WO | 00/12486 | 3/2000 |
| WO | 00/12487 | 3/2000 |
| WO | 00/18738 | 4/2000 |
| WO | 00/20402 | 4/2000 |
| WO | 00/55120 | 9/2000 |
| WO | 00/56738 | 9/2000 |
| WO | WO 00/55153 | 9/2000 |
| WO | 01/27089 | 4/2001 |
| WO | WO 02/083143 | 10/2002 |
| WO | WO 03/066603 | 8/2003 |
| WO | WO 2005/042502 | 5/2005 |

OTHER PUBLICATIONS

U.S. Appl. No. 10/947,463, filed Sep. 23, 2004, Brown et al.
U.S. Appl. No. 10/192,495, filed Jul. 11, 2002, Brown et al.
U.S. Appl. No. 11/125,321, filed May 10, 2005, Brown et al.
U.S. Appl. No. 09/936,758, filed Sep. 17, 2001, Brown.
Barakat et al. "Synthesis and Hypnotic Activity of Some New Quinazolinone Derivatives" Saudi Pharmaceutical Journal 3(3): 84-89 (1995).
Adams et al., "Search for trypanocides. III. Analogs of suramin.", Chemical Abstracts, vol. 51, 1957, columns 5068 and 5069.
Ando et al., "Producing azo lake pigments"; Chemical Abstract, vol. 106, Abstract No. 215574.
Ando et al., "Substitutent Shielding Parameters of Ffluorine-19 NMR on Polyfluoroaromatic Compounds Dissolved in Dimethyl Sulfoxide-$d_6$", Magn. Reson.Chem. 639-45, 1995, Chemical Abstract: 123: 227514, 1995.
Ashton et al., "New Low-Density Lipoprotein Receptor Upregulators Acting via a Novel Mechanism", J. Med. Chem., 1996, vol. 39, pp. 3343-3356.
Beilstein Reg. No. 2164595.
Beilstein Reg. No. 3166971.
Beilstein Reg. No. 3451759.
Beilstein Reg. No. 3480574.
Beilstein Reg. No. 3483669.
Beilstein Reg. No. 3534091.
Chemical Abstract No. 12076g, vol. 65, 1966.
Chemical Abstract No. 12932a, vol. 51, 1957.
Denny et al. "Potential Antitumor Agents. 29. Quantitative Structure-Activity Relationships for the Antileukemic Bisquaternary Ammonium Heterocycles", Journal of Medicinal Chemistry, Feb. 1979, vol. 22, No. 2, pp. 134-150.
Hamuro et al., "Novel Folding Patterns in a Family of Oligoanthranilamides . . . Secondary Structures", J. Amer. Chem. Soc., 1997, pp. 10587-10593.
Ito et al., Photosensitive material containing microencapsulated hydrazine derivatives; Chemical Abstract, vol. 118, Abstract No. 70021.
Kelley et al., "Antirhinovirus Activity of 6-Anilino-9-benxyl-2-chloro-9$H$-purines", J. Med. Chem., 1990, vol. 33, pp. 1360-1363, XP-002140324.
Kuboto et al.; Abstract No. 84:45269, Japan 50105558, Aug. 1975.
Lesiak, "New amides of pyrrole-N- and indole-N-caboxylic acids", Chemical Abstracts, No. 126704v, XP-002121335.
Makoto; "Amide and Its Use"; Patent Abstracts of Japan, Abstract No. 09124571, May 13, 1997, also attached: Abstract (Derwent); XP 002086154.
Mühlbach, "Pyrazoles—A Novel Class of Blocking Agents for Isocyanates", Journal of Polymer Science: Part A: Polymer Chemistry, vol. 32, Mar. 1994, pp. 753-765.
Myers et al., "The Preparation of SAR of 4-(Anilino), 4-(Phenoxy), and 4- (Thiophenoxy)-Quinazoline: Inhibitors of P56$^{lck}$ and EGF-R Tyrosine Kinase Activity", Bioorganic & Medicinal Chemistry Letters, vol. 7, No. 4, pp. 417-420.
Petrova et al., "Determination of the Structure of the Oxidative . . . by Spectroscopic Methods", Journal of Molecular Structure, vol. 142, 1986, pp. 459-462.
Sugawara et al., Kogyo Kaguku Zasshi 72(11) 2425-2429, 1969, Chemical Abstract: 72:66514, 1970.
Thompson et al., "Tyrosine Kinase Inhibitors. 7.7-Amino-4-(phenylamino- and 7-Amino-4-[(phenylmethyl)amino]purido[4,3-$d$[pyrimidines: A New Class of Inhibitors of the Tyrosine Kinase Activity of the Epidermal Growth Factor Receptor"; Journal of Medicinal Chemistry, US, American Chemical Society, vol. 39, No. 19, 1995, pp. 3780-3788, XP002140323.
Wang et al., "Low-valent Titanium-induced Reactions of Substituted Nitrobenzenes", J. Chem. Research, 1998, pp. 182-183.
Chemical Abstracts, vol. 77, No. 3, Jul. 17, 1972, Abstract No. 019599, Kozhevnikov, "Syntheiss of nitro and amino derivatives of 2-methyl-3-aryl-4-quinazolone", XP002139275 cited in the application abstract & Izv. Vyssh. Ucheb. Zaved., Khim. Khim. Tekhnol. (IVUKAR): 1971; vol. 14 (11), pp. 1685-1689, Perm. Farm. Inst.; Perm; USSR.
Chemical Abstracts, vol. 069, No. 15, Oct. 7, 1968, Abstract No. 059182, Parmar, S., et al., "Synthesis of substituted quinazoline hydrazides: the relation between chemical structure and monoamine oxidase inhibitor activity", XP002138276, Abstract & Can. J. Chem. (CJCHAG); 1968; vol. 46 (15), pp. 2519-2524, Lucknow Univ.; King George's Med. Coll.; Lucknow; India.

* cited by examiner

AMIDE DERIVATIVES

This Application is a Divisional of U.S. application Ser. No. 09/936,758, filed Nov. 15, 2001, now U.S. Pat. No. 7,008, 945, which is a PCT National Stage of PCT/GB00/00912 filed Mar. 13, 2000, which claims priority to Great Britain Application Nos. 9906279.6 filed Mar. 17, 1999 and 9926667.8 filed Nov. 11, 1999.

This invention concerns certain amide derivatives which are useful as inhibitors of cytokine mediated disease. The invention also concerns processes for the manufacture of the amide derivatives of the invention, pharmaceutical compositions containing them and their use in therapeutic methods, for example by virtue of inhibition of cytokine mediated disease.

The amide derivatives disclosed in the present invention are inhibitors of the production of cytokines such as Tumour Necrosis Factor (hereinafter TNF), for example TNFα, and various members of the interleukin (hereinafter IL) family, for example IL-1, IL-6 and IL-8. Accordingly the compounds of the invention will be useful in the treatment of diseases or medical conditions in which excessive production of cytokines occurs, for example excessive production of TNFα or IL-1. It is known that cytokines are produced by a wide variety of cells such as monocytes and macrophages and that they give rise to a variety of physiological effects which are believed to be important in disease or medical conditions such as inflammation and immunoregulation. For example, TNFα and IL-1 have been implicated in the cell signalling cascade which is believed to contribute to the pathology of disease states such as inflammatory and allergic diseases and cytokine-induced toxicity. It is also known that, in certain cellular systems, TNFα production precedes and mediates the production of other cytokines such as IL-1.

Abnormal levels of cytokines have also been implicated in, for example, the production of physiologically-active eicosanoids such as the prostaglandins and leukotrienes, the stimulation of the release of proteolytic enzymes such as collagenase, the activation of the immune system, for example by stimulation of T-helper cells, the activation of osteoclast activity leading to the resorption of calcium, the stimulation of the release of proteoglycans from, for example, cartilage, the stimulation of cell proliferation and to angiogenesis.

Cytokines are also believed to be implicated in the production and development of disease states such as inflammatory and allergic diseases, for example inflammation of the joints (especially rheumatoid arthritis, osteoarthritis and gout), inflammation of the gastrointestinal tract (especially inflammatory bowel disease, ulcerative colitis, Crohn's disease and gastritis), skin disease (especially psoriasis, eczema and dermatitis) and respiratory disease (especially asthma, bronchitis, allergic rhinitis, adult respiratory distress syndrome and chronic obstructive pulmonary disease), and in the production and development of various cardiovascular and cerebrovascular disorders such as congestive heart failure, myocardial infarction, the formation of atherosclerotic plaques, hypertension, platelet aggregation, angina, stroke, Alzheimer's disease, reperfusion injury, vascular injury including restenosis and peripheral vascular disease, and, for example, various disorders of bone metabolism such as osteoporosis (including senile and postmenopausal osteoporosis), Paget's disease, bone metastases, hypercalcaemia, hyperparathyroidism, osteosclerosis, osteoperosis and periodontitis, and the abnormal changes in bone metabolism which may accompany rheumatoid arthritis and osteoarthritis. Excessive cytokine production has also been implicated in mediating certain complications of bacterial, fungal and/or viral infections such as endotoxic shock, septic shock and toxic shock syndrome and in mediating certain complications of CNS surgery or injury such as neurotrauma and ischaemic stroke. Excessive cytokine production has also been implicated in mediating or exacerbating the development of diseases involving cartilage or muscle resorption, pulmonary fibrosis, cirrhosis, renal fibrosis, the cachexia found in certain chronic diseases such as malignant disease and acquired immune deficiency syndrome (AIDS), tumour invasiveness and tumour metastasis and multiple sclerosis.

Evidence of the central role played by TNFα in the cell signalling cascade which gives rise to rheumatoid arthritis is provided by the efficacy in clinical studies of antibodies of TNFα (*The Lancet*, 1994, 344, 1125 and *British Journal of Rheumatology*, 1995, 34, 334).

Thus cytokines such as TNFα and IL-1 are believed to be important mediators of a considerable range of diseases and medical conditions. Accordingly it is expected that inhibition of the production of and/or effects of these cytokines will be of benefit in the prophylaxis, control or treatment of such diseases and medical conditions.

Without wishing to imply that the compounds disclosed in the present invention possess pharmacological activity only by virtue of an effect on a single biological process, it is believed that the compounds inhibit the effects of cytokines by virtue of inhibition of the enzyme p38 kinase. p38 kinase, otherwise known as cytokine suppressive binding protein (hereinafter CSBP) and reactivating kinase (hereinafter RK), is a member of the mitogen-activated protein (hereinafter MAP) kinase family of enzymes which is known to be activated by physiological stress such as that induced by ionising radiation, cytotoxic agents, and toxins, for example endotoxins such as bacterial lipopolysaccharide, and by a variety of agents such as the cytokines, for example TNFα and IL-1. It is known that p38 kinase phosphorylates certain intracellular proteins which are involved in the cascade of enzymatic steps which leads to the biosynthesis and excretion of cytokines such as TNFα and IL-1. Known inhibitors of p38 kinase have been reviewed by G J Hanson in *Expert Opinions on Therapeutic Patents*, 1997, 7, 729-733. p38 kinase is known to exist in isoforms identified as p38α and p38β.

The compounds disclosed in the present invention are inhibitors of the production of cytokines such as TNF, in particular of TNFα, and various interleukins, in particular IL-1.

Certain 3-(5-benzamido-2-methylphenyl)-3,4-dihydroquinazolin-4-one derivatives were disclosed in Chemical Abstracts, volume 77, abstract 19599. The disclosed compounds included: -3-(5-benzamido-2-methylphenyl)-2-methyl-3,4-dihydroquinazolin-4-one, 3-[5-(4-methylbenzamido)-2-methylphenyl]-2-methyl-3,4-dihydroquinazolin-4-one and 3-[5-(4-methoxybenzamido)-2-methylphenyl]-2-methyl-3,4-dihydroquinazolin-4-one.

According to one aspect of the present invention there is provided a compound of the Formula Ia

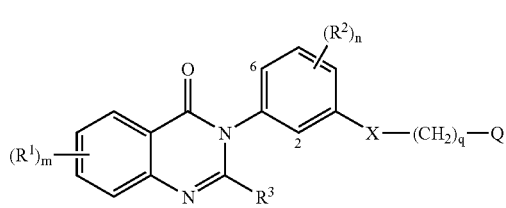

Ia wherein X is —NHCO— or —CONH—;
m is 0, 1, 2 or 3;
R¹ is hydroxy, halogeno, trifluoromethyl, cyano, mercapto, nitro, amino, carboxy, carbamoyl, formyl, (1-6C)alkyl, (2-6C)alkenyl, (2-6C)alkynyl, (1-6C)alkoxy, (1-6C)alkylthio, (1-6C)alkylsulphinyl, (1-6C)alkylsulphonyl, (1-6C)

alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (1-6C)alkanoylamino, N-(1-6C)alkyl-(1-6C)alkanoylamino, N-(1-6C)alkylsulphamoyl, N,N-di-[(1-6C)alkyl]sulphamoyl, (1-6C)alkanesulphonylamino, N-(1-6C)alkyl-(1-6C)alkanesulphonylamino, halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, carboxy-(1-6C)alkyl, (1-6C)alkoxycarbonyl-(1-6C)alkyl, carbamoyl-(1-6C)alkyl, N-(1-6C)alkylcarbamoyl-(1-6C)alkyl, N,N-di-[(1-6C)alkyl]carbamoyl-(1-6C)alkyl, halogeno-(2-6C)alkoxy, hydroxy-(2-6C)alkoxy, (1-6C)alkoxy-(2-6C)alkoxy, cyano-(1-6C)alkoxy, carboxy-(1-6C)alkoxy, (1-6C)alkoxycarbonyl-(1-6C)alkoxy, carbamoyl-(1-6C)alkoxy, N-(1-6C)alkylcarbamoyl-(1-6C)alkoxy, N,N-di-[(1-6C)alkyl]carbamoyl-(1-6C)alkoxy, amino-(2-6C)alkoxy, (1-6C)alkylamino-(2-6C)alkoxy, di-[(1-6C)alkyl]amino-(2-6C)alkoxy, halogeno-(2-6C)alkylamino, hydroxy-(2-6C)alkylamino, (1-6C)alkoxy-(2-6C)alkylamino, cyano-(1-6C)alkylamino, carboxy-(1-6C)alkylamino, (1-6C)alkoxycarbonyl-(1-6C)alkylamino, carbamoyl-(1-6C)alkylamino, N-(1-6C)alkylcarbamoyl-(1-6C)alkylamino, N,N-di-[(1-6C)alkyl]carbamoyl-(1-6C)alkylamino, amino-(2-6C)alkylamino, (1-6C)alkylamino-(2-6C)alkylamino, di-[(1-6C)alkyl]amino-(2-6C)alkylamino, N-(1-6C)alkyl-halogeno-(1-6C)alkylamino, N-(1-6C)alkyl-hydroxy-(2-6C)alkylamino, N-(1-6C)alkyl-(1-6C)alkoxy-(2-6C)alkylamino; N-(1-6C)alkyl-cyano-(1-6C)alkylamino, N-(1-6C)alkyl-carboxy-(1-6C)alkylamino, N-(1-6C)alkyl-(1-6C)alkoxycarbonyl-(1-6C)alkylamino, N-(1-6C)alkyl-carbamoyl-(1-6C)alkylamino, N-(1-6C)alkyl-N-(1-6C)alkylcarbamoyl-(1-6C)alkylamino, N-(1-6C)alkyl-N,N-di-[(1-6C)alkyl]carbamoyl-(1-6C)alkylamino, N-(1-6C)alkyl-amino-(2-6C)alkylamino, N-(1-6C)alkyl-(1-6C)alkylamino-(2-6C)alkylamino, N-(1-6C)alkyl-di-[(1-6C)alkyl]amino-(2-6C)alkylamino, halogeno-(2-6C)alkanoylamino, hydroxy-(2-6C)alkanoylamino, (1-6C)alkoxy-(2-6C)alkanoylamino, cyano-(2-6C)alkanoylamino, carboxy-(2-6C)alkanoylamino, (1-6C)alkoxycarbonyl-(2-6C)alkanoylamino, carbamoyl-(2-6C)alkanoylamino, N-(1-6C)alkylcarbamoyl-(2-6C)alkanoylamino, N,N-di-[(1-6C)alkyl]carbamoyl-(2-6C)alkanoylamino, amino-(2-6C)alkanoylamino, (1-6C)alkylamino-(2-6C)alkanoylamino
or di-[(1-6C)alkyl]amino-(2-6C)alkanoylamino, or $R^1$ is aryl, aryl-(1-6C)alkyl, aryl-(1-6C)alkoxy, aryloxy, arylamino, N-(1-6C)alkyl-arylamino, aryl-(1-6C)alkylamino, N-(1-6C)alkyl-aryl-(1-6C)alkylamino, aroylamino, arylsulphonylamino, N-arylsulphamoyl, aryl-(2-6C)alkanoylamino, heteroaryl, heteroaryl-(1-6C)alkyl, heteroaryloxy, heteroaryl-(1-6C)alkoxy, heteroarylamino, N-(1-6C)alkyl-heteroarylamino, heteroaryl-(1-6C)alkylamino, N-(1-6C)alkyl-heteroaryl-(1-6C)alkylamino, heteroarylcarbonylamino, heteroarylsulphonylamino, N-heteroarylsulphamoyl, heteroaryl-(2-6C)alkanoylamino, heteroaryl-(1-6C)alkoxy-(1-6C)alkyl, heteroaryl-(1-6C)alkylamino-(1-6C)alkyl, N-(1-6C)alkyl-heteroaryl-(1-6C)alkylamino-(1-6C)alkyl, heterocyclyl, heterocyclyl-(1-6C)alkyl, heterocyclyloxy, heterocyclyl-(1-6C)alkoxy, heterocyclylamino, N-(1-6C)alkyl-heterocyclylamino, heterocyclyl-(1-6C)alkylamino, N-(1-6C)alkyl-heterocyclyl-(1-6C)alkylamino, heterocyclylcarbonylamino, heterocyclylsulphonylamino, N-heterocyclylsulphamoyl, heterocyclyl-(2-6C)alkanoylamino, heterocyclyl-(1-6C)alkoxy-(1-6C)alkyl, heterocyclyl-(1-6C)alkylamino-(1-6C)alkyl or N-(1-6C)alkyl-heterocyclyl-(1-6C)alkylamino-(1-6C)alkyl, or $(R^1)_m$ is a (1-3C)alkylenedioxy group, and wherein any of the $R^1$ substituents defined hereinbefore which comprises a $CH_2$ group which is attached to 2 carbon atoms or a $CH_3$ group which is attached to a carbon atom may optionally bear on each said $CH_2$ or $CH_3$ group a substituent selected from hydroxy, amino, (1-6C)alkoxy, (1-6C)alkylamino, di-[(1-6C)alkyl]amino and heterocyclyl, and wherein any aryl, heteroaryl or heterocyclyl group in a $R^1$ substituent may optionally bear 1 or 2 substituents selected from hydroxy, halogeno, (1-6C)alkyl, (1-6C)alkoxy, carboxy, (1-6C)alkoxycarbonyl, N-(1-6C)alkylcarbamoyl, N,N-di-[(1-6C)alkyl]carbamoyl, (2-6C)alkanoyl, amino, (1-6C)alkylamino, di-[(1-6C)alkyl]amino, halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, aryl and aryl-(1-6C)alkyl, and wherein any heterocyclyl group in a $R^1$ substituent may optionally bear 1 or 2 oxo or thioxo substituents;

n is 0, 1 or 2;

$R^2$ is hydroxy, halogeno, trifluoromethyl, cyano, mercapto, nitro, amino, carboxy, (1-6C)alkoxycarbonyl, (1-6C)alkyl, (2-6C)alkenyl, (2-6C)alkynyl, (1-6C)alkoxy, (1-6C)alkylamino or di-[(1-6C)alkyl]amino;

$R^3$ is hydrogen, halogeno, (1-6C)alkyl or (1-6C)alkoxy;

q is 0, 1, 2, 3 or 4; and

Q is aryl, aryloxy, aryl-(1-6C)alkoxy, arylamino, N-(1-6C)alkyl-arylamino, aryl-(1-6C)alkylamino, N-(1-6C)alkyl-aryl-(1-6C)alkylamino, aroylamino, arylsulphonylamino, N-arylcarbamoyl, N-arylsulphamoyl, aryl-(2-6C)alkanoylamino, (3-7C)cycloalkyl, heteroaryl, heteroaryloxy, heteroaryl-(1-6C)alkoxy, heteroarylamino, N-(1-6C)alkyl-heteroarylamino, heteroaryl-(1-6C)alkylamino, N-(1-6C)alkyl-heteroaryl-(1-6C)alkylamino, heteroarylcarbonylamino, heteroarylsulphonylamino, N-heteroarylcarbamoyl, N-heteroarylsulphamoyl, heteroaryl-(2-6C)alkanoylamino, heterocyclyl, heterocyclyloxy, heterocyclyl-(1-6C)alkoxy, heterocyclylamino, N-(1-6C)alkyl-heterocyclylamino, heterocyclyl-(1-6C)alkylamino, N-(1-6C)alkyl-heterocyclyl-(1-6C)alkylamino, heterocyclylcarbonylamino, heterocyclylsulphonylamino, N-heterocyclylcarbamoyl, N-heterocyclylsulphamoyl or heterocyclyl-(2-6C)alkanoylamino, and Q is optionally substituted with 1, 2 or 3 substituents selected from hydroxy, halogeno, trifluoromethyl, cyano, mercapto, nitro, amino, carboxy, carbamoyl, formyl, (1-6C)alkyl, (2-6C)alkenyl, (2-6C)alkynyl, (1-6C)alkoxy, (1-6C)alkylthio, (1-6C)alkylsulphinyl (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (1-6C)alkanoylamino, N-(1-6C)alkyl-(1-6C)alkanoylamino, N-(1-6C)alkylsulphamoyl, N,N-di-[(1-6C)alkyl]sulphamoyl, (1-6C)alkanesulphonylamino, N-(1-6C)alkyl-(1-6C)alkanesulphonylamino, halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, carboxy-(1-6C)alkyl, (1-6C)alkoxycarbonyl-(1-6C)alkyl, carbamoyl-(1-6C)alkyl, N-(1-6C)alkylcarbamoyl-(1-6C)alkyl, N,N-di-[(1-6C)alkyl]carbamoyl-(1-6C)alkyl, halogeno-(2-6C)alkoxy, hydroxy-(2-6C)alkoxy, (1-6C)alkoxy-(2-6C)alkoxy, cyano-(1-6C)alkoxy, carboxy-(1-6C)alkoxy, (1-6C)alkoxycarbonyl-(1-6C)alkoxy, carbamoyl-(1-6C)alkoxy, N-(1-6C)alkylcarbamoyl-(1-6C)alkoxy, N,N-di-[(1-6C)alkyl]carbamoyl-(1-6C)alkoxy, amino-(2-6C)alkoxy, (1-6C)alkylamino-(2-6C)alkoxy, di-[(1-6C)alkyl]amino-(2-6C)alkoxy, halogeno-(2-6C)alkylamino, hydroxy-(2-6C)alkylamino, (1-6C)alkoxy-(2-6C)alkylamino, cyano-(1-6C)alkylamino, carboxy-(1-6C)alkylamino, (1-6C)alkoxycarbonyl-(1-6C)alkylamino, carbamoyl-(1-6C)alkylamino, N-(1-6C)alkylcarbamoyl-(1-6C)alkylamino, N,N-di-[(1-6C)alkyl]carbamoyl-(1-6C)alkylamino, amino-(2-6C)alkylamino, (1-6C)alkylamino-(2-6C)alkylamino, di-[(1-6C)alkyl]amino-(2-6C)alkylamino, N-(1-6C)alkyl-halogeno-(1-6C)alkylamino, N-(1-6C)alkyl-hydroxy-(2-6C)alkylamino, N-(1-6C)alkyl-(1-6C)alkoxy-(2-6C)alkylamino, N-(1-6C)alkyl-cyano-(1-6C)alkylamino, N-(1-6C)alkyl-carboxy-(1-6C)alkylamino, N-(1-6C)alkyl-(1-6C)alkoxycarbonyl-(1-6C)alkylamino, N-(1-6C)alkyl-carbamoyl-(1-6C)alkylamino, N-(1-6C)alkyl-N-(1-6C)alkylcarbamoyl-(1-6C)alkylamino, N-(1-6C)alkyl-N,N-di-[(1-6C)alkyl]carbamoyl-(1-6C)alkylamino, N-(1-6C)alkyl-amino-(2-6C)alkylamino, N-(1-6C)alkyl-(1-6C)alkylamino-(2-6C)alkylamino, N-(1-6C)alkyl-di-[(1-6C)alkyl]amino-(2-6C)alkylamino, halogeno-(2-6C)alkanoylamino, hydroxy-(2-6C)alkanoylamino, (1-6C)alkoxy-(2-6C)alkanoylamino, cyano-(2-6C)alkanoylamino, carboxy-(2-6C)alkanoylamino, (1-6C)alkoxycarbonyl-(2-6C)alkanoylamino, carbamoyl-(2-6C)alkanoylamino, N-(1-6C)alkylcarbamoyl-(2-6C)alkanoylamino, N,N-di-[(1-6C)alkyl]carbamoyl-(2-6C)alkanoylamino, amino-(2-6C)alkanoylamino, (1-6C)alkylamino-(2-6C)alkanoylamino, di-[(1-6C)alkyl]amino-(2-6C)alkanoylamino, aryl, aryl-(1-6C)alkyl, aryl-(1-6C)alkoxy, aryloxy, arylamino, N-(1-6C)alkyl-arylamino, aryl-(1-6C)alkylamino, N-(1-6C)alkyl-aryl-(1-6C)alkylamino, aroylamino, arylsulphonylamino, N-arylsulphamoyl, aryl-(2-6C)alkanoylamino, heteroaryl, heteroaryl-(1-6C)alkyl, heteroaryloxy, heteroaryl-(1-6C)alkoxy, heteroarylamino, N-(1-6C)alkyl-heteroarylamino, heteroaryl-(1-6C)alkylamino, N-(1-6C)alkyl-heteroaryl-(1-6C)alkylamino, heteroarylcarbonylamino, heteroarylsulphonylamino, N-heteroarylsulphamoyl, heteroaryl-(2-6C)alkanoylamino, heteroaryl-(1-6C)alkoxy-(1-6C)alkyl, heteroaryl-(1-6C)alkylamino-(1-6C)alkyl, N-(1-6C)alkyl-heteroaryl-(1-6C)alkylamino-(1-6C)alkyl, heterocyclyl, heterocyclyl-(1-6C)alkyl, heterocyclyloxy, heterocyclyl-(1-6C)alkoxy, heterocyclylamino, N-(1-6C)alkyl-heterocyclylamino, heterocyclyl-(1-6C)alkylamino, N-(1-6C)alkyl-heterocyclyl-(1-6C)alkylamino, heterocyclylcarbonylamino, heterocyclylsulphonylamino, N-heterocyclylsulphamoyl, heterocyclyl-(2-6C)alkanoylamino, heterocyclyl-(1-6C)alkoxy-(1-6C)alkyl, heterocyclyl-(1-6C)alkylamino-(1-6C)alkyl and N-(1-6C)alkyl-heterocyclyl-(1-6C)alkylamino-(1-6C)alkyl, or Q is substituted with a (1-3C)alkylenedioxy group, and wherein any of the substituents on Q defined hereinbefore which comprises a $CH_2$ group which is attached to 2 carbon atoms or a $CH_3$ group which is attached to a carbon atom may optionally bear on each said $CH_2$ or $CH_3$ group a substituent selected from hydroxy, amino, (1-6C)alkoxy, (1-6C)alkylamino, di-[(1-6C)alkyl]amino and heterocyclyl, and wherein any aryl, heteroaryl or heterocyclyl group in a bear 1 or 2 substituents selected from hydroxy, halogeno, (1-6C)alkyl, (1-6C)alkoxy, carboxy, (1-6C)alkoxycarbonyl, N-(1-6C)alkylcarbamoyl, N,N-di-[(1-6C)alkyl]carbamoyl, (2-6C)alkanoyl, amino, (1-6C)alkylamino, di-[(1-6C)alkyl]amino, halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, aryl and aryl-(1-6C)alkyl, and wherein Q when it is a heterocyclyl group or it contains a heterocyclyl group or any heterocyclyl group in a substituent on Q may optionally bear 1 or 2 oxo or thioxo substituents;

or a pharmaceutically-acceptable salt or in-vivo-cleavable ester thereof;

except that 3-(5-benzamido-2-methylphenyl)-2-methyl-3,4-dihydroquinazolin-4-one, 3-[5-(4-methylbenzamido)-2-methylphenyl]-2-methyl-3,4-dihydroquinazolin-4-one and 3-[5-(4-methoxybenzamido)-2-methylphenyl]-2-methyl-3,4-dihydroquinazolin-4-one are excluded.

According to a further aspect of the present invention there is provided a compound of the Formula Ib

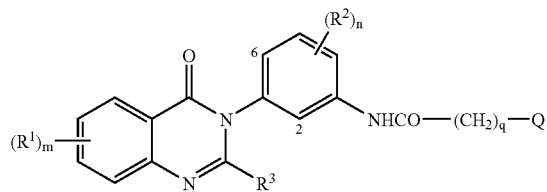

wherein m is 0, 1, 2 or 3;

$R^1$ is hydroxy, halogeno, trifluoromethyl, cyano, mercapto, nitro, amino, carboxy, carbamoyl, formyl, (1-6C)alkyl, (2-6C)alkenyl, (2-6C)alkynyl, (1-6C)alkoxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (1-6C)alkanoylamino, N-(1-6C)alkylsulphamoyl, N,N-di-[(1-6C)alkyl]sulphamoyl, (1-6C)alkanesulphonylamino, N-(1-6C)alkyl-(1-6C)alkanesulphonylamino, halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, carboxy-(1-6C)alkyl, (1-6C)alkoxycarbonyl-(1-6C)alkyl, carbamoyl-(1-6C)alkyl, N-(1-6C)alkylcarbamoyl-(1-6C)alkyl, N,N-di-[(1-6C)alkyl]carbamoyl-(1-6C)alkyl, halogeno-(2-6C)alkoxy, hydroxy-(2-6C)alkoxy, (1-6C)alkoxy-(2-6C)alkoxy, cyano-(1-6C)alkoxy, carboxy-(1-6C)alkoxy, (1-6C)alkoxycarbonyl-(1-6C)alkoxy, carbamoyl-(1-6C)alkoxy, N-(1-6C)alkylcarbamoyl-(1-6C)alkoxy, N,N-di-[(1-6C)alkyl]carbamoyl-(1-6C)alkoxy, amino-(2-6C)alkoxy, (1-6C)alkylamino-(2-6C)alkoxy, di-[(1-6C)alkyl]amino-(2-6C)alkoxy, halogeno-(2-6C)alkylamino, hydroxy-(2-6C)alkylamino, (1-6C)alkoxy-(2-6C)alkylamino, cyano-(1-6C)alkylamino, carboxy-(1-6C)alkylamino, (1-6C)alkoxycarbonyl-(1-6C)alkylamino, carbamoyl-(1-6C)alkylamino, N-(1-6C)alkylcarbamoyl-(1-6C)alkylamino, N,N-di-[(1-6C)alkyl]carbamoyl-(1-6C)alkylamino, amino-(2-6C)alkylamino, (1-6C)alkylamino-(2-6C)alkylamino, di-[(1-6C)alkyl]amino-(2-6C)alkylamino, N-(1-6C)alkyl-halogeno-(1-6C)alkylamino, N-(1-6C)alkyl-hydroxy-(2-6C)alkylamino, N-(1-6C)alkyl-(1-6C)alkoxy-(2-6C)alkylamino, N-(1-6C)alkyl-cyano-(1-6C)alkylamino, N-(1-6C)alkyl-carboxy-(1-6C)alkylamino, N-(1-6C)alkyl-(1-6C)alkoxycarbonyl-(1-6C)alkylamino, N-(1-6C)alkyl-carbamoyl- (1-6C)alkylamino, N-(1-6C)alkylcarbamoyl-(1-6C)alkylamino, N-(1-6C)alkyl-N,N-di-[(1-6C)alkyl]carbamoyl-(1-6C)alkylamino, N-(1-6C)alkyl-amino-(2-6C)alkylamino, N-(1-6C)alkyl-di-[(1-6C)alkyl]amino-(2-6C)alkylamino, halogeno-(2-6C)alkanoylamino, hydroxy-(2-6C)alkanoylamino, (1-6C)alkoxy-(2-6C)alkanoylamino, cyano-(2-6C)alkanoylamino, carboxy-(2-6C)alkanoylamino, (1-6C)alkoxycarbonyl-(2-6C)alkanoylamino, carbamoyl-(2-6C)alkanoylamino, N-(1-6C)alkylcarbamoyl-(2-6C)alkanoylamino, N,N-di-[(1-6C)alkyl]carbamoyl-(2-6C)alkanoylamino, amino-(2-6C)alkanoylamino, (1-6C)alkylamino-(2-6C)alkanoylamino or di-[(1-6C)alkyl]amino-(2-6C)alkanoylamino, or R¹ is aryl, aryl-(1-6C)alkyl, aryl-(1-6C)alkoxy, aryloxy, arylamino, N-(1-6C)alkyl-arylamino, aryl-(1-6C)alkylamino, N-(1-6C)alkyl-aryl-(1-6C)alkylamino, aroylamino, arylsulphonylamino, N-arylsulphamoyl, aryl-(2-6C)alkanoylamino, heteroaryl, heteroaryl-(1-6C)alkyl, heteroaryloxy, heteroaryl-(1-6C)alkoxy, heteroarylamino, N-(1-6C)alkyl-heteroarylamino, heteroaryl-(1-6C)alkylamino, N-(1-6C)alkyl-heteroaryl-(1-6C)alkylamino, heteroarylcarbonylamino, heteroarylsulphonylamino, N-heteroarylsulphamoyl, heteroaryl-(2-6C)alkanoylamino, heteroaryl-(1-6C)alkoxy-(1-6C)alkyl, heteroaryl-(1-6C)alkylamino-(1-6C)alkyl, N-(1-6C)alkyl-heteroaryl-(1-6C)alkylamino-(1-6C)alkyl, heterocyclyl, heterocyclyl-(1-6C)alkyl, heterocyclyloxy, heterocyclyl-(1-6C)alkoxy, heterocyclylamino, N-(1-6C)alkyl-heterocyclylamino, heterocyclyl-(1-6C)alkylamino, N-(1-6C)alkyl-heterocyclyl-(1-6C)alkylamino, heterocyclylcarbonylamino, heterocyclylsulphonylamino, N-heterocyclylsulphamoyl, heterocyclyl-(2-6C)alkanoylamino, heterocyclyl-(1-6C)alkoxy-(1-6C)alkyl, heterocyclyl-(1-6C)alkylamino-(1-6C)alkyl or N-(1-6C)alkyl-heterocyclyl-(1-6C)alkylamino-(1-6C)alkyl, or (R¹)$_m$ is a (1-3C)alkylenedioxy group, and wherein any of the R¹ substituents defined hereinbefore which comprises a CH$_2$ group which is attached to 2 carbon atoms or a CH$_3$ group which is attached to a carbon atom may optionally bear on each said CH$_2$ or CH$_3$ group a substituent selected from hydroxy, amino, (1-6C)alkoxy, (1-6C)alkylamino, di-[(1-6C)alkyl]amino and heterocyclyl, and wherein any aryl, heteroaryl or heterocyclyl group in a R¹ substituent may optionally bear 1 or 2 substituents selected from hydroxy, halogeno, (1-6C)alkyl, (1-6C)alkoxy, carboxy, (1-6C)alkoxycarbonyl, N-(1-6C)alkylcarbamoyl, N,N-di-[(1-6C)alkyl]carbamoyl, (2-6C)alkanoyl, amino, (1-6C)alkylamino, di-[(1-6C)alkyl]amino, halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, aryl and aryl-(1-6C)alkyl, n is 0, 1 or 2;

R² is hydroxy, halogeno, trifluoromethyl, cyano, mercapto, nitro, amino, carboxy, (1-6C)alkoxycarbonyl, (1-6C)alkyl, (2-6C)alkenyl, (2-6C)alkynyl, (1-6C)alkoxy, (1-6C)alkylamino or di-[(1-6C)alkyl]amino;

R³ is hydrogen, halogeno, (1-6C)alkyl or (1-6C)alkoxy;

q is 0, 1, 2, 3 or 4; and

Q is aryl, aryloxy, aryl-(1-6C)alkoxy, arylamino, N-(1-6C)alkyl-arylamino, aryl-(1-6C)alkylamino, N-(1-6C)alkyl-aryl-(1-6C)alkylamino, aroylamino, arylsulphonylamino, N-arylcarbamoyl, N-arylsulphamoyl, aryl-(2-6C)alkanoylamino, (3-7C)cycloalkyl, heteroaryl, heteroaryloxy, heteroaryl-(1-6C)alkoxy, heteroarylamino, N-(1-6C)alkyl-heteroarylamino, heteroaryl-(1-6C)alkylamino, N-(1-6C)alkyl-heteroaryl-(1-6C)alkylamino, heteroarylcarbonylamino, heteroarylsulphonylamino, N-heteroarylcarbamoyl, N-heteroarylsulphamoyl, heteroaryl-(2-6C)alkanoylamino, heterocyclyl, heterocyclyloxy, heterocyclyl-(1-6C)alkoxy, heterocyclylamino, N-(1-6C)alkyl-heterocyclylamino, heterocyclyl-(1-6C)alkylamino, N-(1-6C)alkyl-heterocyclyl-(1-6C)alkylamino, heterocyclylcarbonylamino, heterocyclylsulphonylamino, N-heterocyclylcarbamoyl, N-heterocyclylsulphamoyl or heterocyclyl-(2-6C)alkanoylamino, and Q is optionally substituted with 1, 2 or 3 substituents selected from hydroxy, halogeno, trifluoromethyl, cyano, mercapto, nitro, amino, carboxy, carbamoyl, formyl, (1-6C)alkyl, (2-6C)alkenyl, (2-6C)alkynyl, (1-6C)alkoxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (1-6C)alkanoylamino, N-(1-6C)alkylsulphamoyl, N,N-di-[(1-6C)alkyl]sulphamoyl, (1-6C)alkanesulphonylamino, N-(1-6C)alkyl-(1-6C)alkanesulphonylamino, halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, carboxy-(1-6C)alkyl, (1-6C)alkoxycarbonyl-(1-6C)alkyl, carbamoyl-(1-6C)alkyl, N-(1-6C)alkylcarbamoyl-(1-6C)alkyl, N,N-di-[(1-6C)alkyl]carbamoyl-(1-6C)alkyl, halogeno-(2-6C)alkoxy, hydroxy-(2-6C)alkoxy, (1-6C)alkoxy-(2-6C)alkoxy, cyano-(1-6C)alkoxy, carboxy-(1-6C)alkoxy, (1-6C)alkoxycarbonyl-(1-6C)alkoxy, carbamoyl(1-6C)alkoxy, N-(1-6C)alkylcarbamoyl-(1-6C)alkoxy, N,N-di-[(1-6C)alkyl]carbamoyl-(1-6C)alkoxy, amino-(2-6C)alkoxy, (1-6C)alkylamino-(2-6C)alkoxy, di-[(1-6C)alkyl]amino-(2-6C)alkoxy, halogeno-(2-6C)alkylamino, hydroxy-(2-6C)alkylamino, (1-6C)alkoxy-(2-6C)alkylamino, cyano-(1-6C)alkylamino, carboxy-(1-6C)alkylamino, (1-6C)alkoxycarbonyl-(1-6C)alkylamino, carbamoyl-(1-6C)alkylamino, N-(1-6C)alkylcarbamoyl-(1-6C)alkylamino, N,N-di-[(1-6C)alkyl]carbamoyl-(1-6C)alkylamino, amino-(2-6C)alkylamino, (1-6C)alkylamino-(2-6C)alkylamino, di-[(1-6C)alkyl]amino-(2-6C)alkylamino, N-(1-6C)alkyl-halogeno-(2-6C)alkylamino, N-(1-6C)alkyl-hydroxy-(2-6C)alkylamino, N-(1-6C)alkyl-(1-6C)alkoxy-(2-6C)alkylamino, N-(1-6C)alkyl-cyano-(1-6C)alkylamino, N-(1-6C)alkyl-carboxy-(1-6C)alkylamino, N-(1-6C)alkyl-(1-6C)alkoxycarbonyl-(1-6C)alkylamino, N-(1-6C)alkyl-carbamoyl-(1-6C)alkylamino, N-(1-6C)alkyl-N-(1-6C)alkylcarbamoyl-(1-6C)alkylamino, N-(1-6C)alkyl-N,N-di-[(1-6C)alkyl]carbamoyl-(1-6C)alkylamino, N-(1-6C)alkyl-amino-(2-6C)alkylamino, N-(1-6C)alkyl-(1-6C)alkylamino, (2-6C)alkylamino, N-(1-6C)alkyl-di-[(1-6C)alkyl]amino-(2-6C)alkylamino, halogeno-(2-6C)alkanoylamino, hydroxy-(2-6C)alkanoylamino, (1-6C)alkoxy-(2-6C)alkanoylamino, cyano-(2-6C)alkanoylamino, carboxy-(2-6C)alkanoylamino, (1-6C)alkoxycarbonyl-(2-6C)alkanoylamino, carbamoyl-(2-6C)alkanoylamino, N-(1-6C)alkylcarbamoyl-(2-6C)alkanoylamino, N,N-di-[(1-6C)alkyl]carbamoyl-(2-6C)alkanoylamino, amino-(2-6C)alkanoylamino, (1-6C)alkylamino-(2-6C)alkanoylamino, di-[(1-6C)alkyl]amino-(2-6C)alkanoylamino, aryl, aryl-(1-6C)alkyl, aryl-(1-6C)alkoxy, aryloxy, arylamino, N-(1-6C)alkyl-arylamino, aryl-(1-6C)alkylamino, N-(1-6C)alkyl-aryl-(1-6C)alkylamino, aroylamino, arylsulphonylamino, N-arylsulphamoyl, aryl-(2-6C)alkanoylamino, heteroaryl, heteroaryl-(1-6C)alkyl, heteroaryloxy, heteroaryl-(1-6C)alkoxy, heteroarylamino, N-(1-6C)alkyl-heteroarylamino, heteroaryl-(1-6C)alkylamino, N-(1-6C)alkyl-heteroaryl-(1-6C)alkylamino, heteroarylcarbonylamino, heteroarylsulphonylamino, N-heteroarylsulphamoyl, heteroaryl-(2-6C)alkanoylamino, heteroaryl-(1-6C)alkoxy-(1-6C)alkyl, heteroaryl-(1-6C)alkylamino-(1-6C)alkyl, N-(1-6C)alkyl-heteroaryl-(1-6C)alkylamino-(1-6C)alkyl, heterocyclyl, heterocyclyl-(1-6C)alkyl, heterocyclyloxy, heterocyclyl-(1-6C)alkoxy, heterocyclylamino, N-(1-6C)alkyl-heterocyclylamino, heterocyclyl-(1-6C)alkylamino, N-(1-6C)alkyl-heterocyclyl-(1-6C)alkylamino, heterocyclylcarbonylamino, heterocyclylsulphonylamino, N-heterocyclylsulphamoyl, heterocyclyl-(2-6C)alkanoylamino, heterocyclyl-(1-6C)alkoxy-(1-6C)alkyl, heterocyclyl-(1-6C)alkylamino-(1-6C)alkyl and N-(1-6C)alkyl-heterocyclyl-(1-6C)alkylamino-(1-6C)alkyl, or Q is substituted with a (1-3C)alkylenedioxy group, and wherein any of the substituents on Q defined hereinbefore which comprises a $CH_2$ group which is attached to 2 carbon atoms or a $CH_3$ group which is attached to a carbon atom may optionally bear on each said $CH_2$ or $CH_3$ group a substituent selected from hydroxy, amino, (1-6C)alkoxy, (1-6C)alkylamino, di-[(1-6C)alkyl]amino and heterocyclyl, and wherein any aryl, heteroaryl or heterocyclyl group in a substituent on Q may optionally bear 1 or 2 substituents selected from hydroxy, halogeno, (1-6C)alkyl, (1-6C)alkoxy, carboxy, (1-6C)alkoxycarbonyl, N-(1-6C)alkylcarbamoyl, N,N-di-[(1-6C)alkyl]carbamoyl, (2-6C)alkanoyl, amino, (1-6C)alkylamino, di-[(1-6C)alkyl]amino, halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, aryl and aryl-(1-6C)alkyl;

or a pharmaceutically-acceptable salt or in-vivo-cleavable ester thereof;

except that 3-(5-benzamido-2-methylphenyl)-2-methyl-3,4-dihydroquinazolin-4-one, 3-[5-(4-methylbenzamido)-2-methylphenyl]-2-methyl-3,4-dihydroquinazolin-4-one and 3-[5-(4-methoxybenzamido)-2-methylphenyl]-2-methyl-3,4-dihydroquinazolin-4-one are excluded.

In this specification, the term (1-6C)alkyl includes straight-chain and branched-chain alkyl groups such as propyl, isopropyl and tert-butyl, and (3-6C)cycloalkyl groups such as cyclopropyl, cyclobutyl, cyclopentyl and cyclohexyl. However references to individual alkyl groups such as "propyl" are specific for the straight-chain version only, references to individual branched-chain alkyl groups such as "isopropyl" are specific for the branched-chain version only and references to individual cycloalkyl groups such as "cyclopentyl" are specific for that 5-membered ring only. An analogous convention applies to other generic terms, for example (1-6C)alkoxy includes methoxy, ethoxy, cyclopropyloxy and cyclopentyloxy, (1-6C)alkylamino includes methylamino, ethylamino, cyclobutylamino and cyclohexylamino, and di-[(1-6Calkyl]amino includes dimethylamino, diethylamino, N-cyclobutyl--methylamino and N-cyclohexyl-N-ethylamino.

It is to be understood that, insofar as certain of the compounds of Formula I defined above may exist in optically active or racemic forms by virtue of one or more asymmetric carbon atoms, the invention includes in its definition any such optically active or racemic form which possesses the property of inhibiting cytokines, in particular TNF. The synthesis of optically active forms may be carried out by standard techniques of organic chemistry well known in the art, for example by synthesis from optically active starting materials or by resolution of a racemic form. Similarly, inhibitory properties against TNF may be evaluated using the standard laboratory techniques referred to hereinafter.

Suitable values for the generic radicals referred to above include those set out below.

A suitable value for $R^1$ or Q when it is aryl, for a substituent on Q when it is aryl or for the aryl group within a $R^1$ substituent or a Q group or within a substituent on Q is, for example, phenyl, indenyl, indanyl, naphthyl, tetrahydronaphthyl or fluorenyl, preferably phenyl.

A suitable value for $R^1$ or Q when it is heteroaryl, for the heteroaryl group within a $R^1$ substituent or a Q group, for a substituent on Q when it is heteroaryl or for the heteroaryl group within a substituent on Q is, for example, an aromatic 5- or 6-membered monocyclic ring, a 9- or 10-membered bicyclic ring or a 13- or 14-membered tricyclic ring each with up to five ring heteroatoms selected from oxygen, nitrogen and sulphur, for example furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, benzothienyl, benzoxazolyl, benzimidazolyl, benzothiazolyl, indazolyl, benzofurazanyl, quinolyl, isoquinolyl, quinazolinyl, quinoxalinyl, cinnolinyl, naphthyridinyl, carbazolyl, dibenzofuranyl, dibenzothiophenyl, S,S-dioxodibenzothiophenyl, xanthenyl, dibenzo-1,4-dioxinyl, phenoxathiinyl, phenoxazinyl, dibenzothiinyl, phenothiazinyl, thianthrenyl, benzofuropyridyl, pyridoindolyl, acridinyl or phenanthridinyl, preferably furyl, thienyl, oxazolyl, isoxazolyl, imidazolyl, pyrazolyl, thiazolyl, isothiazolyl, pyridyl, pyridazinyl, pyrimidinyl, pyrazinyl, benzofuranyl, indolyl, benzothienyl, benzoxazolyl, benzimidazolyl, benzothiazolyl, indazolyl, benzofurazanyl, quinolyl, isoquinolyl, quinazolinyl, quinoxalinyl, naphthyridinyl, carbazolyl, dibenzofuranyl, dibenzothiophenyl or xanthenyl, more preferably furyl, thienyl, isoxazolyl, thiazolyl,.pyridyl, benzothienyl, benzofurazanyl, quinolyl, carbazolyl, dibenzofuranyl or dibenzothiophenyl.

A suitable value for $R^1$ or Q when it is heterocyclyl, for a substituent on Q when it is heterocyclyl or for the heterocyclyl group within a $R^1$ substituent or a Q group or within a substituent on Q is, for example, a non-aromatic saturated or partially saturated 3- to 10-membered monocyclic or bicyclic ring with up to five heteroatoms selected from oxygen, nitrogen and sulphur, for example oxiranyl, oxetanyl, azetidinyl, tetrahydrofuranyl, tetrahydropyranyl, pyrrolinyl, pyrrolidinyl, imidazolinyl, imidazolidinyl, pyrazolinyl, pyrazolidinyl, 1,1-dioxidoisothiazolidinyl, morpholinyl, tetrahydro-1,4-thiazinyl, 1,1-dioxotetrahydro-1,4-thiazinyl, piperidinyl, homopiperidinyl, piperazinyl, homopiperazinyl, dihydropyridinyl, tetrahydropyridinyl, dihydropyrimidinyl or tetrahydropyrimidinyl or benzo derivatives thereof such as 2,3-dihydrobenzofuranyl, 2,3-dihydrobenzothienyl, indolinyl, isoindolinyl, chromanyl and isochromanyl, preferably azetidin-1-yl, 3-pyrrolin-1-yl, pyrrolidin-1-yl, pyrrolidin-2-yl, 1,-dioxidoisothiazolidin-2-yl, morpholino, 1,1-dioxotetrahydro-4H-1,4-thiazin-4-yl, piperidin-3-yl, piperidin-4-yl, homopiperidin-1-yl, piperidino, piperazin-1-yl or homopiperazin-1-yl. A suitable value for such a group which bears 1 or 2 oxo or thioxo substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl.

A suitable value for Q when it is (3-7C)cycloalkyl is, for example, a non-aromatic mono- or bicyclic 3- to 7-membered carbon ring such as cyclopropyl, cyclobutyl, cyclopentyl, cyclohexyl, cycloheptyl or bicyclo[2.2.1]heptyl, preferably cyclobutyl, cyclopentyl, cyclohexyl or cycloheptyl, more preferably cyclohexyl.

Suitable values for various $R^1$, $R^2$ or $R^3$ groups, or for various substituents on Q or on an aryl, heteroaryl or heterocyclyl group within $R^1$ or on an aryl, heteroaryl or heterocyclyl group on a substituent on Q include:- for halogeno: fluoro, chloro, bromo and iodo;
for (1-6C)alkyl: methyl, ethyl, propyl, isopropyl, tert-butyl, cyclobutyl, cyclopentyl and cyclohexyl;
for (2-6C)alkenyl: vinyl and allyl;
for (2-6C)alkynyl: ethynyl and 2-propynyl;
for (1-6C)alkoxy: methoxy, ethoxy, propoxy, isopropoxy, cyclopropyloxy, butoxy, cyclobutyloxy and cyclopentyloxy;
for (1-6C)alkylamino: methylamino, ethylamino, propylamino, cyclobutylamino and cyclohexylamino;
for di-[(1-6C)alkyl]amino: dimethylamino, diethylamino and N-ethyl-N-methylamino;
for (1-6C)alkoxycarbonyl: methoxycarbonyl, ethoxycarbonyl, propoxycarbonyl and tert-butoxycarbonyl;
for N-(1-6C)alkylcarbamoyl: N-methylcarbamoyl, N-ethylcarbamoyl and N-propylcarbamoyl;
for N,N-di-[(1-6C)alkyl]carbamoyl: N,N-dimethylcarbamoyl, N-ethyl-N-methylcarbamoyl and N,N-diethylcarbamoyl;
for (2-6C)alkanoyl: acetyl and propionyl;
for halogeno-(1-6C)alkyl: fluoromethyl, chloromethyl, bromomethyl, difluoromethyl, dichloromethyl, dibromomethyl, 2-fluoroethyl, 2-chloroethyl and 2-bromoethyl;
for hydroxy-(1-6C)alkyl: hydroxymethyl, 2-hydroxyethyl, 1-hydroxyethyl and 3-hydroxypropyl;
for (1-6C)alkoxy-(1-6C)alkyl: methoxymethyl, ethoxymethyl, 1-methoxyethyl, 2-methoxyethyl, 2-ethoxyethyl and 3-methoxypropyl;
for cyano-(1-6C)alkyl: cyanomethyl, 2-cyanoethyl, 1-cyanoethyl and 3-cyanopropyl;
for amino-(1-6C)alkyl: aminomethyl, 2-aminoethyl, 1-aminoethyl and 3-aminopropyl;
for (1-6C)alkylamino-(1-6C)alkyl: methylaminomethyl, ethylaminomethyl, 1-methylaminoethyl, 2-methylaminoethyl, 2-ethylaminoethyl and 3-methylaminopropyl;
for di-[(1-6C)alkyl]amino-(1-6C)alkyl: dimethylaminomethyl, diethylaminomethyl, 1-dimethylaminoethyl, 2-dimethylaminoethyl and 3-dimethylaminopropyl.

Suitable values for $R^1$ or Q and suitable values for a substituent on $R^1$ or Q include:- for aryl-(1-6C)alkyl: benzyl, 2-phenylethyl, 2-phenylpropyl and 3-phenylpropyl;
for aryl-(1-6C)alkoxy: benzyloxy and 2-phenylethoxy;
for aryloxy: phenoxy and 2-naphthyloxy;
for arylamino: anilino;
for N-(1-6C)alkyl-arylamino: N-methylanilino and N-ethylanilino;
for aryl-(1-6C)alkylamino: benzylamino, 2-phenethylamino, 2-phenylpropylamino and 3-phenylpropylamino;
for N-(1-6C)alkyl-aryl-(1-6C)alkylamino: N-benzyl-N-methylamino;
for aroylamino: benzamido and 2-naphthoylamino;
arylsulphonylamino: benzenesulphonylamido;
for N-arylcarbamoyl: N-phenylcarbamoyl;
for N-arylsulphamoyl: N-phenylsulphamoyl;
for aryl-(2-6C)alkanoylamino: phenylacetamido and 3-phenylpropionamido;
for heteroaryl-(1-6C)alkyl: heteroarylmethyl, 2-heteroarylethyl, 2-heteroarylpropyl and 3-heteroarylpropyl;
for heteroaryl-(1-6C)alkoxy: heteroarylmethoxy and 2-heteroarylethoxy;
for N-(1-6C)alkyl-heteroarylamino: N-methylheteroarylamino;
for heteroaryl-(1-6C)alkylamino: heteroarylmethylamino, 2-heteroarylethylamino and 3-heteroarylpropylamino;
for N-(1-6C)alkyl-heteroaryl-(1-6C)alkylamino: N-methylheteroarylmethylamino and N-methyl-2-heteroarylethylamino;
for heteroaryl-(2-6C)alkanoylamino: heteroarylacetamido and 3-heteroarylpropionamido;
for heteroaryl-(1-6C)alkoxy-(1-6C)alkyl: heteroarylmethoxymethyl, 2-heteroarylethoxymethyl and 3-heteroarylpropoxymethyl;
for heteroaryl-(1-6C)alkylamino-(1-6C)alkyl: heteroarylmethylaminomethyl, 2-heteroarylethylaminomethyl and 3-heteroarylpropylaminomethyl;
for N-(1-6C)alkyl-heteroaryl-(1-6C)alkylamino-(1-6C)alkyl: N-heteroarylmethyl-N-methylaminomethyl, N-(2-heteroarylethyl)-N-methylaminomethyl and N-(3-heteroarylpropyl)-N-methylaminomethyl;
for heterocyclyl-(1-6C)alkyl: heterocyclylmethyl, 2-heterocyclylethyl, 2-heterocyclylpropyl and 3-heterocyclylpropyl;
for heterocyclyl-(1-6C)alkoxy: heterocyclylmethoxy and 2-heterocyclylethoxy;
for N-(1-6C)alkyl-heterocyclylamino: N-methylheterocyclylamino;
for heterocyclyl-(1-6C)alkylamino: heterocyclylmethylamino, 2-heterocyclylethylamino and 3-heterocyclylpropylamino;
for N-(1-6C)alkyl-heterocyclyl-(1-6C)alkylamino: N-methylheterocyclylmethylamino and N-methyl-2-heterocyclylethylamino;
for heterocyclyl-(2-6C)alkanoylamino: heterocyclylacetamido and 3-heterocyclylpropionamido;
for heterocyclyl-(1-6C)alkoxy-(1-6C)alkyl: heterocyclylmethoxymethyl, 2-heterocyclylethoxymethyl and 3-heterocyclylpropoxymethyl;
for heterocyclyl-(1-6C)alkylamino-(1-6C)alkyl: heterocyclylmethylaminomethyl, 2-heterocyclylethylaminomethyl and 3-heterocyclylethylaminomethyl;
for N-(1-6C)alkyl-heterocyclyl-(1-6C)alkylamino-(1-6C)alkyl: N-heterocyclylmethyl-N-methylaminomethyl, N-(2-heterocyclylethyl)-N-methylaminomethyl and N-(3-heterocyclylpropyl)-N-methylaminomethyl;
for (1-3C)alkylenedioxy: methylenedioxy, ethylenedioxy and trimethylenedioxy;
for (1-6C)alkylthio: methylthio, ethylthio and propylthio;
for (1-6C)alkylsulphinyl: methylsulphinyl, ethylsulphinyl and propylsulphinyl;
for (1-6C)alkylsulphonyl: methylsulphonyl, ethylsulphonyl and propylsulphonyl;
for (2-6C)alkanoyloxy: acetoxy and propionyloxy:
for (1-6C)alkanoylamino: formamido, acetamido and propionamido;
for N-(1-6C)alkyl-(1-6C)alkanoylamino: N-methylacetamido and N-methylpropionamido;
for N-(1-6C)alkylsulphamoyl: N-methylsulphamoyl and N-ethylsulphamoyl;
for N,N-di-[(1-6C)alkyl]sulphamoyl: N,N-dimethylsulphamoyl;
for (1-6C)alkanesulphonylamino: methanesulphonamido and ethanesulphonamido;

for N-(1-6C)alkyl-(1-6C)alkanesulphonylamino: N-methyl-methanesulphonylamino and N-methylethanesulphony-lamino;

for carboxy-(1-6C)alkyl: carboxymethyl, 1-carboxyethyl, 2-carboxyethyl, 3-carboxypropyl and 4-carboxybutyl;

for (1-6C)alkoxycarbonyl-(1-6C)alkyl: methoxycarbonylmethyl, ethoxycarbonylmethyl, tert-butoxycarbonylmethyl, 1-methoxycarbonylethyl, 1-ethoxycarbonylethyl, 2-methoxycarbonylethyl, 2-ethoxycarbonylethyl, 3-methoxycarbonylpropyl and 3-ethoxycarbonylpropyl;

for carbamoyl-(1-6C)alkyl: carbamoylmethyl, 1-carbamoylethyl, 2-carbamoylethyl and 3-carbamoylpropyl;

for N-(1-6C)alkylcarbamoyl-(1-6C)alkyl: N-methylcarbamoylmethyl, N-ethylcarbamoylmethyl, N-propylcarbamoylmethyl, 1-(N-methylcarbamoyl)ethyl, 1-(N-ethylcarbamoyl)ethyl, 2-(N-methylcarbamoyl)ethyl, 2-(N-ethylcarbamoyl)ethyl and 3-(N-methylcarbamoyl)propyl;

for N,N-di-[(1-6C)alkyl]carbamoyl-(1-6C)alkyl: N,N-dimethylcarbamoylmethyl, N-ethyl-N-methylcarbamoylmethyl, N,N-diethylcarbamoylmethyl, 1-(N,N-dimethylcarbamoyl)ethyl, 1-(N,N-diethylcarbamoyl)ethyl, 2-(N,N-dimethylcarbamoyl)ethyl, 2-(N,N-diethylcarbamoyl)ethyl, 3-(N,N-dimethylcarbamoyl)propyl and 4-(N,N-dimethylcarbamoyl)butyl;

for halogeno-(2-6C)alkoxy: 2-chloroethoxy, 2-bromoethoxy, 3-chloropropoxy, 1,1,2,2-tetrafluoroethoxy and 2,2,2-trifluoroethoxy;

for hydroxy-(2-6C)alkoxy: 2-hydroxyethoxy,-3-hydroxypropoxy, 2-hydroxy-1-methylethoxy,2-hydroxy-2-propoxy and 4-hydroxybutoxy;

for (1-6C)alkoxy-(2-6C)alkoxy: 2-methoxyethoxy, 2-ethoxyethoxy, 3-methoxypropoxy, 2-methoxy-1-methylethoxy and 4-ethoxybutoxy;

for cyano-(1-6C)alkoxy: cyanomethoxy, 2-cyanoethoxy and 3-cyanopropoxy;

for carboxy-(1-6C)alkoxy: carboxymethoxy, 1-carboxyethoxy, 2-carboxyethoxy and 3-carboxypropoxy;

for (1-6C)alkoxycarbonyl-(1-6C)alkoxy: methoxycarbonylmethoxy, ethoxycarbonylmethoxy, tert-butoxycarbonylmethoxy, 2-methoxycarbonylethoxy and 3-ethoxycarbonylpropoxy;

for carbamoyl-(1-6C)alkoxy: carbamoylmethoxy and 2-carbamoylethoxy;

for N-(1-6C)alkylcarbamoyl-(1-6C)alkoxy: N-methylcarbamoylmethoxy, 2-(N-ethylcarbamoyl)ethoxy and 3-(N-methylcarbamoyl)propoxy;

for N,N-di-[(1-6C)alkyl]carbamoyl-(1-6C)alkoxy: N,N-dimethylcarbamoylmethoxy, 2-(N,N-dimethylcarbamoyl)ethoxy and 3-(N,N-diethylcarbamoyl)propoxy;

for amino-(2-6C)alkoxy: 2-aminoethoxy, 2-amino-1-methylethoxy, 3-aminopropoxy, 2-amino-2-methylpropoxy and 4-aminobutoxy;

for (1-6C)alkylamino-(2-6C)alkoxy: 2-methylaminoethoxy, 2-methylamino-1-methylethoxy and 3-ethylaminopropoxy;

for di-[(1-6C)alkyl]amino-(2-6C)alkoxy: 2-dimethylaminoethoxy, 2-diethylaminoethoxy, 2-dimethylaminopropoxy, 2-dimethylamino-2-methylethoxy, 3-dimethylaminopropoxy and 4-dimethylaminobutoxy;

for halogeno-(2-6C)alkylamino: 2-fluoroethylamino, 2-chloroethylamino, 2-bromoethylamino, 3-fluoropropylamino and 3-chloropropylamino;

for hydroxy-(2-6C)alkylamino: 2-hydroxyethylamino, 3-hydroxypropylamino, 2-hydroxy-2-methylpropylamino and 4-hydroxybutylamino;

for (1-6C)alkoxy-(2-6C)alkylamino: 2-methoxyethylamino, 2-ethoxyethylamino, 3-methoxypropylamino and 3-ethoxypropylamino;

for cyano-(1-6C)alkylamino: cyanomethylamino, 2-cyanoethylamino and 3-cyanopropylamino;

for carboxy-(1-6C)alkylamino: carboxymethylamino, 1-carboxyethylamino, 2-carboxyethylamino and 3-carboxypropylamino;

for (1-6C)alkoxycarbonyl-(1-6C)alkylamino: methoxycarbonylmethylamino, 2-(ethoxycarbonyl)ethylamino and 3-(tert-butoxycarbonyl)propylamino;

for carbamoyl-(1-6C)alkylamino: carbamoylmethylamino and 2-carbamoylethylamino;

for N-(1-6C)alkylcarbamoyl-(1-6C)alkylamino: N-methylcarbamoylmethylamino, N-ethylcarbamoylmethylamino and 2-(N-methylcarbamoyl)ethylamino;

for N,N-di-[(1-6C)alkyl]carbamoyl-(1-6C)alkylamino: N,N-dimethylcarbamoylmethylamino, N,N-diethylcarbamoylmethylamino and 2-(N,N-dimethylcarbamoyl)ethylamino;

for amino-(2-6C)alkylamino: 2-aminoethylamino, 3-aminopropylamino, 2-amino-2-methylpropylamino and 4-aminobutylamino;

for (1-6C)alkylamino-(2-6C)alkylamino: 2-methylaminoethylamino, 2-ethylaminoethylamino, 2-propylaminoethylamino, 3-methylaminopropylamino, 3-ethylaminopropylamino, 2-methylamino-2-methylpropylamino and 4-methylaminobutylamino;

for di-[(1-6C)alkyl]amino-(2-6C)alkylamino: 2-dimethylaminoethylamino, 2-(N-ethyl-N-methylamino)ethylamino, 2-diethylaminoethylamino, 2-dipropylaminoethylamino, 3-dimethylaminopropylamino, 3-diethylaminopropylamino, 2-dimethylamino-2-methylpropylamino and 4-dimethylaminobutylamino;

for N-(1-6C)alkyl-halogeno-(2-6C)alkylamino: N-(2-chloroethyl)-N-methylamino, N-(2-bromoethyl)-N-methylamino and N-(2-bromoethyl)-N-ethylamino;

for N-(1-6C)alkyl-hydroxy-(2-6C)-alkylamino: N-(2-hydroxyethyl)-N-methylamino, N-(3-hydroxypropyl)-N-methylamino and N-ethyl-N-(2-hydroxyethyl)amino;

for N-(1-6C)alkyl-(1-6C)alkoxy-(2-6C)alkylamino: N-methyl-N-(2-methoxyethyl)amino, N-methyl-N-(3-methoxypropyl)amino and N-ethyl-N-(2-methoxyethyl)amino;

for N-(1-6C)alkyl-cyano-(1-6C)alkylamino: N-(cyanomethyl)-N-methylamino;

for N-(1-6C)alkyl-carboxy-(1-6C)alkylamino: N-carboxymethyl-N-methylamino and N-(2-carboxyethyl)-N-methylamino;

for N-(1-6C)alkyl-(1-6C)alkoxycarbonyl-(1-6C)alkylamino: N-methoxycarbonylmethyl-N-methylamino, N-(2-ethoxycarbonylethyl)-N-ethylamino and N-(2-tert-butoxycarbonylethyl)-N-methylamino;

for N-(1-6C)alkyl-carbamoyl-(1-6C)alkylamino: N-carbamoylmethyl-N-methylamino and N-(2-carbamoylethyl)-N-methylamino;

for N-(1-6C)alkyl-N-(1-6C)alkylcarbamoyl-(1-6C)alkylamino: N-(N-methylcarbamoylmethyl)-N-methylamino, N-(N-ethylcarbamoylmethyl)-N-methylamino and N-[2-(N-methylcarbamoyl)ethyl]-N-methylamino;

for N-(1-6C)alkyl-N,N-di-[(1-6C)alkyl]carbamoyl-(1-6C)alkylamino: N-(N,N-dimethylcarbamoylmethyl)-N-methylamino and N-[2-(N,N-dimethylcarbamoyl)ethyl]-N-methylamino;

for N-(1-6C)alkyl-amino-(2-6C)alkylamino: N-(2-aminoethyl)-N-methylamino, N-(3-aminopropyl)-N-methylamino and N-(4-aminobutyl)-N-methylamino;

for N-(1-6C)alkyl-(1-6C)alkylamino-(2-6C)alkylamino: N-(2-methylaminoethyl)-N-methylamino, N-(2-methylaminoethyl)-N-methylamino, N-(3-methylaminopropyl)-N-methylamino, N-(3-ethylaminopropyl)-N-ethylamino and N-(4-methylaminobutyl)-N-methylamino;

for N-(1-6C)alkyl-di-[(1-6C)alkyl]amino-(2-6C)alkylamino: N-(2-dimethylaminoethyl)-N-methylamino, N-(2-diethylaminoethyl)-N-methylamino, N-(3-dimethylaminopropyl)-N-methylamino and N-(4-dimethylaminobutyl)-N-methylamino;

for halogeno-(2-6C)alkanoylamino: 2-chloroacetamido and 3-chloropropionamido;

for hydroxy-(2-6C)alkanoylamino: 2-hydroxyacetamido and 3-hydroxypropionamido;

for (1-6C)alkoxy-(2-6C)alkanoylamino: 2-methoxyacetamido and 3-methoxypropionamido;

for cyano-(2-6C)alkanoylamino: 2-cyanoacetamido and 3-cyanopropionamido;

for carboxy-(2-6C)alkanoylamino: 2-carboxyacetamido and 3-carboxypropionamido;

for (1-6C)alkoxycarbonyl-(2-6C)alkanoylamino: 2-methoxycarbonylacetamido, 2-(tert-butoxycarbonyl)acetamido and 3-methoxycarbonylpropionamido;

for carbamoyl-(2-6C)alkanoylamino: 2-carbamoylacetamido, 3-carbamoylpropionamido and 4-carbamoylbutyramido;

for N-(1-6C)alkylcarbamoyl-(2-6C)alkanoylamino: 2-(N-methylcarbamoyl)acetamido and 3-(N-ethylcarbamoyl)propionamido;

for N,N-di-[(1-6C)alkyl]carbamoyl-(2-6C)alkanoylamino: 2-(N,N-dimethylcarbamoyl)acetamido, 2-(N,N-diethylcarbamoyl)acetamido and 3-(N,N-dimethylcarbamoyl)propionamido;

for amino-(2-6C)alkanoylamino: 2-aminoacetamido, 2-aminopropionamido and 3-aminopropionamido;

for (1-6C)alkylamino-(2-6C)alkanoylamino: 2-methylaminoacetamido, 2-ethylaminoacetamido, 2-methylaminopropionamido and 3-methylaminopropionamido;

for di-[(1-6C)alkyl]amino-(2-6C)alkanoylamino: 2-dimethylaminoacetamido, 2-diethylaminoacetamido, 2-dimethylaminopropionamido and 3-dimethylaminopropionamido.

When, as defined hereinbefore, any of the substituents on $R^1$ or Q which comprises a $CH_2$ group which is attached to 2 carbon atoms or a $CH_3$ group which is attached to a carbon atom may optionally bear on each said $CH_2$ or $CH_3$ group a substituent selected from hydroxy, amino, (1-6C)alkoxy, (1-6C)alkylamino, di-[(1-6C)alkyl]amino and heterocyclyl, suitable substituents so formed include, for example, substituted heterocyclyl-(1-6C)alkoxy groups such as 2-hydroxy-3-piperidinopropoxy and 2-hydroxy-3-morpholinopropoxy, substituted amino-(2-6C)alkoxy groups such as 3-amino-2-hydroxypropoxy, substituted (1-6C)alkylamino-(2-6C)alkoxy groups such as 2-hydroxy-3-methylaminopropoxy, substituted di-[(1-6C)alkyl]amino-(2-6C)alkoxy groups such as 3-dimethylamino-2-hydroxypropoxy, 3-[N-(3-dimethylaminopropyl)-N-methylamino]propoxy and 3-[N-(3-dimethylaminopropyl)-N-methylamino]-2-hydroxypropoxy, substituted heterocyclyl-(1-6C)alkylamino groups such as 2-hydroxy-3-piperidinopropylamino and 2-hydroxy-3-morpholinopropylamino, substituted amino-(2-6C)alkylamino groups such as 3-amino-2-hydroxypropylamino, substituted (1-6C)alkylamino-(2-6C)alkylamino groups such as 2-hydroxy-3-methylaminopropylamino, substituted di-[(1-6C)alkyl]amino-(2-6C)alkylamino groups such as 3-dimethylamino-2-hydroxypropylamino, 3-[N-(3-dimethylaminopropyl)-N-methylamino]propylamino and 3-[N-(3-dimethylaminopropyl)-N-methylamino]-2-hydroxypropylamino and substituted (1-6C)alkylamino-(1-6C)alkyl groups such as 2-dimethylaminoethylaminomethyl, 3-dimethylaminopropylaminomethyl, 3-dimethylamino-2,2-dimethylpropylaminomethyl, 2-morpholinoethylaminomethyl, 2-piperazin-1-ylethylaminomethyl and 3-morpholinopropylaminomethyl.

A suitable pharmaceutically-acceptable salt of a compound of the Formula Ia or Ib is, for example, an acid-addition salt of a compound of the Formula Ia or Ib which is sufficiently basic, for example an acid-addition salt with an inorganic or organic acid such as hydrochloric, hydrobromic, sulphuric, trifluoroacetic, citric or maleic acid; or, for example a salt of a compound of the Formula Ia or Ib which is sufficiently acidic, for example an alkali or alkaline earth metal salt such as a calcium or magnesium salt, or an ammonium salt, or a salt with an organic base such as methylamine, dimethylamine, trimethylamine, piperidine, morpholine or tris-(2-hydroxyethyl)amine.

Various forms of prodrugs are known in the art. For examples of such prodrug derivatives, see:

a) Design of Prodrugs, edited by H. Bundgaard, (Elsevier, 1985) and *Methods in Enzymology*, Vol. 42, p. 309-396, edited by K. Widder, et al. (Academic Press, 1985);

b) A Textbook of Drug Design and Development, edited by Krogsgaard-Larsen and H. Bundgaard, Chapter 5 "Design and Application of Prodrugs", by H. Bundgaard p. 113-191 (1991);

c) H. Bundgaard, *Advanced Drug Delivery Reviews*, 8, 1-38 (1992);

d) H. Bundgaard, et al., *Journal of Pharmaceutical Sciences*, 77, 285 (1988); and e) N. Kakeya, et al., *Chem. Pharm. Bull.*, 32, 692 (1984).

Examples of such pro-drugs may be used to form in-vivo-cleavable esters of a compound of the Formula Ia or Ib. An in-vivo-cleavable ester of a compound of the Formula Ia or Ib containing a carboxy group is, for example, a pharmaceutically-acceptable ester which is cleaved in the human or animal body to produce the parent acid. Suitable pharmaceutically-acceptable esters for carboxy include (1-6C)alkoxymethyl esters, for example methoxymethyl; (1-6C)alkanoyloxymethyl esters, for example pivaloyloxymethyl; phthalidyl esters; (3-8C)cycloalkoxycarbonyloxy(1-6C)alkyl esters, for example 1-cyclohexylcarbonyloxyethyl; 1,3-dioxolan-2-ylmethyl esters, for example 5-methyl-1,3-dioxolan-2-ylmethyl; and (1-6C)alkoxycarbonyloxyethyl esters, for example 1-methoxycarbonyloxyethyl; and may be formed at any carboxy group in the compounds of this invention.

Particular novel compounds of the invention include, for example, amide derivatives of the Formula Ia or Ib as appropriate, or pharmaceutically-acceptable salts thereof, wherein:-

(a) $R^3$ is hydrogen or (1-6C)alkyl such as methyl, ethyl, propyl and isopropyl, preferably $R^3$ is hydrogen, methyl or ethyl, more preferably hydrogen or methyl; and X, $R^1$, $R^2$, Q, m, n and q as appropriate have any of the meanings defined hereinbefore or in this section relating to particular novel compounds of the invention;

(b) Q is phenyl or a heteroaromatic 5- or 6-membered monocyclic ring or a 9- or 10-membered bicyclic ring with up to five ring heteroatoms selected from oxygen, nitrogen and sulphur which bears a basic substituent selected from the substituents for Q defined hereinbefore; and X, $R^1$, $R^2$, $R^3$, m, n and q as appropriate have any of the meanings defined hereinbefore or in this section relating to particular novel compounds of the invention;

(c) Q is phenyl indenyl, indanyl or fluorenyl which optionally bears 1, 2 or 3 substituents selected from the substituents for Q defined hereinbefore; and X, $R^1$, $R^2$, $R^3$, m, n and q as appropriate have any of the meanings defined hereinbefore or in this section relating to particular novel compounds of the invention;

(d) Q is phenyl or a heteroaromatic 5- or 6-membered monocyclic ring or a 9- or 10-membered bicyclic ring with up to five ring heteroatoms selected from oxygen, nitrogen and sulphur which bears a basic substituent selected from amino, (1-6C)alkylamino, di-[(1-6C)alkyl]amino, amino-(1-6C)alkyl, (1-6C)alkylamino-(1-6C)alkyl, di-[(1-6C)alkyl]amino-(1-6C)alkyl, amino-(2-6C)alkoxy, (1-6C)alkylamino-(2-6C)alkoxy, di-[(1-6C)alkyl]amino-(2-6C)alkoxy, amino-(2-6C)alkylamino, (1-6C)alkylamino-(2-6C)alkylamino, di-[(1-6C)alkyl]amino-(2-6C)alkylamino, N-(1-6C)alkyl-amino-(2-6C)alkylamino, N-(1-6C)alkyl-(1-6C)alkylamino-(2-6C)alkylamino, N-(1-6C)alkyl-di-[(1-6C)alkyl]amino-(2-6C)alkylamino, amino-(2-6C)alkanoylamino, (1-6C)alkylamino-(2-6C)alkanoylamino, di-[(1-6C)alkyl]amino-(2-6C)alkanoylamino, heteroaryl, heteroaryl-(1-6C)alkyl, heteroaryl-(1-6C)alkoxy, heterocyclyl, heterocyclyl-(1-6C)alkyl and heterocyclyl-(1-6C)alkoxy, and wherein any heteroaryl or heterocyclyl group in a basic substituent on Q may optionally bear 1 or 2 substituents selected from halogen, (1-6C)alkyl, (2-6C)alkanoyl, amino, (1-6C)alkylamino and di-[(1-6C)alkyl]amino; and X, $R^1$, $R^2$, $R^3$, m, n and q as appropriate have any of the meanings defined hereinbefore or in this section relating to particular novel compounds of the invention;

(e) Q is phenyl or a heteroaromatic 5- or 6-membered monocyclic ring or a 9- or 10-membered bicyclic ring with up to five ring heteroatoms selected from oxygen, nitrogen and sulphur which optionally bears 1, 2 or 3 substituents selected from hydroxy, halogeno, trifluoromethyl, cyano, nitro, amino, carboxy, (1-6C)alkyl, (1-6C)alkoxy, (1-6C)alkylamino, di-[(1-6C)alkyl]amino, (1-6C)alkoxycarbonyl, (2-6C)alkanoyl, halogeno-(1-6C)alkyl, (1-6C)alkoxy-(1-6C)alkyl, amino-(1-6C)alkyl, (1-6C)alkylamino-(1-6C)alkyl, di-[(1-6C)alkyl]amino-(1-6C)alkyl, halogeno-(2-6C)alkoxy, hydroxy-(2-6C)alkoxy, (1-6C)alkoxy-(2-6C)alkoxy, cyano-(1-6C)alkoxy, carboxy-(1-6C)alkoxy, (1-6C)alkoxycarbonyl-(1-6C)alkoxy, amino-(2-6C)alkoxy, (1-6C)alkylamino-(2-6C)alkoxy, di-[(1-6C)alkyl]amino-(2-6C)alkoxy, pyridyl, imidazolyl, pyridyl-(1-6C)alkyl, imidazolyl-(1-6C)alkyl, pyridyl-(1-6C)alkoxy, imidazolyl-(1-6C)alkoxy, pyrrolidinyl, piperidinyl, morpholinyl, piperazinyl, 4-(1-6C)alkylpiperazinyl, 4-(2-6C)alkanoylpiperazinyl, pyrrolidinyl-(1-6C)alkyl, piperidinyl-(1-6C)alkyl, morpholinyl-(1-6C)alkyl, piperazinyl-(1-6C)alkyl, 4-(1-6C)alkylpiperazinyl-(1-6C)alkyl, 4-(2-6C)alkanoylpiperazinyl-(1-6C)alkyl, pyrrolidinyloxy, piperidinyloxy, 1-(1-6C)alkylpiperidinyloxy, pyrrolidinyl-(2-6C)alkoxy, piperidinyl-(2-6C)alkoxy, morpholinyl-(2-6C)alkoxy, piperazinyl-(2-6C)alkoxy, 4-(1-6C)alkylpiperazinyl-(2-6C)alkoxy and 4-(2-6C)alkanoylpiperazinyl-(2-6C)alkoxy or Q bears a (1-3C)alkylenedioxy substituent; and X, $R^1$, $R^2$, $R^3$, m, n and q as appropriate have any of the meanings defined hereinbefore or in this section relating to particular novel compounds of the invention;

(f) Q is phenyl, indenyl, indanyl, fluorenyl or a heteroaromatic 5- or 6-membered monocyclic ring with up to three ring heteroatoms selected from oxygen, nitrogen and sulphur which optionally bears 1, 2 or 3 substituents selected from hydroxy, halogeno, trifluoromethyl, cyano, nitro, amino, carboxy, (1-6C)alkyl, (1-6C)alkoxy, (1-6C)alkylamino, di-[(1-6C)alkyl]amino, (1-6C)alkoxycarbonyl, (2-6C)alkanoyl, (1-6C)alkanoylamino, N-(1-6C)alkyl-(1-6C)alkanoylamino, (1-6C)alkanesulphonylamino, N-(1-6C)alkyl-(1-6C)alkanesulphonylamino, phenyl, furyl, thienyl, azetidinyl, pyrrolinyl, pyrrolidinyl, 1,1-dioxido-isothiazolidinyl, piperidinyl, homopiperidinyl, morpholinyl, piperazinyl, homopiperazinyl, pyrrolidinyl-(1-6C)alkyl, piperidinyl-(1-6C)alkyl, morpholinyl-(1-6C)alkyl and piperazinyl-(1-6C)alkyl, and wherein any phenyl, furyl, thienyl or heterocyclyl group in a substituent on Q may optionally bear 1 or 2 substituents selected from halogeno, (1-6C)alkyl, (1-6C)alkoxy and (2-6C)alkanoyl; and X, $R^1$, $R^2$, $R^3$, m, n and q as appropriate have any of the meanings defined hereinbefore or in this section relating to particular novel compounds of the invention;

(g) Q is phenyl, furyl, thienyl, oxazolyl, isoxazolyl, imidazolyl, pyrazolyl, thiazolyl, isothiazolyl, pyridyl, pyridazinyl, pyrimidinyl, pyrazinyl, benzofuranyl, indolyl, benzothienyl, benzoxazolyl, benzimidazolyl, benzothiazolyl, indazolyl, benzofurazanyl, quinolyl, isoquinolyl, quinazolinyl, quinoxalinyl or naphthyridinyl which optionally bears 1 or 2 substituents selected from those defined in paragraph (b), (d) or (e) hereinbefore; and X, $R^1$, $R^2$, $R^3$, m, n and q as appropriate have any of the meanings defined hereinbefore or in this section relating to particular novel compounds of the invention;

(h) Q is phenyl, 2- or 3-furyl, 2- or 3-thienyl, 2-, 4- or 5-oxazolyl, 3-, 4- or 5-isoxazolyl, 2-, 4- or 5-imidazolyl, 3- or 4-pyrazolyl, 2-, 4- or 5-thiazolyl, 3-, 4- or 5-isothiazolyl, 2-, 3- or 4-pyridyl, 3- or 4-pyridazinyl, 2-, 4- or 5-pyrimidinyl, 2-pyrazinyl, 2-, 3-, 5- or 6-benzofuranyl, 2-, 3-, 5- or 6-indolyl, 2-, 3-, 5- or 6-benzothienyl, 2-, 5- or 6-benzoxazolyl, 2-, 5- or 6-benzimidazolyl, 2-, 5- or 6-benzothiazolyl, 3-, 5- or 6-indazolyl, 5-benzofurazanyl, 2-, 3-, 6- or 7-quinolyl, 3-, 6- or 7-isoquinolyl, 2-, 6- or 7-quinazolinyl, 2-, 6- or 7-quinoxalinyl, or 1,8-naphthyridin-2-yl or 1,8-naphthyridin-3-yl which optionally bears 1 or 2 substituents selected from those defined in paragraph (b), (d) or (e) hereinbefore; and X, $R^1$, $R^2$, $R^3$, m, n and q as appropriate have any of the meanings defined hereinbefore or in this section relating to particular novel compounds of the invention;

(i) Q is a heteroaromatic 5- or 6-membered monocyclic ring, a 9- or 10-membered bicyclic ring or a 13- or 14-membered tricyclic ring each with up to five ring heteroatoms selected from oxygen, nitrogen and sulphur which optionally bears 1, 2 or 3 substituents selected from hydroxy, halogeno, trifluoromethyl, cyano, nitro, amino, carboxy, (1-6C)alkyl, (1-6C)alkoxy, (1-3C)alkylenedioxy, (1-6C)alkylamino, di-[(1-6C)alkyl]amino and (1-6C)alkoxycarbonyl; and X, $R^1$, $R^2$, $R^3$, m, n and q as appropriate have any of the meanings defined hereinbefore or in this section relating to particular novel compounds of the invention;

(j) Q is a heteroaromatic 13- or 14-membered tricyclic ring each with up to five ring heteroatoms selected from oxygen, nitrogen and sulphur which optionally bears 1, 2 or 3 substituents selected from hydroxy, halogeno, trifluoromethyl, cyano, nitro, amino, carboxy, (1-6C)alkyl, (1-6C)alkoxy, (1-3 C)alkylenedioxy, (1-6C)alkylamino, di-[(1-6C)alkyl]amino and (1-6C)alkoxycarbonyl; and X, $R^1$, $R^2$, $R^3$, m, n and q as appropriate have any of the meanings defined hereinbefore or in this section relating to particular novel compounds of the invention;

(k) Q is furyl, thienyl, oxazolyl, isoxazolyl, imidazolyl, pyrazolyl, thiazolyl, isothiazolyl, pyridyl, pyridazinyl, pyrimidinyl, pyrazinyl, benzofuranyl, indolyl, benzothiophenyl, benzoxazolyl, benzimidazolyl, benzothiazolyl, indazolyl, benzofurazanyl, quinolyl, isoquinolyl, quinazolinyl, quinoxalinyl, naphthyridinyl, carbazolyl, dibenzofuranyl, dibenzothiophenyl or xanthenyl which optionally bears 1 or 2 substituents selected from those defined in paragraph (i) hereinbefore; and X, $R^1$, $R^2$, $R^3$, m, n and q as appropriate have any of the meanings defined hereinbefore or in this section relating to particular novel compounds of the invention;

(l) Q is 1-, 2- or 3-carbazolyl, 1-, 2-, 3- or 4-dibenzofuranyl or 1-, 2-, 3- or 4-dibenzothiophenyl which optionally bears 1 or 2 substituents selected from those defined in paragraph (i) hereinbefore; and X, $R^1$, $R^2$, $R^3$, m, n and q as appropriate have any of the meanings defined hereinbefore or in this section relating to particular novel compounds of the invention;

(m) n is 0; and X, $R^1$, $R^3$, Q, m and q as appropriate have any of the meanings defined hereinbefore or in this section relating to particular novel compounds of the invention;

(n) n is 1 and $R^2$ is halogeno or (1-6C)alkyl; and X, $R^1$, $R^3$, Q, m and q as appropriate have any of the meanings defined hereinbefore or in this section relating to particular novel compounds of the invention;

(o) q is 0, and X, $R^1$, $R^2$, $R^3$, Q, m and n as appropriate have any of the meanings defined hereinbefore or in this section relating to particular novel compounds of the invention;

(p) m is 1 and $R^1$ is amino, (1-6C)alkylamino, di-[(1-6C)alkyl]amino, amino-(1-6C)alkyl, (1-6C)alkylamino-(1-6C)alkyl, di-[(1-6C)alkyl]amino-(1-6C)alkyl, amino-(2-6C)alkoxy, (1-6C)alkylamino-(2-6C)alkoxy, di-[(1-6C)alkyl]amino-(2-6C)alkoxy, amino-(2-6C)alkylamino, (1-6C)alkylamino-(2-6C)alkylamino, di-[(1-6C)alkyl]amino-(2-6C)alkylamino, N-(1-6C)alkyl-amino-(2-6C)alkylamino, N-(1-6C)alkyl-1-6C)alkylamino-(2-6C)alkylamino, N-(1-6C)alkyl-di-[(1-6C)alkyl]amino-(2-6C)alkylamino, heteroaryl, heteroaryl-(1-6C)alkyl, heteroaryl-(1-6C)alkoxy, heterocyclyl, heterocyclyl-(1-6C)alkyl, heterocyclyloxy or heterocyclyl-(1-6C)alkoxy, and wherein any heteroaryl or heterocyclyl group in a $R^1$ substituent may optionally bear 1 or 2 substituents selected from hydroxy, halogeno, (1-6C)alkyl, (1-6C)alkoxy, (2-6C)alkanoyl, amino, (1-6C)alkylamino and di-[(1-6C)alkyl]amino; and X, $R^2$, $R^3$, Q, n and q as appropriate have any of the meanings defined hereinbefore or in this section relating to particular novel compounds of the invention;

(q) m is 1 and $R^1$ is amino, (1-6C)alkylamino, di-[(1-6C)alkyl]amino, amino-(1-6C)alkyl, (1-6C)alkylamino-(1-6C)alkyl, di-[(1-6C)alkyl]amino-(1-6C)alkyl, amino-(2-6C)alkoxy, (1-6C)alkylamino-(2-6C)alkoxy, di-[(1-6C)alkyl]amino-(2-6C)alkoxy, amino-(2-6C)alkylamino, (1-6C)alkylamino-(2-6C)alkylamino, di-[(1-6C)alkyl]amino-(2-6C)alkylamino, N-(1-6C)alkyl-amino-(2-6C)alkylamino, N-(1-6C)alkyl-(1-6C)alkylamino-(2-6C)alkylamino, N-(1-6C)alkyl-di-[(1-6C)alkyl]amino-(2-6C)alkylamino, pyridyl, imidazolyl, pyridyl-(1-6C)alkyl, imidazolyl-(1-6C)alkyl, pyridyl-(1-6C)alkoxy, imidazolyl-(1-6C)alkoxy, pyrrolidinyl, piperidinyl, morpholinyl, piperazinyl, 4-(1-6C)alkylpiperazinyl, homopiperazinyl, 4-(1-6C)alkylhomopiperazinyl, 4-(2-6C)alkanoylpiperazinyl, pyrrolidinyl-(1-6C)alkyl, piperidinyl-(1-6C)alkyl, morpholinyl-(1-6C)alkyl, piperazinyl-(1-6C)alkyl, 4-(1-6C)alkylpiperazinyl-(1-6C)alkyl, 4-(2-6C)alkanoylpiperazinyl-(1-6C)alkyl, pyrrolidinyloxy, piperidinyloxy, 1-(1-6C)alkylpiperidinyloxy, pyrrolidinyl-(2-6C)alkoxy, piperidinyl-(2-6C)alkoxy, morpholinyl-(2-6C)alkoxy, piperazinyl-(2-6C)alkoxy, 4-(1-6C)alkylpiperazinyl-(2-6C)alkoxy or 4-(2-6C)alkanoylpiperazinyl-(2-6C)alkoxy; and X, $R^2$, $R^3$, Q, n and q as appropriate have any of the meanings defined hereinbefore or in this section relating to particular novel compounds of the invention;

(r) m is 1 and $R^1$ is hydroxy, halogeno, trifluoromethyl, cyano, mercapto, nitro, carboxy, (1-6C)alkoxycarbonyl, (1-6C)alkyl or (1-6C)alkoxy; and X, $R^2$, $R^3$, Q, n and q as appropriate have any of the meanings defined hereinbefore or in this section relating to particular novel compounds of the invention;

(s) m is 2 and the first $R^1$ substituent is selected from the substituents specified in paragraph (q) hereinbefore and the second $R^1$ substituent is selected from the substituents specified in paragraph (r) hereinbefore; and X, $R^2$, $R^3$, Q, n and q as appropriate have any of the meanings defined hereinbefore or in this section relating to particular novel compounds of the invention; and (t) X is —NHCO—; and $R^1$, $R^2$, $R^3$, Q, m, n and q as appropriate have any of the meanings defined hereinbefore or in this section relating to particular novel compounds of the invention.

A preferred compound of the invention is an amide derivative of the Formula Ib wherein $R^3$ is hydrogen, methyl or ethyl;

m is 0, 1 or 2;

$R^1$ is hydroxy, fluoro, chloro, bromo, trifluoromethyl, cyano, methyl, ethyl, methoxy, ethoxy, amino, methylamino, ethylamino, dimethylamino, diethylamino, methylaminomethyl, ethylaminomethyl, dimethylaminomethyl, diethylaminomethyl, 2-aminoethoxy, 3-aminopropoxy, 2-methylaminoethoxy, 2-ethylaminoethoxy, 3-methylaminopropoxy, 3-ethylaminopropoxy, 2-dimethylaminoethoxy, 2-diethylaminoethoxy, 3-dimethylaminopropoxy, 3-diethylaminopropoxy, 2-aminoethylamino, 3-aminopropylamino, 2-methylaminoethylamino, 2-ethylaminoethylamino, 3-methylaminopropylamino, 3-ethylaminopropylamino, 2-dimethylaminoethylamino, 2-diethylaminoethylamino, 3-dimethylaminopropylamino, 3-diethylaminopropylamino, N-(2-aminoethyl)-N-methylamino, N-(3-aminopropyl)-N-methylamino, N-(2-methylaminoethyl)-N-methylamino, N-(2-ethylaminoethyl)-N-methylamino, N-(3-methylaminopropyl)-N-methylamino, N-(3-ethylaminopropyl)-N-methylamino, N-(2-dimethylaminoethyl)-N-methylamino, N-(2-diethylaminoethyl)-N-methylamino, N-(3-dimethylaminopropyl)-N-methylamino, N-(3-diethylaminopropyl)-N-methylamino, pyridyl, pyridylmethyl, pyridylmethoxy, pyrrolidinyl, piperidinyl, morpholinyl, piperazinyl, 4-methylpiperazinyl, homopiperazinyl, 4-methylhomopiperazinyl, 4-acetylpiperazinyl, pyrrolidinylmethyl, piperidinylmethyl, morpholinylmethyl, piperazinylmethyl, 4-methylpiperazinylmethyl, 4-acetylpiperazinylmethyl, pyrrolidinyloxy, 1-methylpyrrolidinyloxy, piperidinyloxy, 1-methylpiperidinyloxy, 2-(pyrrolidinyl)ethoxy, 3-(pyrrolidinyl)propoxy, 2-(piperidinyl)ethoxy, 3-(piperidinyl)propoxy, 2-(morpholinyl)ethoxy, 3-(morpholinyl)propoxy, 2-(piperazinyl)ethoxy, 3-(piperazinyl)propoxy, 2-(4-methylpiperazinyl)ethoxy, 3-(4-methylpiperazinyl)propoxy, 2-(4-acetylpiperazinyl)ethoxy or 3-(4-acetylpiperazinyl)propoxy;

n is 0 or 1;

$R^2$ is fluoro, chloro, bromo, methyl or ethyl;

q is 0; and

Q is phenyl, furyl, thienyl, oxazolyl, isoxazolyl, imidazolyl, pyrazolyl, thiazolyl, isothiazolyl, pyridyl, pyridazinyl, pyrimidinyl, pyrazinyl, benzofuranyl, indolyl, benzothienyl, benzoxazolyl, benzimidazolyl, benzothiazolyl, indazolyl, benzofurazanyl, quinolyl, isoquinolyl, quinazolinyl, quinoxalinyl or naphthyridinyl which optionally bears 1 or 2 substituents selected from hydroxy, fluoro, chloro, trifluoromethyl, cyano, amino, methyl, ethyl, methoxy, ethoxy, methylenedioxy, methylamino, ethylamino, dimethylamino, diethylamino, aminomethyl, methylaminomethyl, ethylaminomethyl, dimethylaminomethyl, diethylaminomethyl, 2-hydroxyethoxy, 3-hydroxypropoxy, 2-methoxyethoxy, 2-ethoxyethoxy, 3-methoxypropoxy, 3-ethoxypropoxy, 2-aminoethoxy, 3-aminopropoxy, 2-methylaminoethoxy, 2-ethylaminoethoxy, 3-methylaminopropoxy, 3-ethylaminopropoxy, 2-dimethylaminoethoxy, 2-diethylaminoethoxy, 3-dimethylaminopropoxy, 3-diethylaminopropoxy, pyridyl, pyridylmethyl, pyridylmethoxy, pyrrolidinyl, piperidinyl, morpholinyl, piperazinyl, 4-methylpiperazinyl, homopiperazinyl, 4-methylhomopiperazinyl, 4-acetylpiperazinyl, pyrrolidinylmethyl, piperidinylmethyl, morpholinylmethyl, piperazinylmethyl, 4-methylpiperazinylmethyl, 4-acetylpiperazinylmethyl, pyrrolidinyloxy, 1-methylpyrrolidinyloxy, piperidinyloxy, 1-methylpiperidinyloxy, 2-(pyrrolidinyl) ethoxy, 3-(pyrrolidinyl)propoxy, 2-(piperidinyl)ethoxy, 3-(piperidinyl)propoxy, 2-(morpholinyl)ethoxy, 3-(morpholinyl)propoxy, 2-(piperazinyl)ethoxy, 3-(piperazinyl)propoxy, 2-(4-methylpiperazinyl)ethoxy, 3-(4-methylpiperazinyl)propoxy, 2-(4-acetylpiperazinyl)ethoxy and 3-(4-acetylpiperazinyl)propoxy;

or a pharmaceutically-acceptable salt thereof.

A further preferred compound of the invention is an amide derivative of the Formula Ia wherein X is —NHCO— or —CONH—;

$R^3$ is hydrogen, methyl or ethyl;

m is 0, 1 or 2;

$R^1$ is hydroxy, fluoro, chloro, bromo, trifluoromethyl, cyano, methyl, ethyl, methoxy, ethoxy, amino, methylamino, ethylamino, dimethylamino, diethylamino, methylaminomethyl, ethylaminomethyl, dimethylaminomethyl, diethylaminomethyl, 2-aminoethoxy, 3-aminopropoxy, 2-methylaminoethoxy, 2-ethylaminoethoxy, 3-methylaminopropoxy, 3-ethylaminopropoxy, 2-dimethylaminoethoxy, 2-diethylaminoethoxy, 3-dimethylaminopropoxy, 3-diethylaminopropoxy, 2-aminoethylamino, 3-aminopropylamino, 2-methylaminoethylamino, 2-ethylaminoethylamino, 3-methylaminopropylamino, 3-ethylaminopropylamino, 2-dimethylaminoethylamino, 2-diethylaminoethylamino, 3-dimethylaminopropylamino, 3-diethylaminopropylamino, N-(2-aminoethyl)-N-methylamino, N-(3-aminopropyl)-N-methylamino, N-(2-methylaminoethyl)-N-methylamino, N-(2-ethylaminoethyl)-N-methylamino, N-(3-methylaminopropyl)-N-methylamino, N-(3-ethylaminopropyl)-N-methylamino, N-(2-dimethylaminoethyl)-N-methylamino, N-(2-diethylaminoethyl)-N-methylamino, N-(3-dimethylaminopropyl)-N-methylamino, N-(3-diethylaminopropyl)-N-methylamino, pyridyl, pyridylmethyl, pyridylmethoxy, 3-pyrrolinyl, pyrrolidinyl, piperidinyl, homopiperidinyl, morpholinyl, piperazinyl, 4-methylpiperazinyl, 4-ethylpiperazinyl, homopiperazinyl, 4-methylhomopiperazinyl, 4-acetylpiperazinyl, pyrrolidinylmethyl, piperidinylmethyl, morpholinylmethyl, piperazinylmethyl, 4-methylpiperazinylmethyl, homopiperazinylmethyl, 4-methylhomopiperazinylmethyl, 4-acetylpiperazinylmethyl, pyrrolidinyloxy, 1-methylpyrrolidinyloxy, piperidinyloxy, 1-methylpiperidinyloxy, homopiperidinyloxy, 1-methylhomopiperidinyloxy, 2-(pyrrolidinyl)ethoxy, 3-(pyrrolidinyl)propoxy, 2-(piperidinyl)ethoxy, 3-(piperidinyl)propoxy, 2-(morpholinyl)ethoxy, 3-(morpholinyl)propoxy, 2-(piperazinyl)ethoxy, 3-(piperazinyl)propoxy, 2-(4-methylpiperazinyl)ethoxy, 3-(4-methylpiperazinyl)propoxy, 2-(4-acetylpiperazinyl)ethoxy, 3-(4-acetylpiperazinyl)propoxy, 3-dimethylaminopropylaminomethyl, 3-dimethylamino-2,2-dimethylpropylaminomethyl, 2-(1-methylpyrrolidinylethyl)aminomethyl, 3-pyrrolidinylpropylaminomethyl, 2-morpholinylethylaminomethyl, 3-morpholinylpropylaminomethyl, 2-piperazinylethylaminomethyl, 3-(4-methylpiperazinylpropyl)aminomethyl, pyridylmethoxy, imidazolylmethoxy, thiazolylmethoxy and 2-methylthiazolylmethoxy;

n is 0 or 1;

$R^2$ is fluoro, chloro, bromo, methyl or ethyl;

q is 0; and

Q is phenyl, indenyl, indanyl, tetrahydronaphthyl, fluorenyl, furyl, thienyl, oxazolyl, isoxazolyl, imidazolyl, pyrazolyl, thiazolyl, isothiazolyl, pyridyl, pyridazinyl, pyrimidinyl, pyrazinyl, benzofuranyl, indolyl, benzothienyl, benzoxazolyl, benzimidazolyl, benzothiazolyl, indazolyl, benzofurazanyl, quinolyl, isoquinolyl, quinazolinyl, quinoxalinyl, naphthyridinyl, carbazolyl, dibenzofuranyl, dibenzothiophenyl or xanthenyl which optionally bears 1 or 2 substituents selected from hydroxy, fluoro, chloro, trifluoromethyl, cyano, amino, methyl, ethyl, methoxy, ethoxy, propoxy, isopropoxy, cyclopentyloxy, methylenedioxy, methylamino, ethylamino, dimethylamino, diethylamino, acetamido, propionamido, N-methylacetamido, methanesulphonamido, N-methylmethanesulphonamido, aminomethyl, methylaminomethyl, ethylaminomethyl, dimethylaminomethyl, diethylaminomethyl, 2-hydroxyethoxy, 3-hydroxypropoxy, 2-methoxyethoxy, 2-ethoxyethoxy, 3-methoxypropoxy, 3-ethoxypropoxy, 2-aminoethoxy, 3-aminopropoxy, 2-methylaminoethoxy, 2-ethylaminoethoxy, 3-methylaminopropoxy, 3-ethylaminopropoxy, 2-dimethylaminoethoxy, 2-diethylaminoethoxy, 3-dimethylaminopropoxy, 3-diethylaminopropoxy, phenyl, furyl, thienyl, pyridyl, pyridylmethyl, pyridylmethoxy, azetidinyl, 3-pyrrolinyl, pyrrolidinyl, piperidinyl, homopiperidinyl, morpholinyl, piperazinyl, 4-methylpiperazinyl, homopiperazinyl, 4-methylhomopiperazinyl, 4-acetylpiperazinyl, pyrrolidinylmethyl, piperidinylmethyl, morpholinylmethyl, piperazinylmethyl, 4-methylpiperazinylmethyl, 4-acetylpiperazinylmethyl, pyrrolidinyloxy, 1-methylpyrrolidinyloxy, piperidinyloxy, 1-methylpiperidinyloxy, 2-(pyrrolidinyl) ethoxy, 3-(pyrrolidinyl)propoxy, 2-(piperidinyl)ethoxy, 3-(piperidinyl)propoxy, 2-(morpholinyl)ethoxy, 3-(morpholinyl)propoxy, 2-(piperazinyl)ethoxy, 3-(piperazinyl)propoxy, 2-(4-methylpiperazinyl)ethoxy, 3-(4-methylpiperazinyl)propoxy, 2-(4-acetylpiperazinyl)ethoxy and 3-(4-acetylpiperazinyl)propoxy, and wherein any phenyl, furyl, thienyl, pyridyl or heterocyclyl group in a substituent on Q may optionally bear 1 or 2 substituents selected from fluoro, chloro, methyl and methoxy;

or a pharmaceutically-acceptable salt thereof.

A further preferred compound of the invention is an amide derivative of the Formula Ib wherein $R^3$ is hydrogen or methyl;

m is 0, 1 or 2;

$R^1$ is hydroxy, fluoro, chloro, bromo, trifluoromethyl, cyano, methyl, ethyl, methoxy, ethoxy, amino, methylamino, ethylamino, dimethylamino, diethylamino, methylaminomethyl, ethylaminomethyl, dimethylaminomethyl, diethylaminomethyl, 2-aminoethoxy, 3-aminopropoxy, 2-methylaminoethoxy, 2-ethylaminoethoxy, 3-methylaminopropoxy, 3-ethylaminopropoxy, 2-dimethylaminoethoxy, 2-diethylaminoethoxy, 3-dimethylaminopropoxy, 3-diethylaminopropoxy, 2-aminoethylamino, 3-aminopropylamino, 2-methylaminoethylamino, 2-ethylaminoethylamino, 3-methylaminopropylamino, 3-ethylaminopropylamino, 2-dimethylaminoethylamino, 2-diethylaminoethylamino, 3-dimethylaminopropylamino, 3-diethylaminopropylamino, N-(2-aminoethyl)-N-methylamino, N-(3-aminopropyl)-N-methylamino, N-(2-methylaminoethyl)-N-methylamino, N-(2-ethylaminoethyl)-N-methylamino, N-(3-methylaminopropyl)-N-methylamino, N-(3-ethylaminopropyl)-N-methylamino, N-(2-dimethylaminoethyl)-N-methylamino, N-(2-diethylaminoethyl)-N-methylamino, N-(3-dimethylaminopropyl)-N-methylamino, N-(3-diethylaminopropyl)-N-methylamino, 2-pyridylmethyl, 3-pyridylmethyl, 4-pyridylmethyl, 2-pyridylmethoxy, 3-pyridylmethoxy, 4-pyridylmethoxy, pyrrolidin-1-yl, piperidino, morpholino, piperazin-1-yl, 4-methylpiperazin-1-yl, homopiperazin-1-yl, 4-methylhomopiperazin-1-yl, 4-acetylpiperazin-1-yl, pyrrolidin-1-ylmethyl, piperidinomethyl, morpholinomethyl, piperazin-1-ylmethyl, 4-methylpiperazin-1-ylmethyl, 4-acetylpiperazin-1-ylmethyl, pyrrolidin-3-yloxy, 1-methylpyrrolidin-3-yloxy, piperidin-4-yloxy, 1-methylpiperidinyloxy, 2-(pyrrolidin-1-yl)ethoxy, 3-(pyrrolidin-1-yl)propoxy, 2-piperidinoethoxy, 3-piperidinopropoxy, 2-morpholinoethoxy, 3-morpholinopropoxy, 2-piperazin-1-ylethoxy, 3-piperazin-1-ylpropoxy, 2-(4-methylpiperazin-1-yl)ethoxy, 3-(4-methylpiperazin-1-yl)propoxy, 2-(4-acetylpiperazin-1-yl)ethoxy or 3-(4-acetylpiperazin-1-yl)propoxy;

n is 0 or 1;

$R^2$ is fluoro, chloro or methyl;

q is 0; and

Q is phenyl, 2-furyl, 2-thienyl, 4-oxazolyl, 5-isoxazolyl, 4-thiazolyl, 5-isothiazolyl, 2-pyridyl, 3-pyridyl, 4-pyridyl, 2-benzofuranyl, 2-indolyl, 2-benzothienyl, 2-benzoxazolyl, 2-benzimidazolyl, 2-benzothiazolyl, 4-benzofurazanyl, 2-quinolyl, 6-quinolyl, 7-quinolyl, 3-isoquinolyl, 6-quinazolinyl, 7-quinazolinyl, 6-quinoxalinyl or 7-quinoxalinyl which optionally bears 1 or 2 substituents selected from hydroxy, fluoro, chloro, trifluoromethyl, cyano, amino, methyl, ethyl, methoxy, ethoxy, methylenedioxy, methylamino, ethylamino, dimethylamino, diethylamino, aminomethyl, methylaminomethyl, ethylaminomethyl, dimethylaminomethyl, diethylaminomethyl, 2-hydroxyethoxy, 3-hydroxypropoxy, 2-methoxyethoxy, 2-ethoxyethoxy, 3-methoxypropoxy, 3-ethoxypropoxy, 2-aminoethoxy, 3-aminopropoxy, 2-methylaminoethoxy, 2-ethylaminoethoxy, 3-methylaminopropoxy, 3-ethylaminopropoxy, 2-dimethylaminoethoxy, 2-diethylaminoethoxy, 3-dimethylaminopropoxy, 3-diethylaminopropoxy, 2-pyridyl, 3-pyridyl, 4-pyridyl, 2-pyridylmethyl, 3-pyridylmethyl, 4-pyridylmethyl, 2-pyridylmethoxy, 3-pyridylmethoxy, 4-pyridylmethoxy, pyrrolidin-1-yl, piperidino, morpholino, piperazin-1-yl, 4-methylpiperazin-1-yl, homopiperazin-1-yl, 4-methylhomopiperazin-1-yl, 4-acetylpiperazin-1-yl, pyrrolidin-1-ylmethyl, piperidinomethyl, morpholinomethyl, piperazin-1-ylmethyl, 4-methylpiperazin-1-ylmethyl, 4-acetylpiperazin-1-ylmethyl, pyrrolidin-3-yloxy, 1-methylpyrrolidin-3-yloxy, piperidin-4-yloxy, 1-methylpiperidin-4-yloxy, 2-pyrrolidin-1-ylethoxy, 3-pyrrolidin-1-ylpropoxy, 2-piperidinoethoxy, 3-piperidinopropoxy, 2-morpholinoethoxy, 3-morpholinopropoxy, 2-piperazin-1-ylethoxy, 3-piperazin-1-ylpropoxy, 2-(4-methylpiperazin-1-yl)ethoxy, 3-(4-methylpiperazin-1-yl)propoxy, 2-(4-acetylpiperazin-1-yl)ethoxy and 3-(4-acetylpiperazin-1-yl)propoxy;

or a pharmaceutically-acceptable salt thereof.

A further preferred compound of the invention is an amide derivative of the Formula Ib wherein $R^3$ is hydrogen or methyl;

m is 0, 1 or 2;

$R^1$ is hydroxy, fluoro, chloro, bromo, trifluoromethyl, cyano, methyl, ethyl, methoxy, ethoxy, amino, methylamino, ethylamino, dimethylamino, diethylamino, methylaminomethyl, ethylaminomethyl, dimethylaminomethyl, diethylaminomethyl, 2-aminoethoxy, 3-aminopropoxy, 2-methylaminoethoxy, 2-ethylaminoethoxy, 3-methylaminopropoxy, 3-ethylaminopropoxy, 2-dimethylaminoethoxy, 2-diethylaminoethoxy, 3-dimethylaminopropoxy, 3-diethylaminopropoxy, 2-aminoethylamino, 3-aminopropylamino, 2-methylaminoethylamino, 2-ethylaminoethylamino, 3-methylaminopropylamino, 3-ethylaminopropylamino, 2-dimethylaminoethylamino, 2-diethylaminoethylamino, 3-dimethylaminopropylamino, 3-diethylaminopropylamino, N-(2-aminoethyl)-N-methylamino, N-(3-aminopropyl)-N-methylamino, N-(2-methylaminoethyl)-N-methylamino, N-(2-ethylaminoethyl)-N-methylamino, N-(3-methylaminopropyl)-N-methylamino, N-(3-ethylaminopropyl)-N-methylamino, N-(2-dimethylaminoethyl)-N-methylamino, N-(2-diethylaminoethyl)-N-methylamino, N-(3-dimethylaminopropyl)-N-methylamino, N-(3-diethylaminopropyl)-N-methylamino, 2-pyridylmethyl, 3-pyridylmethyl, 4-pyridylmethyl, 2-pyridylmethoxy, 3-pyridylmethoxy, 4-pyridylmethoxy, pyrrolidin-1-yl, piperidino, morpholino, piperazin-1-yl, 4-methylpiperazin-1-yl, homopiperazin-1-yl, 4-methylhomopiperazin-1-yl, 4-acetylpiperazin-1-yl, pyrrolidin-1-ylmethyl, piperidinomethyl, morpholinomethyl, piperazin-1-ylmethyl, 4-methylpiperazin-1-ylmethyl, 4-acetylpiperazin-1-ylmethyl, pyrrolidin-3-yloxy, 1-methylpyrrolidin-3-yloxy, piperidin-4-yloxy, 1-methylpiperidin-4-yloxy, 2-(pyrrolidin-1-yl)ethoxy, 3-(pyrrolidin-1-yl)propoxy, 2-piperidinoethoxy, 3-piperidinopropoxy, 2-morpholinoethoxy, 3-morpholinopropoxy, 2-piperazin-1-ylethoxy, 3-piperazin-1-ylpropoxy, 2-(4-methylpiperazin-1-yl)ethoxy, 3-(4-methylpiperazin-1-yl)propoxy, 2-(4-acetylpiperazin-1-yl)ethoxy or 3-(4-acetylpiperazin-1-yl)propoxy;

n is 0 or 1;

$R^2$ is fluoro, chloro or methyl;

q is 0; and

Q is phenyl, 2-pyridyl, 3-pyridyl or 4-pyridyl which optionally bears 1 or 2 substituents selected from hydroxy, fluoro, chloro, trifluoromethyl, cyano, amino, methyl, ethyl, methoxy, ethoxy, methylenedioxy, methylamino, ethylamino, dimethylamino, diethylamino, aminomethyl, methylaminomethyl, ethylaminomethyl, dimethylaminomethyl, diethylaminomethyl, 2-hydroxyethoxy, 3-hydroxypropoxy, 2-methoxyethoxy, 2-ethoxyethoxy, 3-methoxypropoxy, 3-ethoxypropoxy, 2-aminoethoxy, 3-aminopropoxy, 2-methylaminoethoxy, 2-ethylaminoethoxy, 3-methylaminopropoxy, 3-ethylaminopropoxy, 2-dimethylaminoethoxy, 2-diethylaminoethoxy, 3-dimethylaminopropoxy, 3-diethylaminopropoxy, 2-pyridyl, 3-pyridyl, 4-pyridyl, 2-pyridylmethyl, 3-pyridylmethyl, 4-pyridylmethyl, 2-pyridylmethoxy, 3-pyridylmethoxy, 4-pyridylmethoxy, pyrrolidin-1-yl, piperidino, morpholino, piperazin-1-yl, 4-methylpiperazin-1-yl, homopiperazin-1-yl, 4-methylhomopiperazin-1-yl, 4-acetylpiperazin-1-yl, pyrrolidin-1-ylmethyl, piperidinomethyl, morpholinomethyl, piperazin- 1-ylmethyl, 4-methylpiperazin-1-ylmethyl, 4-acetylpiperazin-1-ylmethyl, pyrrolidin-3-yloxy, 1-methylpyrrolidin-3-yloxy, piperidin-4-yloxy, 1-methylpiperidin-4-yloxy, 2-pyrrolidin-1-ylethoxy, 3-pyrrolidin-1-ylpropoxy, 2-piperidinoethoxy, 3-piperidinopropoxy, 2-morpholinoethoxy, 3-morpholinopropoxy, 2-piperazin-1-ylethoxy, 3-piperazin-1-ylpropoxy, 2-(4-methylpiperazin-1-yl)ethoxy, 3-(4-methylpiperazin-1-yl)propoxy, 2-(4-acetylpiperazin-1-yl)ethoxy and 3-(4-acetylpiperazin-1-yl)propoxy;

or a pharmaceutically-acceptable salt thereof.

A further preferred compound of the invention is an amide derivative of the Formula Ib wherein $R^3$ is hydrogen or methyl;

m is 1 or 2;

$R^1$ is hydroxy, fluoro, chloro, methyl, methoxy, dimethylaminomethyl, diethylaminomethyl, 2-dimethylaminoethoxy, 2-diethylaminoethoxy, 3-dimethylaminopropoxy, 3-diethylaminopropoxy, 3-dimethylamino-2-hydroxypropoxy, 3-diethylamino-2-hydroxypropoxy, 2-aminoethylamino, 3-aminopropylamino, 4-aminobutylamino, 3-methylaminopropylamino, 2-dimethylaminoethylamino, 2-diethylaminoethylamino, 3-dimethylaminopropylamino, 4-dimethylaminobutylamino, 3-amino-2-hydroxypropylamino, 3-dimethylamino-2-hydroxypropylamino, N-(2-dimethylaminoethyl)-N-methylamino, N-(3-dimethylaminopropyl)-N-methylamino, pyrrolidin-1-yl, morpholino, piperidino, piperazin-1-yl, 4-methylpiperazin-1-yl, 4-ethylpiperazin-1-yl, 4-(2-hydroxyethyl)piperazin-1-yl, homopiperazin-1-yl, 4-methylhomopiperazin-1-yl, piperazin-1-ylmethyl, 4-methylpiperazin-1-ylmethyl, homopiperazin-1-ylmethyl, 4-methylhomopiperazin-1-ylmethyl, morpholinomethyl, 3-aminopyrrolidin-1-ylmethyl, 3-hydroxypyrrolidin-1-ylmethyl, 4-(2-hydroxyethyl)piperazin-1-ylmethyl, pyrrolidin-3-yloxy, 1-methylpyrrolidin-3-yloxy, piperidin-4-yloxy, 1-methylpiperidin-4-yloxy, 1-benzylpiperidin-4-yloxy, 2-pyrrolidin-1-ylethoxy, 3-pyrrolidin-1-ylpropoxy, 2-piperidinoethoxy, 3-piperidinopropoxy, 2-morpholinoethoxy, 3-morpholinopropoxy, 2-piperazin-1-ylethoxy, 3-piperazin-1-ylpropoxy, 2-(4-methylpiperazin-1-yl)ethoxy, 3-(4-methylpiperazin-1-yl)propoxy, 2-hydroxy-3-pyrrolidin-1-ylpropoxy, 2-hydroxy-3-piperidinopropoxy, 2-hydroxy-3-morpholinopropoxy, piperidin-4-ylamino, 1-methylpiperidin-4-ylamino, 1-benzylpiperidin-4-ylamino, 2-pyrrolidin-1-ylethylamino, 3-pyrrolidin-1ylpropylamino, 2-morpholinoethylamino, 3-morpholinopropylamino, 2-piperidinoethylamino, 3-piperidinopropylamino, 2-piperazin-1-ylethylamino, 3-piperazin-1-ylpropylamino, 2-(4-methylpiperazin-1-yl)ethylamino, 3-(4-methylpiperazin-1-yl)propylamino, 2-(1-methylpyrrolidin-2-yl)ethylamino, 3-(1-methylpyrrolidin-2-yl)propylamino, 2-dimethylaminoethylaminomethyl, 3-dimethylaminopropylaminomethyl, 3-dimethylamino-2,2-dimethylpropylaminomethyl, 2-(1-methylpyrrolidin-2-ylethyl)aminomethyl, 3-pyrrolidin-1-ylpropylaminomethyl, 2-morpholinoethylaminomethyl, 3-morpholinopropylaminomethyl, 2-piperazin-1-ylethylaminomethyl, 3-(4-methylpiperazin-1-ylpropyl)aminomethyl or 2-pyridylmethoxy;

n is 0 or 1;

$R^2$ is chloro or methyl;

q is 0; and

Q is 2-pyridyl, 3-pyridyl or 4-pyridyl which bears a substituent selected from pyrrolidin-1-yl, 3-hydroxypyrrolidin-1-yl, 2-hydroxymethylpyrrolidin-1-yl, morpholino, piperidino, 4-hydroxypiperidin-1-yl, piperazin-1-yl and 4-methylpiperazin-1-yl;

or a pharmaceutically-acceptable salt thereof.

An especially preferred compound of the invention is an amide derivative of the Formula Ib wherein $R^3$ is hydrogen or methyl;

m is 1 and $R^1$ is selected from diethylaminomethyl, N-(3-dimethylaminopropyl)-N-methylamino, pyrrolidin-1-yl, morpholino, piperidino, piperazin-1-yl, 4-methylpiperazin-1-yl, 4-ethylpiperazin-1-yl, homopiperazin-1-yl, 4-methylhomopiperazin-1-yl, piperazin-1-ylmethyl, 4-methylpiperazin-1-ylmethyl, 4-methylhomopiperazin-1-ylmethyl, morpholinomethyl, 3-aminopyrrolidin-1-ylmethyl, 3-hydroxypyrrolidin-1-ylmethyl, pyrrolidin-3-yloxy, piperidin-4-yloxy, 2-pyrrolidin-1-ylethoxy, 2-piperidinoethoxy, 2-morpholinoethoxy, 3-dimethylaminopropylaminomethyl, 3-dimethylamino-2,2-dimethylpropylaminomethyl, 2-(1-methylpyrrolidin-2-ylethyl)aminomethyl, 3-pyrrolidin-1-ylpropylaminomethyl, 2-morpholinoethylaminomethyl, 3-morpholinopropylaminomethyl, 2-piperazin-1-ylethylaminomethyl, 3-(4-methylpiperazin-1-ylpropyl)aminomethyl and 2-pyridylmethoxy;

n is 0 or 1;

$R^2$ is methyl;

q is 0; and

Q is 3-pyridyl or 4-pyridyl which bears a substituent selected from pyrrolidin-1-yl, morpholino, piperidino, piperazin-1-yl and 4-methylpiperazin-1-yl;

or a pharmaceutically-acceptable salt thereof.

A further especially preferred compound of the invention is an amide derivative of the Formula Ib wherein $R^3$ is hydrogen or methyl;

m is 1 and $R^1$ is selected from diethylaminomethyl, N-(3-dimethylaminopropyl)-N-methylamino, 3-pyrrolin-1-yl, pyrrolidin-1-yl, morpholino, piperidino, homopiperidin-1-yl, piperazin-1-yl, 4-methylpiperazin-1-yl, 4-ethylpiperazin-1-yl, homopiperazin-1-yl, 4-methylhomopiperazin-1-yl, piperazin-1-ylmethyl, 4-methylpiperazin-1-ylmethyl, homopiperazin-1-ylmethyl, 4-methylhomopiperazin-1-ylmethyl, morpholinomethyl, 3-aminopyrrolidin-1-ylmethyl, 3-hydroxypyrrolidin-1-ylmethyl, pyrrolidin-3-yloxy, N-methylpyrrolidin-3-yloxy, piperidin-4-yloxy, N-methylpiperidin-4-yloxy, homopiperidin-4-yloxy, N-methylhomopiperidin-4-yloxy, 2-pyrrolidin-1-ylethoxy, 2-piperidinoethoxy, 2-morpholinoethoxy, 3-dimethylaminopropylaminomethyl, 3-dimethylamino-2,2-dimethylpropylaminomethyl, 2-(1-methylpyrrolidin-2-ylethyl)aminomethyl, 3-pyrrolidin-1-ylpropylaminomethyl, 2-morpholinoethylaminomethyl, 3-morpholinopropylaminomethyl, 2-piperazin-1-ylethylaminomethyl, 3-(4-methylpiperazin-1-ylpropyl)aminomethyl, 2-pyridylmethoxy, 4-thiazolylmethoxy and 2-methylthiazol-4-ylmethoxy;

n is 0 or 1;

$R^2$ is methyl;

q is 0; and

Q is phenyl which bears 1 or 2 substituents selected from fluoro, chloro, trifluoromethyl, methoxy, cyclopentyloxy, acetamido, N-methylmethanesulphonamido, 2-furyl, azetidin-1-yl, 3-pyrrolin-1-yl, pyrrolidin-1-yl, morpholino, piperidino, homopiperidin-1-yl, piperazin-1-yl, homopiperazin-1-yl, 4-methylpiperazin-1-yl and 4-methylhomopiperazin-1-yl, or Q is 1-fluorenyl or 4-dibenzofuranyl, or Q is 3-pyridyl or 4-pyridyl which bears a substituent selected from azetidin-1-yl, 3-pyrrolin-1-yl, pyrrolidin-1-yl, morpholino, piperidino, homopiperidino, piperazin-1-yl, homopiperazin-1-yl, 4-methylpiperazin-1-yl and 4-methylhomopiperazin-1-yl;

or a pharmaceutically-acceptable salt thereof.

A further especially preferred compound of the invention is an amide derivative of the Formula Ib wherein $R^3$ is hydrogen or methyl;
m is 1 and $R^{1\ is}$ 4-methylpiperazin-1-yl or N-(3-dimethylaminopropyl)-N-methylamino;
n is 0 or 1;
$R^2$ is 6-methyl;
q is 0; and
Q is 2-morpholinopyrid-4-yl;

or a pharmaceutically-acceptable salt thereof.

A further especially preferred compound of the invention is an amide derivative of the Formula Ib wherein $R^3$ is hydrogen or methyl;
m is 1 and $R^1$ is 4-methylpiperazin-1-yl, 4-methylhomopiperazin-1-yl or N-(3-dimethylaminopropyl)-N-methylamino;
n is 0 or 1;
$R^2$ is 6-methyl;
q is 0; and
Q is 2-pyrrolidin-1-ylpyrid-4-yl, 2-(3-pyrrolin-1-yl)pyrid-4-yl, 2-piperidinopyrid-4-yl, 2-morpholinopyrid-4-yl, 1-fluorenyl, dibenzofuran-4-yl, 3-acetamidophenyl or 3-(2-furyl)phenyl;

or a pharmaceutically-acceptable salt thereof.

A further especially preferred compound of the invention is an amide derivative of the Formula Ib wherein $R^3$ is hydrogen;
m is 1 and $R^1$ is piperazin-1-yl, 4-methylpiperazin-1-yl, 4-methylhomopiperazin-1-yl or N-(3-dimethylaminopropyl)-N-methylamino;
n is 0 or 1;
$R^2$ is 6-methyl or 6-fluoro;
q is 0; and
Q is 2-azetidin-1-ylpyrid-4-yl, 2-pyrrolidin-1-ylpyrid-4-yl, 2-(3-pyrrolin-1-yl)pyrid-4-yl, 2-piperidinopyrid-4-yl, 2-morpholinopyrid-4-yl, 1-fluorenyl, dibenzofuran-4-yl, 5-(4-chlorophenyl)furan-2-yl, 4-(4-chlorophenyl)thien-2-yl, 2-methoxyphenyl, 3-ethoxyphenyl, 3-(1,1,2,2-tetrafluoroethoxy)phenyl, 3,4-methylenedioxyphenyl, 3-acetamidophenyl, 3-(4-fluorophenyl)phenyl, 3-(2-furyl)phenyl, 3-fluoro-5-pyrrolidin-1-ylphenyl, 3-fluoro-5-piperidinophenyl, 3-fluoro-5-morpholinophenyl or 3-morpholino-5-trifluoromethylphenyl;

or a pharmaceutically-acceptable salt thereof.

A particular preferred compound of the invention is, for example:-
6-[N-(3-dimethylaminopropyl)-N-methylamino]-3-[2-methyl-5-(2-morpholinopyrid-4-ylcarbonylamino)phenyl]-3,4-dihydroquinazolin-4-one, 6-[N-(3-dimethylaminopropyl)-N-methylamino]-2-methyl-3-[2-methyl-5-(2-morpholinopyrid-4-ylcarbonylamino)phenyl]-3,4-dihydroquinazolin-4-one, 6-[N-(3-dimethylaminopropyl)-N-methylamino]-3-[5-(2-morpholinopyrid-4-ylcarbonylamino)phenyl]-3,4-dihydroquinazolin-4-one, 6-(4-methylpiperazin-1-yl)-3-[2-methyl-5-(2-morpholinopyrid-4-ylcarbonylamino) phenyl]-3,4-dihydroquinazolin-4-one or 8-[N-(3-dimethylaminopropyl)-N-methylamino]-3-[2-methyl-5-(2-morpholinopyrid-4-ylcarbonylamino)phenyl]-3,4-dihydroquinazolin-4-one;

or a pharmaceutically-acceptable salt thereof.

A further particular preferred compound of the invention is, for example:-
3-[2-methyl-5-(2-pyrrolidin-1-ylpyrid-4-ylcarbonylamino) phenyl]-6-(4-methylpiperazin-1-yl)-3,4-dihydroquinazolin-4-one, 3-[2-methyl-5-(2-piperidinopyrid-4-ylcarbonylamino)phenyl]-6-(4-methylpiperazin-1-yl)-3,4-dihydroquinazolin-4-one, 3-{(2-methyl-5-[2-(3-pyrrolin-1-yl)pyrid-4-ylcarbonylamino]phenyl}-6-(4-methylpiperazin-1-yl)-3,4-dihydroquinazolin-4-one, 3-[5-dibenzofuran-4-ylcarbonylamino-2-methylphenyl]-6-(4-methylpiperazin-1-yl)-3,4-dihydroquinazolin-4-one, 3-{5-[3-(2-furyl)benzamido]-2-methylphenyl}-6-(4-methylpiperazin-1-yl)-3,4-dihydroquinazolin-4-one or 3-[5-(3-acetamidobenzamido]-2-methylphenyl}-6-(4-methylpiperazin-1-yl)-3,4-dihydroquinazolin-4-one, or a pharmaceutically-acceptable salt thereof An amide derivative of the Formula Ia or Ib, or a pharmaceutically-acceptable salt or in-vivo-cleavable ester thereof, may be prepared by any process known to be applicable to the preparation of chemically-related compounds. Such processes, when used to prepare a novel amide derivative of the Formula Ia or Ib are provided as a further feature of the invention and are illustrated by the following representative process variants in which, unless otherwise stated, X, $R^1$, $R^2$, $R^3$, m, n, q and Q have any of the meanings defined hereinbefore. Necessary starting materials may be obtained by standard procedures of organic chemistry. The preparation of such starting materials is described in conjunction with the following representative process variants and within the accompanying Examples. Alternatively necessary starting materials are obtainable by analogous procedures to those illustrated which are within the ordinary skill of an organic chemist.

(a) A compound of the Formula Ia, or a pharmaceutically-acceptable, salt or in-vivo-cleavable ester thereof, may be prepared by reacting an N-phenyl-2-aminobenzamide of the Formula II

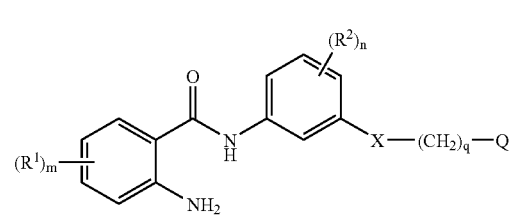

II with a carboxylic acid of the Formula III, or a reactive derivative thereof,

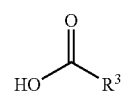

III wherein variable groups are as defined hereinbefore and wherein any functional group is protected if necessary, and:
(i) removing any protecting groups; and
(ii) optionally forming a pharmaceutically-acceptable salt or in-vivo-cleavable ester.

A suitable reactive derivative of a carboxylic acid of the Formula III is, for example, an acyl halide, for example an acyl chloride formed by the reaction of the acid and an inorganic acid chloride, for example thionyl chloride; a mixed anhydride, for example an anhydride formed by the reaction of the acid and a chloroformate such as isobutyl chloroformate; an active ester, for example an ester formed by the reaction of the acid with a phenol such as pentafluorophenol, with an ester such as pentafluorophenyl trifluoroacetate or with an alcohol such as N-hydroxybenzotriazole; an acyl azide, for example an azide formed by the reaction of the acid and an azide such as diphenylphosphoryl azide; an acyl cyanide, for example a cyanide formed by the reaction of an acid and a cyanide such as diethylphosphoryl cyanide; or the product of the reaction of the acid and a carbodiimide such as dicyclohexylcarbodiimide. A preferred reactive derivative of a carboxylic acid of the Formula III is, for example, an ester of the corresponding ortho acid of the carboxylic acid of the Formula III, for example a trialkyl ester such as a trimethyl or triethyl ester. For a carboxylic acid of the Formula III wherein $R^3$ is hydrogen, a suitable ortho acid ester is triethyl orthoformate and for a carboxylic acid of the Formula III wherein $R^3$ is methyl, a suitable ortho acid ester is triethyl orthoacetate.

The reaction may conveniently be carried out in the presence of a suitable base such as, for example, an alkali or alkaline earth metal carbonate, alkoxide, hydroxide or hydride, for example sodium carbonate, potassium carbonate, sodium ethoxide, potassium butoxide, sodium hydroxide, potassium hydroxide, sodium hydride or potassium hydride, or an organometallic base such as an alkyl-lithium, for example n-butyl-lithium, or a dialkylamino-lithium, for example lithium di-isopropylamide, or, for example, an organic amine base such as, for example, pyridine, 2,6-lutidine, collidine, 4-dimethylaminopyridine, triethylamine, morpholine or diazabicyclo[5.4.0]undec-7-ene.

The reaction may also conveniently be carried out in the presence of a suitable acid such as, for example, an inorganic or organic acid such as hydrochloric, hydrobromic, sulphuric, acetic, trifluoroacetic, citric or maleic acid.

The reaction is also preferably carried out in a suitable inert solvent or diluent, for example methanol, ethanol, tetrahydrofuran, methylene chloride, 1,2-dimethoxyethane, N,N-dimethylformamide, N,N-dimethylacetamide, N-methylpyrrolidin-2-one, dimethylsulphoxide or acetone, and at a temperature in the range, for example, 0 to 150° C., conveniently at or near 75° C.

Protecting groups may in general be chosen from any of the groups described in the literature or known to the skilled chemist as appropriate for the protection of the group in question and may be introduced by conventional methods. Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower", as in, for example, lower alkyl, signifies that the group to which it is applied preferably has 1-4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxy protecting group may be the residue of an ester-forming aliphatic or arylaliphatic alcohol or of an ester-forming silanol (the said alcohol or silanol preferably containing 1-20 carbon atoms). Examples of carboxy protecting groups include straight or branched chain (1-12C)alkyl groups (for example isopropyl, tert-butyl); lower alkoxy lower alkyl groups (for example methoxymethyl, ethoxymethyl, isobutoxymethyl); lower aliphatic acyloxy lower alkyl groups, (for example acetoxymethyl, propionyloxymethyl, butyryloxymethyl, pivaloyloxymethyl); lower alkoxycarbonyloxy lower alkyl groups (for example 1-methoxycarbonyloxyethyl, 1-ethoxycarbonyloxyethyl); aryl lower alkyl groups (for example benzyl, p-methoxybenzyl, o-nitrobenzyl, p-nitrobenzyl, benzhydryl and phthalidyl); tri(lower alkyl)silyl groups (for example trimethylsilyl and tert-butyldimethylsilyl); tri(lower alkyl)silyl lower alkyl groups (for example trimethylsilylethyl); and (2-6C)alkenyl groups (for example allyl and vinylethyl). Methods particularly appropriate for the removal of carboxyl protecting groups include for example acid-, base-, metal- or enzymically-catalysed hydrolysis.

Examples of hydroxy protecting groups include lower alkyl groups (for example tert-butyl), lower alkenyl groups (for example allyl); lower alkanoyl groups (for example acetyl); lower alkoxycarbonyl groups (for example tert-butoxycarbonyl); lower alkenyloxycarbonyl groups (for example allyloxycarbonyl); aryl lower alkoxycarbonyl groups (for example benzoyloxycarbonyl, p-methoxybenzyloxycarbonyl, o-nitrobenzyloxycarbonyl, p-nitrobenzyloxycarbonyl); tri lower alkylsilyl (for example trimethylsilyl, tert-butyldimethylsilyl) and aryl lower alkyl (for example benzyl) groups.

Examples of amino protecting groups include formyl, aralkyl groups (for example benzyl and substituted benzyl, p-methoxybenzyl, nitrobenzyl and 2,4-dimethoxybenzyl, and triphenylmethyl); di-p-anisylmethyl and furylmethyl groups; lower alkoxycarbonyl (for example tert-butoxycarbonyl); lower alkenyloxycarbonyl (for example allyloxycarbonyl); aryl lower alkoxycarbonyl groups (for example benzyloxycarbonyl, p-methoxybenzyloxycarbonyl, o-nitrobenzyloxycarbonyl, p-nitrobenzyloxycarbonyl; trialkylsilyl (for example trimethylsilyl and tert-butyldimethylsilyl); alkylidene (for example methylidene); benzylidene and substituted benzylidene groups.

Methods appropriate for removal of hydroxy and amino protecting groups include, for example, acid-, base-, metal- or enzymically-catalysed hydrolysis for groups such as p-nitrobenzyloxycarbonyl, hydrogenation for groups such as benzyl and photolytically for groups such as o-nitrobenzyloxycarbonyl.

The reader is referred to Advanced Organic Chemistry, 4th Edition, by Jerry March, published by John Wiley & Sons 1992, for general guidance on reaction conditions and reagents. The reader is referred to Protective Groups in Organic Synthesis, 2nd Edition, by Green et al., published by John Wiley & Sons for general guidance on protecting groups.

The N-phenyl-2-aminobenzamide of the Formula II may be prepared by reduction of the corresponding nitro compound of the Formula IV

IV

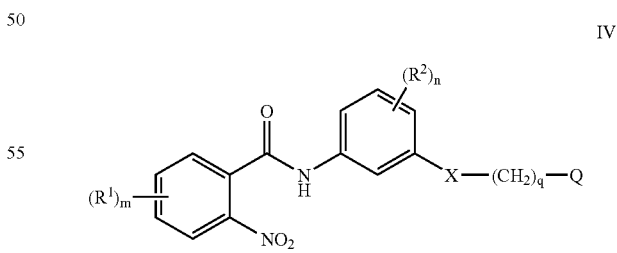

Typical reaction conditions include the use of ammonium formate or hydrogen gas in the presence of a catalyst, for example a metallic catalyst such as palladium-on-carbon. Alternatively a dissolving metal reduction may be carried out, for example using iron in the presence of an acid, for example an inorganic or organic acid such as hydrochloric, hydrobromic, sulphuric or acetic acid. The reaction is conveniently carried out in the presence of an organic solvent (preferably a polar protic solvent) and preferably with heating for example to about 60° C. Any functional groups are protected and deprotected as necessary.

The nitrobenzene of the Formula IV wherein X is —NHCO— may be prepared by the reaction of the aniline of the Formula V

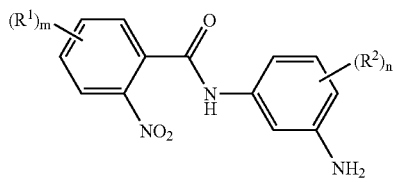

V with a carboxylic acid of the Formula VI, or a reactive derivative thereof as defined hereinbefore,

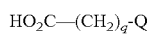

VI under standard amide bond forming conditions, wherein variable groups are as defined hereinbefore and wherein any functional group is protected if necessary.

Typical conditions include activating the carboxy group of the compound of Formula VI, for example by treatment with a halo reagent (for example oxalyl chloride) to form an acyl halide in an organic solvent at ambient temperature and then reacting the activated compound with the aniline of Formula V. Any functional groups are protected and deprotected as necessary. Conveniently a carbodiimide coupling reagent is used in the presence of an organic solvent (preferably an anhydrous polar aprotic organic solvent) at a non-extreme temperature, for example in the region −10 to 40° C., typically at ambient temperature of about 20° C.

An aniline of the Formula V may be prepared by the reaction of a benzoic acid of Formula VII, or an activated derivative thereof as defined hereinbefore,

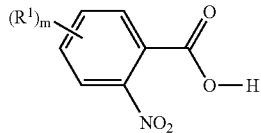

VII with an aniline of Formula VIII

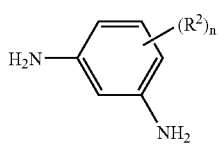

VIII under suitable amide bond forming conditions as defined hereinbefore.

The nitrobenzene of Formula IV wherein X is —NHCO— may also be prepared by the reaction of a benzoic acid of Formula VII, or an activated derivative thereof as defined hereinbefore, with an aniline of Formula IX

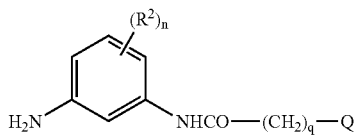

IX under suitable amide bond forming conditions as defined hereinbefore.

Corresponding reactions as illustrated in the Examples are used to prepare the nitrobenzene of the Formula IV wherein X is —CONH—.

(b) A compound of the Formula Ia wherein X is —NHCO—, or a pharmaceutically-acceptable salt or in-vivo-cleavable ester thereof, may be prepared by reacting an aniline of the Formula X

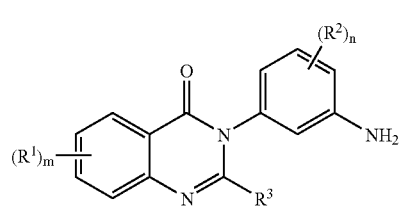

X with a carboxylic acid of the Formula VI, or a reactive derivative thereof as defined hereinbefore,

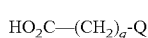

VI under standard amide bond forming conditions as defined hereinbefore, wherein variable groups are as defined hereinbefore and wherein any functional group is protected if necessary, and:

(i) removing any protecting groups; and
(ii) optionally forming a pharmaceutically-acceptable salt- or in-vivo-cleavable ester.

The reaction is preferably carried out in the presence of a suitable base as defined hereinbefore The reaction is preferably carried out in a suitable inert solvent or diluent, for example tetrahydrofuran, methylene chloride, 1,2-dimethoxyethane, N,N-dimethylformamide, N,N-dimethylacetamide, N-methylpyrrolidin-2-one, dimethylsulphoxide or acetone, and at a temperature in the range, for example, −78 to 150° C., conveniently at or near ambient temperature.

Typically a carbodiimide coupling reagent is used in the presence of an organic solvent (preferably an anhydrous polar aprotic organic solvent) at a non-extreme temperature, for example in the region −10 to 40° C., typically at ambient temperature of about 20° C.

An aniline of the Formula X may be prepared by reduction under standard conditions as defined hereinbefore of the corresponding nitro compound of the Formula XI

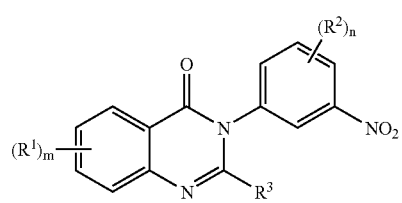

XI

The nitro compound of the Formula XI may be prepared by by reacting an N-phenyl-2-aminobenzamide of the Formula XII

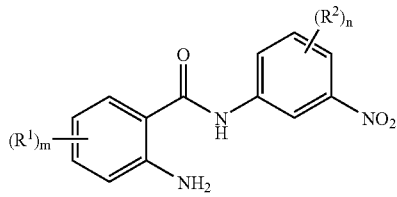

with a carboxylic acid of the Formula III, or a reactive derivative thereof,

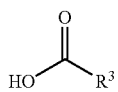

wherein variable groups are as defined hereinbefore and wherein any functional group is protected if necessary (c) A compound of the Formula Ia wherein $R^1$ or a substituent on Q is (1-6C)alkoxy or substituted (1-6C)alkoxy, (1-6C)alkylthio, (1-6C)alkylamino, di-[(1-6C)alkyl]amino or substituted (1-6C)alkylamino may be prepared by the alkylation, conveniently in the presence of a suitable base as defined hereinbefore, of an amide derivative of the Formula Ia wherein $R^1$ or a substituent on Q is hydroxy, mercapto or amino as appropriate.

The reaction is preferably carried out in the presence of a suitable inert solvent or diluent, for example a halogenated solvent such as methylene chloride, chloroform or carbon tetrachloride, an ether such as tetrahydrofuran or 1,4-dioxan, an aromatic solvent such as toluene, or a dipolar aprotic solvent such as N,N-dimethylformamide, N,N-dimethylacetamide, N-methylpyrrolidin-2-one or dimethylsulphoxide. The reaction is conveniently carried out at a temperature in the range, for example, 10 to 150° C., preferably in the range 20 to 80° C.

A suitable alkylating agent is, for example, any agent known in the art for the alkylation of hydroxy to alkoxy or substituted alkoxy, or for the alkylation of mercapto to alkylthio, or for the alkylation of amino to alkylamino or substituted alkylamino, for example an alkyl or substituted alkyl halide, for example a (1-6C)alkyl chloride, bromide or iodide or a substituted (1-6C)alkyl chloride, bromide or iodide, in the presence of a suitable base as defined hereinbefore, in a suitable inert solvent or diluent as defined hereinbefore and at a temperature in the range, for example, 10 to 140° C., conveniently at or near ambient temperature.

(d) A compound of the Formula Ia wherein a substituent on Q is amino, (1-6C)alkylamino, di-[(1-6C)alkyl]amino, substituted (1-6C)alkylamino, substituted N-(1-6C)alkyl-(2-6C)alkylamino or a N-linked heterocyclyl group may be prepared by the reaction, conveniently in the presence of a suitable base as defined hereinbefore, of an amide derivative of the Formula Ia wherein a substituent on Q is a suitable leaving group with an appropriate amine.

A suitable leaving group is, for example, a halogeno group such as fluoro, chloro or bromo, a (1-6C)alkanesulphonyloxy group such as methanesulphonyloxy or an arylsulphonyloxy group such as 4-toluenesulphonyloxy.

The reaction is conveniently carried out in the presence of a suitable inert diluent or carrier as defined hereinbefore and at a temperature in the range, for example, 20 to 200° C., conveniently in the range 75 to 150° C.

(e) A compound of the Formula Ia wherein $R^1$ or a substituent on Q is (1-6C)alkanoylamino or substituted (2-6C)alkanoylamino may be prepared by the acylation of a compound of the Formula Ia wherein $R^1$ or a substituent on Q is amino.

A suitable acylating agent is, for example, any agent known in the art for the acylation of amino to acylamino, for example an acyl halide, for example a (1-6C)alkanoyl chloride or bromide, conveniently in the presence of a suitable base, as defined hereinbefore, an alkanoic acid anhydride or mixed anhydride, for example a (1-6C)alkanoic acid anhydride such as acetic anhydride or the mixed anhydride formed by the reaction of an alkanoic acid and a (1-6C)alkoxycarbonyl halide, for example a (1-6C)alkoxycarbonyl chloride, in the presence of a suitable base as defined hereinbefore. In general the acylation is carried out in a suitable inert solvent or diluent as defined hereinbefore and at a temperature, in the range, for example, −30 to 120° C., conveniently at or near ambient temperature.

(f) A compound of the Formula Ia wherein $R^1$ or a substituent on Q is (1-6C)alkanesulphonylamino may be prepared by the reaction of a compound of the Formula Ia wherein $R^1$ or a substituent on Q is amino with a (1-6C)alkanesulphonic acid, or an activated derivative thereof.

A suitable activated derivative of a (1-6C)alkanesulphonic acid is, for example, an alkanesulphonyl halide, for example an alkanesulphonyl chloride formed by the reaction of the sulphonic acid and an inorganic acid chloride, for example thionyl chloride. The reaction is preferably carried out in the presence of a suitable base as defined hereinbefore, particularly pyridine, and in a suitable inert solvent or diluent as defined hereinbefore, particularly methylene chloride.

(g) A compound of the Formula Ia wherein $R^1$ or a substituent on Q is carboxy, carboxy-(1-6C)alkyl, carboxy-(1-6C)alkoxy, carboxy-(1-6C)alkylamino, N-(1-6C)alkyl-carboxy-(1-6C)alkylamino or carboxy-(2-6C)alkanoylamino may be prepared by the cleavage of a compound of the Formula Ia wherein $R^1$ or a substituent on Q is (1-6C)alkoxycarbonyl, (1-6C)alkoxycarbonyl-(1-6C)alkyl, (1-6C)alkoxycarbonyl-(1-6C)alkoxy, (1-6C)alkoxycarbonyl-(1-6C)alkylamino, N-(1-6C)alkyl-(1-6C)alkoxycarbonyl-(1-6C)alkylamino or (1-6C)alkoxycarbonyl-(2-6C)alkanoylamino as appropriate.

The cleavage reaction may conveniently be carried out by any of the many procedures known in the art for such a transformation. The reaction may be carried out, for example, by hydrolysis under acidic or basic conditions. A suitable base is, for example, an alkali metal, alkaline earth metal or ammonium carbonate or hydroxide, for example sodium carbonate, potassium carbonate, sodium hydroxide, potassium hydroxide or ammonium hydroxide. The reaction is preferably carried out in the presence of water and a suitable solvent or diluent such as methanol or ethanol. The reaction is conveniently carried out at a temperature in the range 10 to 150° C., preferably at or near ambient temperature.

(h) A compound of the Formula Ia wherein $R^1$ is amino-(1-6C)alkyl, (1-6C)alkylamino-(1-6C)alkyl, di-[(1-6C)alkyl]amino-(1-6C)alkyl or a heterocyclyl-(1-6C)alkyl group may be prepared by the reaction, conveniently in the presence of a suitable base as defined hereinbefore, of a compound of the Formula XIII

XIII

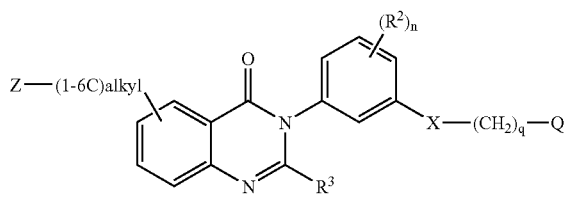

wherein X, $R^2$, $R^3$, n, q and Q have any of the meanings defined hereinbefore and Z is a suitable leaving group with an appropriate amine or heterocycle.

A suitable leaving group Z is, for example, a halogeno group such as fluoro, chloro or bromo, a (1-6C)alkanesulphonyloxy group such as methanesulphonyloxy or an arylsulphonyloxy group such as 4-toluenesulphonyloxy.

The reaction is conveniently carried out in the presence of a suitable inert diluent or, carrier as defined hereinbefore and at a temperature in the range, for example, 20 to 200° C., conveniently in the range 50 to 150° C.

The following biological assays and Examples serve to illustrate the present invention.

Biological Assays

The following assays can be used to measure the p38 kinase-inhibitory, the TNF-inhibitory and anti-arthritic effects of the compounds of the present invention:

In vitro Enzyme Assay

The ability of compounds of the invention to inhibit the enzyme p38 kinase was assessed. Activity of test compounds against each of the p38α and p38β isoforms of the enzyme was determined.

Human recombinant MKK6 (GenBank Accesion Number G1209672) was isolated from Image clone 45578 (*Genomics*, 1996, 33, 151) and utilised to produce protein in the form of a GST fusion protein in a pGEX vector using analogous procedures to those disclosed by J. Han et al., *Journal of Biological Chemistry* 1996, 271, 2886-2891. p38α (GenBank Accession Number G529039) and p38β (GenBank Accession Number G1469305) were isolated by PCR amplification of human lymphoblastoid cDNA (GenBank Accession Number GM1416) and human foetal brain cDNA [synthesised from mRNA (Clontech, catalogue no. 6525-1) using a Gibco superscript cDNA synthesis kit] respectively using oligonucleotides designed for the 5' and 3' ends of the human p38α and p38β genes using analogous procedures to those described by J. Han et al., *Biochimica et Biophysica Acta*, 1995, 1265, 224-227 and Y. Jiang et al., *Journal of Biological Chemistry*, 1996, 271, 17920-17926.

Both p38 protein isoforms were expressed in *e coli* in PET vectors. Human recombinant p38α and p38β isoforms were produced as 5' c-myc, 6H is tagged proteins. Both MKK6 and the p38 proteins were purified using standard protocols: the GST MKK6 was purified using a glutathione sepharose column and the p38 proteins were purified using nickel chelate columns.

The p38 enzymes were activated prior to use by incubation with MKK6 for 3 hours at 30° C. The unactivated *coli*-expressed MKK6 retained sufficient activity to fully activate both isoforms of p38. The activation incubate comprised p38α (10 μl of 10 mg/ml) or p38β (10 μl of 5 mg/ml) together with MKK6 (10 μl of 1 mg/ml), 'Kinase buffer' [100 μl; pH 7.4 buffer comprising Tris (50 mM), EGTA (0.1 mM), sodium orthovanadate (0.1 mM) and β-mercaptoethanol (0.1%)] and MgATP (30 μl of 50 mM Mg(OCOCH$_3$)$_2$ and 0.5 mM ATP). This produced enough activated p38 enzyme for 3 Microtiter plates.

Test compounds were solubilised in DMSO and 10 μl of a 1:10 diluted sample in 'Kinase Buffer' was added to a well in a Microtiter plate. For single dose testing, the compounds were tested at 10 μM. 'Kinase Assay Mix' [30 μl; comprising Myelin Basic Protein (Gibco BRL cat. no. 1322B-010; 1 ml of a 3.33 mg/ml solution in water), activated p38 enzyme (50 μl) and 'Kinase Buffer' (2 ml)] was then added followed by 'Labelled ATP' [10 μl; comprising 50 μM ATP, 0.1 μCi $^{33}$P ATP (Amersham International cat. no. BF1000) and 50 mM Mg(OCOCH$_3$)$_2$]. The plates were incubated at room temperature with gentle agitation. Plates containing p38α were incubated for 90 min and plates containing p38β were incubated for 45 min. Incubation was stopped by the addition of 50 μl of 20% trichloroacetic acid (TCA). The precipitated protein was phosphorylated by p38 kinase and test compounds were assessed for their ability to inhibit this phosphorylation. The plates were filtered using a Canberra Packard Unifilter and washed with 2% TCA, dried overnight and counted on a Top Count scintillation counter.

Test compounds were tested initially at a single dose and active compounds were retested to allow IC$_{50}$ values to be determined.

In vitro Cell-based Assays (i) PBMC

The ability of compounds of this invention to inhibit TNFα production was assessed by using human peripheral blood mononuclear cells which synthesise and secrete TNFα when stimulated with lipopolysaccharide.

Peripheral blood mononuclear cells (PBMC) were isolated from heparinised (10 units/ml heparin) human blood by density centrifugation (Lymphoprep™; Nycomed). Mononuclear cells were resuspended in culture medium [RPMI 1640 medium (Gibco) supplemented with 50 units/ml penicillin, 50 μg/ml streptomycin, 2mM glutamine and 1% heat-inactivated human AB serum (Sigma H-1513)]. Compounds were solubilised in DMSO at a concentration of 50 mM, diluted 1:100 in culture medium and subsequently serial dilutions were made in culture medium containing 1% DMSO. PBMCs (2.4×10$^5$ cells in 160 μl culture medium) were incubated with 20μl of varying concentrations of test compound (triplicate cultures) or 20 μl culture medium containing 1% DMSO (control wells) for 30 minutes at 37° C. in a humidified (5% CO$_2$/95% air) incubator (Falcon 3072; 96 well flat-bottom tissue culture plates). 20 μl lipopolysaccharide [LPS *E. Coli* 0111:B4 (Sigma L-4130), final concentration 10 μg/ml] solubilised in culture medium was added to appropriate wells. 20 μl culture medium was added to "medium alone" control wells. Six "LPS alone" and four "medium alone" controls were included on each 96 well plate. Varying concentrations of a known TNFα inhibitor were included in each test, i.e. an inhibitor of the PDE Type IV enzyme (for example see Semmler, J. Wachtel. H and Endres, S., *Int. J. Immunopharmac.* (1993), 15(3), 409-413) or an inhibitor of proTNFα convertase (for example, see McGeehan, G. M. et al. *Nature* (1994) 370, 558-561). Plates were incubated for 7 hours at 37° C. (humidified incubator) after which 100 μl of the supernatant was removed from each well and stored at −70° C. (96 well round-bottom plates; Corning 25850). TNFα levels were determined in each sample using a human TNFα ELISA (see WO92/10190 and *Current Protocols in Molecular Biology*, vol 2 by Frederick M. Ausbel et al., John Wiley and Sons Inc.).

$$\% \text{ inhibition} = \frac{(LPS \text{ alone} - \text{medium alone}) - (\text{test concentration} - \text{medium alone})}{(LPS \text{ alone} - \text{medium alone})} \times 100$$

(ii) Human Whole Blood

The ability of the compounds of this invention to inhibit TNFα production was also assessed in a human whole blood assay. Human whole blood secretes TNFα when stimulated with LPS. This property of blood forms the basis of an assay which is used as a secondary test for compounds which profile as active in the PBMC test.

Heparinised (10 units/ml) human blood was obtained from volunteers. 160 μl whole blood were added to 96 well round-bottom plates (Corning 25850). Compounds were solubilised and serially diluted in RPMI 1640 medium (Gibco) supplemented with 50 units/ml penicillin, 50 μg/ml streptomycin and 2 mM glutamine, as detailed above. 20 μl of each test concentration was added to appropriate wells (triplicate cultures). 20 μl of RPMI 1640 medium supplemented with antibiotics and glutamine was added to control wells. Plates were incubated for 30 minutes at 37° C. (humidified incubator), prior to addition of 20μl LPS (final concentration 10 μl g/ml). RPMI 1640 medium was added to control wells. Six "LPS alone" and four "medium alone" controls were included on each plate. A known TNFα synthesis/secretion inhibitor was included in each test. Plates were incubated for 6 hours at 37° C. (humidified incubator). Plates were centrifuged (2000 rpm for 10 minutes) and 100 μl plasma removed and stored at −70° C. (Corning 25850 plates). TNFα levels were measured by ELISA (see WO92/10190 and *Current Protocols in Molecular Biology*, vol 2 by Frederick M. Ausbel et al., John Wiley and Sons Inc.). The paired antibodies that were used in the ELIZA were obtained from R&D Systems (catalogue nos. MAB610 anti-human TNFα coating antibody, BAF210 biotinylated anti-human TNFα detect antibody).

Ex vivo/In vivo Assessment

The ability of the compounds of this invention as ex vivo TNFα inhibitors were assessed in the rat or mouse. Briefly, groups of male Wistar Alderley Park (AP) rats (180-210 g) were dosed with compound (6 rats) or drug vehicle (10 rats) by the appropriate route, for example peroral (p.o.), intraperitoneal (i.p.) or subcutaneous (s.c.). Ninety minutes later rats were sacrificed using a rising concentration of $CO_2$ and bled out via the posterior vena cavae into 5 Units of sodium heparin/ml blood. Blood samples were immediately placed on ice and centrifuged at 2000 rpm for 10 min at 4° C. and the harvested plasmas frozen at −20° C. for subsequent assay of their effect on TNFα production by LPS-stimulated human blood. The rat plasma samples were thawed and 175 μl of each sample was added to a set format pattern in a 96 well round bottom plate (Corning 25850). 50 μl of heparinized human blood was then added to each well, mixed and the plate was incubated for 30 min at 37° C. (humidified incubator). LPS (25 μl; final concentration 10 μg/ml) was added to the wells and incubation continued for a further 5.5 hours. Control wells were incubated with 25 μl of medium alone. Plates were then centrifuged for 10 min at 2000 rpm and 200 μl of the supernatants were transferred to a 96 well plate and frozen at −20° C. for subsequent analysis of TNF concentration by ELISA.

Data analysis by dedicated software calculates for each compound/dose:

$$\frac{\% \text{ inhibition}}{\text{of } TNF\alpha} = \frac{\text{Mean } TNF\alpha \text{ (Controls)} - \text{Mean } TNF\alpha \text{ (Treated)}}{\text{Mean } TNF\alpha \text{ (Controls)}} \times 100$$

Alternatively, mice could be used instead of rats in the above procedure.

Test as Anti-arthritic Agent

Activity of a compound as an anti-arthritic agent was tested as follows. Acid soluble native type II collagen was shown by Trentham et. al. [1] to be arthritogenic in rats; it caused polyarthritis when administered in Freunds incomplete adjuvant. This is now known as collagen-induced arthritis (CIA) and similar conditions can be induced in mice and primates. Recent studies have shown that anti-TNF monoclonal antibodies [2] and TNF receptor-IgG fusion proteins [3] ameliorate established CIA indicating that TNF plays a key role in the pathophysiology of CIA. Moreover, the remarkable efficacy reported for anti-TNF monoclonal antibodies in recent rheumatoid arthritis clinical trials indicates that TNF plays a major role in this chronic inflammatory disease. Thus CIA in DBA/1 mice as described in references 2 and 3 is a tertiary model which can be used to demonstrate the anti-arthritic activity of a compound. Also see reference 4.

1. Trentham, D. E. et al., (1977) *J. Exp. Med.*, 146 857.
2. Williams, R. O. et al., (1992) *Proc. Natl. Acad. Sci.*, 89, 9784.
3. Williams, R. O. et al., (1995) *Immunology*, 84, 433.
4. Badger, M. B. et al., (1996) *The Journal of Pharmacology and Experimental Therapeutics*, 279, 1453-1461.

Although the pharmacological properties of the compounds of the Formula Ia vary with structural change as expected, in general a compound of the Formula Ia gives over 30% inhibition of p38α and/or p38β at concentrations up to 10 μM. No physiologically unacceptable toxicity was observed at the effective dose for compounds tested of the present invention.

By way of example:
(i) 6-[N-(3-dimethylaminopropyl)-N-methylamino]-3-[2-methyl-5-(2-morpholinopyrid-4-ylcarbonylamino)phenyl]-3,4-dihydroquinazolin-4-one has an $IC_{50}$ of approximately 0.2 μM against p38α and an $IC_{50}$ of approximately 2 μM in the Human Whole Blood test;
(ii) 6-[N-(3-dimethylaminopropyl)-N-methylamino]-3-[5-(2-morpholinopyrid-4-ylcarbonylamino)phenyl]-3,4-dihydroquinazolin-4-one has an $IC_{50}$ of approximately 0.05 μM against p38α and an $IC_{50}$ of approximately 5 μM in the Human Whole Blood test; and
(iii) 8-[N-(3-dimethylaminopropyl)-N-methylamino]-3-[2-methyl-5-(2-morpholinopyrid-4-ylcarbonylamino)phenyl]-3,4-dihydroquinazolin-4-one has an $IC_{50}$ of approximately 0.1 μM against p38α and an $IC_{50}$ of approximately 7 μM in the Human Whole Blood test.

According to a further aspect of the invention there is provided a pharmaceutical composition which comprises an amide derivative of the Formula Ia or Ib, or a pharmaceutically-acceptable or in-vivo-cleavable ester thereof, as defined hereinbefore or an amide derivative selected from 3-(5-benzamido-2-methylphenyl)-2-methyl-3,4-dihydroquinazolin-4-one, 3-[5-(4-methylbenzamido)-2-methylphenyl]-2-methyl-3,4-dihydroquinazolin-4-one and 3-[5-(4-methoxybenzamido)-2-methylphenyl]-2-methyl-3,4- dihydroquinazolin-4-one in association with a pharmaceutically-acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent compounded with an appropriate and convenient amount of excipients which may vary from about 5 to about 98 percent by weight of the total composition.

The size of the dose for therapeutic or prophylactic purposes of a compound of the Formula Ia will naturally vary according to the nature and severity of the conditions, the age and sex of the animal or patient and the route of administration, according to well known principles of medicine.

In using a compound of the Formula Ia for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used. Oral administration is however preferred, particularly in tablet form. Typically, unit dosage forms will contain about 1 mg to 500 mg of a compound of this invention.

According to a further aspect of the invention there is provided an amide derivative of the Formula Ia, or a pharmaceutically-acceptable salt or in-vivo-cleavable ester thereof, as defined hereinbefore for use in a method of treatment of the human or animal body by therapy.

According to a further aspect of the invention there is provided the use of an amide derivative of the Formula Ia or Ib, or a pharmaceutically-acceptable salt or in-vivo-cleavable ester thereof, as defined hereinbefore or an amide derivative selected from 3-(5-benzamido-2-methylphenyl)-2-methyl-3,4-dihydroquinazolin-4-one, 3-[5-(4-methylbenzamido)-2-methylphenyl]-2-methyl-3,4-dihydroquinazolin-4-one and 3-[5-(4-methoxybenzamido)-2-methylphenyl]-2-methyl-3,4-dihydroquinazolin-4-one in the manufacture of a medicament for use in the treatment of diseases or medical conditions mediated by cytokines.

In a further aspect the present invention provides a method of treating diseases or medical conditions mediated by cytokines which comprises administering to a warm-blooded animal an effective amount of an amide derivative of the Formula Ia or Ib, or a pharmaceutically-acceptable salt or in-vivo-cleavable ester thereof, as defined hereinbefore or of an amide derivative selected from 3-(5-benzamido-2-methylphenyl)-2-methyl-3,4-dihydroquinazolin-4-one, 3-[5-(4-methylbenzamido)-2-methylphenyl]-2-methyl-3,4-dihydroquinazolin-4-one and 3-[5-(4-methoxybenzamido)-2-methylphenyl]-2-methyl-3,4-dihydroquinazolin-4-one.

In a further aspect the present invention provides the use of an amide derivative of the Formula Ia, or a pharmaceutically-acceptable salt or in-vivo-cleavable ester thereof, as defined hereinbefore or an amide derivative selected from 3-(5-benzamido-2-methylphenyl)-2-methyl-3,4-dihydroquinazolin-4-one, 3-[5-(4-methylbenzamido)-2-methylphenyl]-2-methyl-3,4-dihydroquinazolin-4-one and 3-[5-(4-methoxybenzamido)-2-methylphenyl]-2-methyl-3,4-dihydroquinazolin-4-one in the manufacture of a medicament for use in the treatment of diseases or medical conditions mediated by TNF, IL-1, IL-6 or IL-8.

In a further aspect the present invention provides a method of treating diseases or medical conditions mediated by TNF, IL-1, IL-6 or IL-8 which comprises administering to a warm-blooded animal an effective amount of an amide derivative of the Formula Ia or Ib, or a pharmaceutically-acceptable salt or in-vivo-cleavable ester thereof, as defined hereinbefore or of an amide derivative selected from 3-(5-benzamido-2-methylphenyl)-2-methyl-3,4-dihydroquinazolin-4-one, 3-[5-(4-methylbenzamido)-2-methylphenyl]-2-methyl-3,4-dihydroquinazolin-4-one and 3-[5-(4-methoxybenzamido)-2-methylphenyl]-2-methyl-3,4-dihydroquinazolin-4-one.

In a further aspect the present invention provides the use of an amide derivative of the Formula Ia, or a pharmaceutically-acceptable salt or in-vivo-cleavable ester thereof, as defined hereinbefore or an amide derivative selected from 3-(5-benzamido-2-methylphenyl)-2-methyl-3,4-dihydroquinazolin-4-one, 3-[5-(4-methylbenzamido)-2-methylphenyl]-2-methyl-3,4-dihydroquinazolin-4-one and 3-[5-(4-methoxybenzamido)-2-methylphenyl]-2-methyl-3,4-dihydroquinazolin-4one in the manufacture of a medicament for use in the treatment of diseases or medical conditions mediated by TNF.

In a further aspect the present invention provides a method of treating diseases or medical conditions mediated by TNF which comprises administering to a warm-blooded animal an effective amount of an amide derivative of the Formula Ia, or a pharmaceutically-acceptable salt or in-vivo-cleavable ester thereof, as defined hereinbefore or of an amide derivative selected from 3-(5-benzamido-2-methylphenyl)-2-methyl-3,4-dihydroquinazolin-4-one, 3-[5-(4-methylbenzamido)-2-methylphenyl]-2-methyl-3,4-dihydroquinazolin-4-one and 3-[5-(4-methoxybenzamido)-2-methylphenyl]-2-methyl-3,4-dihydroquinazolin-4-one.

In a further aspect the present invention provides the use of an amide derivative of the Formula Ia, or a pharmaceutically-acceptable salt or in-vivo-cleavable ester thereof, or an amide derivative selected from 3-(5-benzamido-2-methylphenyl)-2-methyl-3,4-dihydroquinazolin-4-one, 3-[5-(4-methylbenzamido)-2-methylphenyl]-2-methyl-3,4-dihydroquinazolin-4-one and 3-[5-(4-methoxybenzamido)-2-methylphenyl]-2-methyl-3,4-dihydroquinazolin-4-one as defined hereinbefore in the manufacture of a medicament for use in inhibiting TNF, IL-1, IL-6 or IL-8.

In a further aspect the present invention provides a method of inhibiting TNF, IL-1, IL-6 or IL-8 which comprises administering to a warm-blooded animal an effective amount of an amide derivative of the Formula Ia, or a pharmaceutically-acceptable salt or in-vivo-cleavable ester thereof, as defined hereinbefore or of an amide derivative selected from 3-(5-benzamido-2-methylphenyl)-2-methyl-3,4-dihydroquinazolin-4-one, 3-[5-(4-methylbenzamido)-2-methylphenyl]-2-methyl-3,4-dihydroquinazolin-4-one and 3-[5-(4-methoxybenzamido)-2-methylphenyl]-2-methyl-3,4-dihydroquinazolin-4-one.

In a further aspect the present invention provides the use of an amide derivative of the Formula Ia, or a pharmaceutically-acceptable salt or in-vivo-cleavable ester thereof, as defined hereinbefore or an amide derivative selected from 3-(5-benzamido-2-methylphenyl)-2-methyl-3,4-dihydroquinazolin-4-one, 3-[5-(4-methylbenzamido)-2-methylphenyl]-2-methyl-3,4-dihydroquinazolin-4-one and 3-[5-4-methoxybenzamido)-2-methylphenyl]-2-methyl-3,4-dihydroquinazolin-4-one in the manufacture of a medicament for use in inhibiting TNF.

In a further aspect the present invention provides a method of inhibiting TNF which comprises administering to a warm-blooded animal an effective amount of an amide derivative of the Formula Ia, or a pharmaceutically-acceptable salt or in vivo-cleavable ester thereof, as defined hereinbefore or of an amide derivative selected from 3-(5-benzamido-2-methylphenyl)-2-methyl-3,4-dihydroquinazolin-4-one, 3-[5-(4-methylbenzamido)-2-methylphenyl]-2-methyl-3,4-dihydroquinazolin-4-one and 3-[5-(4-methoxybenzamido)-2-methylphenyl]-2-methyl-3,4-dihydroquinazolin-4-one.

In a further aspect the present invention provides the use of an amide derivative of the Formula Ia, or a pharmaceutically-acceptable salt or in-vivo-cleavable ester thereof, as defined hereinbefore or an amide derivative selected from 3-(5-benzamido-2-methylphenyl)-2-methyl-3,4-dihydroquinazolin-4-one, 3-[5-(4-methylbenzamido)-2-methylphenyl]-2-methyl-3,4dihydroquinazolin-4-one and 3-[5-(4-methoxybenzamido)-2-methylphenyl]-2-methyl-3,4-dihydroquinazolin-4-one in the manufacture of a medicament for use in the treatment of diseases or medical conditions mediated by p38 kinase.

In a further aspect the present invention provides a method of treating diseases or medical conditions mediated by p38 kinase which comprises administering to a warm-blooded animal an effective amount of an amide derivative of the Formula Ia, or a pharmaceutically-acceptable salt or in-vivo-cleavable ester thereof, as defined hereinbefore or of an amide derivative selected from 3-(5-benzamido-2-methylphenyl)-2-methyl-3,4-dihydroquinazolin-4-one, 3-[5-(4-methylbenzamido)-2-methylphenyl]-2-methyl-3,4-dihydroquinazolin-4-one and 3-[5-(4-methoxybenzamido)-2-methylphenyl]-2-methyl-3,4-dihydroquinazolin-4-one.

In a further aspect the present invention provides the use of an amide derivative of the Formula Ia, or a pharmaceutically-acceptable salt or in-vivo-cleavable ester thereof, or an amide derivative selected from 3-(5-benzamido-2-methylphenyl)-2-methyl-3,4-dihydroquinazolin-4-one, 3-[5-(4-methylbenzamido)-2-methylphenyl]-2-methyl-3,4-dihydroquinazolin-4-one and 3-[5-(4-methoxybenzamido)-2-methylphenyl]-2-methyl-3,4-dihydroquinazolin-4-one in the manufacture of a medicament for use in the production of a p38 kinase inhibitory effect.

In a further aspect the present invention provides a method of providing a p38 kinase inhibitory effect which comprises administering to a warm-blooded animal an effective amount of an amide derivative of the Formula Ia, or a pharmaceutically-acceptable salt or in-vivo-cleavable ester thereof, as defined hereinbefore or of an amide derivative selected from 3-(5-benzamido-2-methylphenyl)-2-methyl-3,4-dihydroquinazolin-4-one, 3-[5-(4-methylbenzamido)-2-methylphenyl]-2-methyl 3,4-dihydroquinazolin-4-one and 3-[5-(4-methoxybenzamido)-2-methylphenyl]-2-methyl-3,4-dihydroquinazolin-4-one.

In a further aspect the present invention provides the use of an amide derivative of the Formula Ia, or a pharmaceutically-acceptable salt or in-vivo-cleavable ester thereof, as defined hereinbefore or an amide derivative selected from 3-(5-benzamido-2-methylphenyl)-2-methyl-3,4-dihydroquinazolin-4-one, 3-[5-(4-methylbenzamido)-2-methylphenyl]-2-methyl-3,4-dihydroquinazolin-4-one and 3-[5-(4-methoxybenzamido)-2-methylphenyl]-2-methyl-3,4-dihydroquinazolin-4-one in the manufacture of a medicament for use in the treatment of rheumatoid arthritis, asthma, irritable bowel disease, multiple sclerosis, AIDS, septic shock, ischaemic heart disease or psoriasis.

In a further aspect the present invention provides a method of treating rheumatoid arthritis, asthma, irritable bowel disease, multiple sclerosis, AIDS, septic shock, ischaemic heart disease or psoriasis which comprises administering to a warm-blooded animal an effective amount of an amide derivative of the Formula Ia, or a pharmaceutically-acceptable salt or in-vivo-cleavable ester thereof, as defined hereinbefore or of an amide derivative selected from 3-(5-benzamido-2-methylphenyl)-2-methyl-3,4-dihydroquinazolin-4-one, 3-[5-(4-methylbenzamido)-2-methylphenyl]-2-methyl-3,4-dihydroquinazolin-4-one and 3-[5-(4-methoxybenzamido)-2-methylphenyl]-2-methyl-3,4-dihydroquinazolin-4-one.

The compounds of this invention may be used in combination with other drugs and therapies used in the treatment of disease states which would benefit from the inhibition of cytokines, in particular TNF and IL-1. For example, the compounds of the Formula Ia could be used in combination with drugs and therapies used in the treatment of rheumatoid arthritis, asthma, irritable bowel disease, multiple sclerosis, AIDS, septic shock, ischaemic heart disease, psoriasis and the other disease states mentioned earlier in this specification.

For example, by virtue of their ability to inhibit cytokines, the compounds of the Formula Ia are of value in the treatment of certain inflammatory and non-inflammatory diseases which are currently treated with a cyclooxygenase-inhibitory non-steroidal anti-inflammatory drug (NSAID) such as indomethacin, ketorolac, acetylsalicyclic acid, ibuprofen, sulindac, tolmetin and piroxicam. Co-administration of a compound of the Formula I with a NSAID can result in a reduction of the quantity of the latter agent needed to produce a therapeutic effect. Thereby the likelihood of adverse side-effects from the NSAID such as gastrointestinal effects are reduced. Thus according to a further feature of the invention there is provided a pharmaceutical composition which comprises an amide derivative of the Formula Ia, or a pharmaceutically-acceptable salt or in-vivo-cleavable ester thereof, in conjunction or admixture with a cyclooxygenase inhibitory non-steroidal anti-inflammatory agent, and a pharmaceutically-acceptable diluent or carrier.

The compounds of the invention may also be used with anti-inflammatory agents such as an inhibitor of the enzyme 5-lipoxygenase.

The compounds of the Formula Ia may also be used in the treatment of conditions such as rheumatoid arthritis in combination with antiarthritic agents such as gold, methotrexate, steroids and penicillinamine, and in conditions such as osteoarthritis in combination with steroids.

The compounds of the present invention may also be administered in degradative diseases, for example osteoarthritis, with chondroprotective, anti-degradative and/or reparative agents such as Diacerhein, hyaluronic acid formulations such as Hyalan, Rumalon, Arteparon and glucosamine salts such as Antril.

The compounds of the Formula Ia may be be used in the treatment of asthma in combination with antiasthmatic agents such as bronchodilators and leukotriene antagonists.

If formulated as a fixed dose such combination products employ the compounds of this invention within the dosage range described herein and the other pharmaceutically-active agent within its approved dosage range. Sequential use is contemplated when a combination formulation is inappropriate.

Although the compounds of the Formula Ia are primarily of value as therapeutic agents for use in warm-blooded animals (including man), they are also useful whenever it is required to inhibit the effects of cytokines. Thus, they are useful as pharmacological standards for use in the development of new biological tests and in the search for new pharmacological agents.

The invention will now be illustrated in the following non-limiting Examples in which, unless otherwise stated:

(i) operations were carried out at ambient temperature, i.e. in the range 17 to 25° C. and under an atmosphere of an inert gas such as argon unless otherwise stated;

(ii) evaporations were carried out by rotary evaporation in vacuo and work-up procedures were carried out after removal of residual solids by filtration;:

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, Germany or high pressure liquid chromatography (HPLC) was performed on C18 reverse phase silica, for example on a Dynamax C-18 60 Å preparative reversed-phase column;

(iv) yields are given for illustration only and are not necessarily the maximum attainable;

(v) in general, the end-products of the Formula Ia have satisfactory microanalyses and their structures were confirmed by nuclear magnetic resonance (NMR) and/or mass spectral techniques; fast-atom bombardment (FAB) mass spectral data were obtained using a Platform spectrometer and, where appropriate, either positive ion data or negative ion data were collected; NMR chemical shift values were measured on the delta scale [proton magnetic resonance spectra were determined using a Varian Gemini 2000 spectrometer operating at a field strength of 300 MHz or a Bruker AM250 spectrometer operating at a field strength of 250 MHz]; the following abbreviations have been used: s, singlet; d, doublet; t, triplet; m, multiplet; br, broad;

(vi) intermediates were not generally fully characterised and purity was assessed by thin layer chromatographic, HPLC, infra-red (IR) and/or NMR analysis;

(vii) melting points are uncorrected and were determined using a Mettler SP62 automatic melting point apparatus or an oil-bath apparatus; melting points for the end-products of the Formula Ia were determined after crystallisation from a conventional organic solvent such as ethanol, methanol, acetone, ether or hexane, alone or in admixture; and (viii) the following abbreviations have been used:-
DMF N,N-dimethylformamide
DMSO dimethylsulphoxide.

EXAMPLE 1

3-(5-benzamido-2-chlorophenyl)-7-methoxy-3,4-dihydroquinazolin-4-one

Triethyl orthoformate (0.189 ml) was added to a stirred mixture of N-(5-benzamido-2-chlorophenyl)-2-amino-4-methoxybenzamide (0.15 g), ethanol (10 ml) and glacial acetic acid (0.022 ml) and the resultant mixture was heated to 70° C. for 16 hours. The mixture was evaporated. The residue was partitioned between methylene chloride and a saturated aqueous solution of sodium bicarbonate. The organic phase was dried (MgSO$_4$) and evaporated and the residue was triturated under a mixture of ethyl acetate and diethyl ether. The material so obtained was further purified by column chromatography on an ion exchange column (isolute SCX column from International Sorbent Technology Limited, Hengoed, Mid-Glamorgan, UK) using initially methanol and then a 99:1 mixture of methanol and a saturated aqueous ammonium hydroxide solution as eluent. There was thus obtained the title compound (0.054 g); NMR Spectrum: (DMSOd$_6$) 3.92 (s, 3H), 7.12-7.22 (m, 2H), 7.48-7.6 (m, 3H), 7.68 (d, 1H), 7.88-8.0 (m, 3H), 8.04-8.12 (m, 2H), 8.28 (m, 1H), 10.06 (s, 1H); Mass Spectrum: M+H$^+$ 406 and 408.

The N-(5-benzamido-2-chlorophenyl)-2-amino-4-methoxybenzamide used as a starting material was prepared as follows:

Benzoyl chloride (5.2 ml) was added to a stirred mixture of 2,4-diaminochlorobenzene (6.42 g), triethylamine (12.5 ml) and methylene chloride (100 ml) which had been cooled to 0° C. The mixture was allowed to warm to ambient temperature and was stirred for 16 hours. The mixture was evaporated and the residue was triturated under a saturated aqueous sodium bicarbonate solution. The resultant solid was isolated, washed in turn with water and isohexane and dried under vacuum at 55° C. There was thus obtained N-3-amino-4-chlorophenyl)benzamide as a solid (10.38 g); NMR Spectrum: (DMSOd$_6$) 5.32 (s, 2H), 6.9 (m, 1H), 7.1 (d, 1H), 7.37 (d, 1H), 7.52 (m, 3H), 7.9 (d, 2H), 10.05 (s, 1H).

Oxalyl chloride (0.781 ml) was added dropwise to a stirred mixture of 4-methoxy-2-nitrobenzoic acid (1.6 g), DMF (a few drops) and methylene chloride (30 ml) which had been cooled to 0° C. The mixture was allowed to warm to ambient temperature and was stirred for 4 hours. The mixture was evaporated. The residue was dissolved in methylene chloride (10 ml) and added dropwise to a stirred mixture of N-(3-amino-4-chlorophenyl)benzamide (2.0 g) triethylamine (2.49 ml) and methylene chloride (30 ml). The resultant mixture was stirred at ambient temperature for 16 hours. The precipitate was isolated, washed with 1N aqueous hydrochloric acid solution and with methanol and dried under vacuum at 40° C. There was thus obtained N-(5-benzamido-2-chlorophenyl)-4-methoxy-2-nitrobenzamide (2.49 g); NMR Spectrum: (DMSOd$_6$) 3.9 (s, 3H), 7.39 (d, 1H), 7.47-7.62 (m, 5H), 7.72 (d, 1H), 7.78 (d, 1H), 7.97 (d, 2H), 8.14 (s,1H), 10.28 (s, 1H), 10.46 (s, 1H);. Mass Spectrum: M+H$^+$ 426 and 428.

Iron powder (2.79 g) was added to a stirred suspension of a portion (2.13 g) of the material so obtained in a mixture of ethanol (100 ml), water (20 ml) and acetic acid (4 ml). The mixture was stirred and heated to reflux for 6 hours. The mixture was cooled to ambient temperature. Water (50 ml) was added and the resultant mixture was basified by the addition of sodium carbonate. The mixture was filtered and the filtrate was evaporated. The residue was triturated under water. The resultant solid was isolated and dried under vacuum at 40° C. There was thus obtained the required starting material (0.911 g); NMR Spectrum: (DMSOd$_6$) 3.72 (s, 3H), 6.09 (d, 1H), 6.27 (s, 1H), 6.62 (s, 2H), 7.45-7.61 (m, 4H), 7.66-7.72 (m, 2H), 7.95 (d, 2H), 8.07 (s, 1H), 9.52 (s, 1H), 10.37 (s, 1H);. Mass Spectrum: M+H$^+$ 396 and 398.

EXAMPLE 2

3-(5-benzamido-2-chlorophenyl)-7-methoxy-2-methyl-3,4-dihydroquinazolin-4-one Using an analogous procedure to that described in Example 1, triethyl orthoacetate was reacted with N-(5-benzamido-2-chlorophenyl)-2-amino-4-methoxybenzamide. The material so obtained was purified by column chromatography on an isolute SCX ion exchange column using initially methanol and then a 99:1 mixture of methanol and a saturated aqueous ammonium hydroxide solution as eluent. There was thus obtained the title compound in 27% yield; NMR Spectrum: (DMSOd$_6$) 2.15 (s, 3H), 3.91 (s, 3H), 7.09-7.14 (m, 2H), 7.46-7.6 (m, 3H), 7.71 (d, 1H), 7.87-8.06 (m, 5H), 10.57 (s, 1H); Mass Spectrum: M+H$^+$ 420 and 422.

EXAMPLE 3

Using an analogous procedure to that described in Example 1 or Example 2 as appropriate, the appropriate 2-aminobenzamide was reacted with triethyl orthoformate or triethyl orthoacetate to give the compounds described in Table I:

obtained 2-chloro-N-(4-methyl-3-nitrophenyl)pyridine-4-carboxamide (10.2 g). The organic filtrate was washed with a saturated aqueous sodium bicarbonate solution, dried (MgSO$_4$) and evaporated. The residue was triturated under methylene chloride and the resultant solid was isolated and dried under vacuum at 40° C. There was thus obtained a second crop (8.13 g) of 2-chloro-N-(4-methyl-3-nitrophenyl)pyridine-4-carboxamide; NMR Spectrum: (DMSOd$_6$) 2.48 (s, 3H), 7.51 (d, 1H), 7.86 (m, 1H), 7.96 (m, 2H), 8.49 (m, 1H), 8.64 (m, 1H), 10.85 (s, 1H); Mass Spectrum: M+H$^+$ 292 and 294.

A mixture of the pyridine-4-carboxamide so produced and morpholine (250 ml) was stirred and heated to 100° C. for 18 hours. The mixture was poured into water (250 ml) and stirred for 10 minutes. Methylene chloride (30 ml) was added and the resultant mixture was stirred for 30 minutes. The resultant solid was isolated, washed with methylene chloride and dried in a vacuum oven at 40° C. for 18 hours. There was thus obtained N-(4-methyl-3-nitrophenyl)-2-morpholinopyridine-4-carboxamide (17.34 g); NMR Spectrum: (DMSOd$_6$) 2.48 (s, 3H), 3.52 (m, 4H), 3.71 (m, 4H), 7.1 (d, 1H), 7.25 (s, 1H), 7.49 (d, 1H) 7.97 (m, 1H), 8.29 (m, 1H), 8.49 (m, 1H), 10.62 (s, 1H); Mass Spectrum: M+H$^+$ 343.

TABLE I

| No. | (R$^1$)$_m$ | (R$^2$)$_n$ | R$^3$ | Note |
|-----|-------------|-------------|-------|------|
| 1 | 6-[N-(3-dimethylaminopropyl)-N-methylamino] | 6-methyl | hydrogen | a |
| 2 | 6-[N-(3-dimethylaminopropyl)-N-methylamino] | 6-methyl | methyl | b |
| 3 | 6-[N-(3-dimethylaminopropyl)-N-methylamino] | hydrogen | hydrogen | c |
| 4 | 6-[N-(3-dimethylaminopropyl)-N-methylamino] | hydrogen | methyl | d |
| 5 | 6-(4-methylpiperazin-1-yl) | 6-methyl | hydrogen | e |
| 6 | 6-(4-methylpiperazin-1-yl) | 6-methyl | methyl | f |
| 7 | 6-(4-methylpiperazin-1-yl) | hydrogen | hydrogen | g |
| 8 | 6-(4-methylpiperazin-1-yl) | hydrogen | methyl | h |
| 9 | 8-[N-(3-dimethylaminopropyl)-N-methylamino] | 6-methyl | hydrogen | i |
| 10 | 6-[N-(3-methylaminopropyl)-N-methylamino] | 6-methyl | hydrogen | j |

Notes
a) The product gave the following data: NMR Spectrum: (DMSOd$_6$) 1.73-1.83 (m, 2H), 1.88 (s, 3H), 2.23 (s, 6H), 2.26-2.34 (m, 2H), 3.07 (s, 3H), 3.44-3.55 (m, 6H) 3.67-3.71 (m, 4H), 7.0 (d, 1H), 7.09 (s, 1H), 7.31 (d, 1H), 7.43 (s, 1H), 7.54 (s, 1H), 7.66 (d, 1H), 7.75 (d, 2H), 8.23 (d, 1H), 8.69 (s, 1H); Mass Spectrum: M+H$^+$ 556.

The N-[2-methyl-5-(2-morpholinopyrid-4-ylcarbonylamino)phenyl]-2-amino-5-[N-(3-dimethylaminopropyl)-N-methylamino]benzamide used as a starting material was prepared as follows:-

Triethylamine (31.8 ml) was added to a stirred mixture of 4-methyl-3-nitroaniline (15.8 g), 2-chloropyridine-4-carbonyl chloride (20 g) and methylene chloride (1 liter) and the resultant mixture was stirred at ambient temperature for 16 hours. The precipitate was isolated, washed with a saturated aqueous sodium bicarbonate solution and with methylene chloride and dried under vacuum at 40° C. There was thus A mixture of a portion (8.5 g) of the material so obtained, 5% palladium-on-carbon catalyst (0.85 g) and methanol (600 ml) was stirred under an atmosphere pressure of hydrogen gas for 18 hours. Methylene chloride (400 ml) was added and the reaction mixture was filtered through diatomaceous earth. The filtrate was evaporated to give N-(3-amino-4-methylphenyl)-2-morpholinopyridine-4-carboxamide (6.41 g); NMR Spectrum: (DMSOd$_6$) 2.01 (s, 3H), 3.52 (m, 4H), 3.73 (m, 4H), 4.83 (s, 2H), 6.78 (d, 1H), 6.84 (d, 1H) 7.04-7.08 (m, 2H), 7.2 (s, 1H), 8.24 (d, 1H), 9.95 (s, 1H); Mass Spectrum: M+H$^+$ 313.

Oxalyl chloride (0.55 g) was added dropwise to a stirred mixture of 5-chloro-2-nitrobenzoic acid (0.726 g), DMF (a few drops) and methylene chloride (25 ml) which had been cooled to 0° C. The mixture was allowed to warm to ambient temperature and was stirred for 5 hours. The mixture was evaporated. The residue was dissolved in methylene chloride (10 ml) and was added dropwise to a stirred mixture of N-(3- amino-4-methylphenyl)-2-morpholinopyridine-4-carboxamide (0.933 g), triethylamine (1.12 ml) and methylene chloride (25 ml). The mixture was stirred at ambient temperature for 16 hours. The resultant precipitate was isolated, washed in turn with water, methylene chloride and diethyl ether and dried under vacuum at 40° C. There was thus obtained N-[2-methyl-5-(2-morpholinopyrid-4-ylcarbonylamino)phenyl]-5-chloro-2-nitrobenzamide (1.12 g); NMR Spectrum: (DMSOd$_6$) 2.23 (s, 3H), 3.5-3.54 (m, 4H), 3.69-3.73 (m, 4H), 7.12 (d, 1H), 7.2-7.25 (m, 2H), 7.58 (d, 1H), 7.81 (d, 1H), 7.87-7.9 (m, 2H), 8.15 (d, 1H), 8.26 (d, 1H); Mass Spectrum: M+H$^+$ 496 and 498.

A mixture of a portion (0.2 g) of the material so obtained and N-(3-dimethylaminopropyl)-N-methylamine (1.5 ml) was stirred and heated to 100° C. for 16 hours. The mixture was cooled and poured into water. The resultant precipitate was isolated, washed in turn with water and diethyl ether and dried under vacuum at 40° C. There was thus obtained N-[2-methyl-5-(2-morpholinopyrid-4-ylcarbonylamino)phenyl]-5-[N-(3-dimethylaminopropyl)-N-methylamino]-2-nitrobenzamide (0.223 g); NMR Spectrum: (DMSOd$_6$) 1.62-1.74 (m, 2H), 2.12 (s, 6H), 2.18-2.26 (m, 5H), 3.08 (s, 3H), 3.50-3.54 (m, 6H), 3.69-3.71 (m, 4H), 6.75 (s, 1H), 6.84 (s, 1H), 7.12 (d, 1H), 7.2 (d, 1H), 7.26 (s, 1H), 7.68 (d, 1H), 7.9 (s, 1H), 8.04 (d, 1H), 8.26 (d, 1H), 9.82 (s, 1H), 10.04 (s, 1H); Mass Spectrum: M+H$^+$ 576.

A mixture of the material so obtained, 10% palladium-on-carbon (0.02 g) and methanol (15 ml) was stirred under an atmosphere of hydrogen gas. After cessation of hydrogen uptake, the catalyst was removed by filtration through diatomaceous earth and the filtrate was evaporated. There was thus obtained the required starting material (0.15 g); Mass Spectrum: M+H$^+$ 546.

a) The product gave the following data: NMR Spectrum: (DMSOd$_6$) 1.58-1.7 (m, 2H), 1.97 (s, 3H), 2.06 (s, 3H), 2.12 (s, 6H), 2.23 (t, 2H), 2.96 (s, 3H), 3.39-3.48 (m, 2H), 3.48-3.52 (m, 4H), 3.68-3.71 (m, 4H), 7.08 (d, 1H), 7.15 (s, 1H), 7.22 (s, 1H), 7.32 (m, 1H), 7.42 (d, 1H), 7.51 (d, 1H), 7.67 (s, 1H), 7.74 (d, 1H), 8.26 (d. 1H), 10.42 (s, 1H); Mass Spectrum: M+H$^+$ 570.

b) The product gave the following data: NMR Spectrum: (DMSOd$_6$) 1.66 (m, 2H), 2.12 (s, 6H), 2.22 (m, 2H), 2.99 (s, 3H), 3.51 (m, 6H), 3.71 (t, 4H), 7.1 (d, 1H), 7.24 (m, 3H), 7.35 (m, 1H), 7.55 (m, 2H), 7.85 (m, 2H), 8.05 (s, 1H), 8.27 (d, 1H), 10.51 (broad s, 1H); Mass Spectrum M+H$^+$ 542.

The N-[3-(2-morpholinopyrid-4-ylcarbonylamino)phenyl]-2-amino-5-[N-(3-dimethylaminopropyl)-N-methylamino]benzamide used as a starting material was prepared as follows:-

Triethylamine (6.7 ml) was added to a stirred mixture of 3-nitroaniline (3 g), 2-chloropyridine-4-carbonyl chloride (4.6 g) and methylene chloride (50 ml) and the resultant mixture was stirred at ambient temperature for 40 hours. The mixture was evaporated and the residue was triturated under water. The solid so obtained was isolated, washed with a saturated aqueous sodium bicarbonate solution and dried under vacuum at 55° C. There was thus obtained 2-chloro-N-(3-nitrophenyl)pyridine-4-carboxamide (6.03 g); NMR Spectrum: (DMSOd$_6$) 7.68 (t, 1H), 7.88 (t, 1H), 7.99 (m, 2H), 8.16 (d, 1H), 8.63 (d, 1H), 8.73 (t, 1H), 10.95 (broad s, 1H); Mass Spectrum: M+H$^+$ 278.

A mixture of the pyridine-4-carboxamide so produced and morpholine (100 ml) was stirred and heated to 130° C. for 3.5 hours and to 150° C. for 2 hours. The mixture was poured into water (250 ml) and stirred for 10 minutes. The resultant solid was isolated, washed in turn with water and with isohexane and dried under vacuum at 55° C. There was thus obtained N-(3-nitrophenyl)-2-morpholinopyridine-4-carboxamide (6.8 g); NMR Spectrum: (DMSOd$_6$) 3.52 (t, 4H), 3.71 (t, 4H), 7.12 (d, 1H), 7.25 (s, 1H), 7.66 (t, 1H), 7.97 (d, 1H), 8.15 (d, 1H), 8.29 (d, 1H), 8.73 (t, 1H), 10.72 (broad s, 1H); Mass Spectrum: M+H$^+$ 329.

A mixture of the material so obtained, 10% palladium-on-carbon catalyst (0.68 g), ammonium formate (13 g) and methanol (150 ml) was stirred and heated to reflux for 2 hours. The reaction mixture was filtered through diatomaceous earth. The filtrate was evaporated and the residue was triturated under water. The resultant solid was isolated, washed in turn with water and with isohexane and dried under vacuum at 55° C. There was thus obtained N-(3-aminophenyl)-2-morpholinopyridine-4-carboxamide (5.38 g); NMR Spectrum: (DMSOd$_6$) 3.51 (t, 4H), 3.71 (t, 4H), 5.07 (broad s, 2H), 6.33 (d, 1H), 6.81 (d, 1H), 6.95 (t, 1H), 7.05 (m, 2H), 7.2 (s, 1H), 8.24 (d, 1H), 9.96 (broad s, 1H); Mass Spectrum: M+H$^+$ 299.

Oxalyl chloride (0.66 ml) was added dropwise to a stirred mixture of 5-chloro-2-nitrobenzoic acid (1.22 g), DMF (a few drops) and methylene chloride (20 ml). The mixture was stirred at ambient temperature for 4 hours. The mixture was evaporated. The residue was dissolved in methylene chloride (10 ml) and was added to a stirred mixture of N-(3-aminophenyl)-2-morpholinopyridine-4-carboxamide (1.5 g), triethylamine (1.75 ml) and methylene chloride (20 ml). The mixture was stirred at ambient temperature for 16 hours. The mixture was evaporated and the residue was triturated under water. The solid so obtained was isolated, washed in turn with 2N aqueous sodium hydroxide solution and with diethyl ether. The material so obtained was purified on a SCX isolute ion exchange column using initially methanol and then a 99:1 mixture of methanol and a saturated aqueous ammonium hydroxide solution as eluent. There was thus obtained N-[3-(2-morpholinopyrid-4-ylcarbonylamino)phenyl]-5-chloro-2-nitrobenzamide (1.96 g); NMR Spectrum: (DMSOd$_6$) 3.51 (t, 4H), 3.71 (t, 4H), 7.1 (d, 1H), 7.23 (s, 1H), 7.36 (m, 2H), 7.51 (d, 1H), 7.82 (d, 1H), 7.93 (s, 1H), 8.18 (m, 2H), 8.26 (d, 1H), 10.37 (broad s, 1H), 10.73 (broad s, 1H); Mass Spectrum: M+H$^+$ 482.

A mixture of a portion (0.384 g) of the material so obtained and N-(3-dimethylaminopropyl)-N-methylamine (4 ml) was stirred and heated to 120° C. for 4 hours. The mixture was cooled and poured into a mixture of ice and water. The resultant precipitate was isolated, washed with isohexane and dried under vacuum at 55° C. There was thus obtained N-[3-(2-morpholinopyrid-4-ylcarbonylamino)phenyl]-5-[N-(3-dimethylaminopropyl)-N-methylamino]-2-nitrobenzamide (0.376 g); NMR Spectrum: (DMSOd$_6$) 1.67 (m, 2H), 2.11 (s, 6H), 2.2 (t, 2H), 3.07 (s, 3H), 3.51 (m, 6H), 3.71 (t, 4H), 6.77 (d, 1H), 6.84 (m, 1H), 7.1 (d, 1H), 7.24 (s, 1H), 7.31 (m, 2H), 7.48 (d, 1H), 8.04 (d, 1H), 8.17 (s, 1H), 8.26 (d, 1H), 10.34 (broad s, 1H), 10.42 (broad s, 1H); Mass Spectrum: M+H$^+$ 562.

A mixture of the material so obtained, 10% palladium-on-carbon (0.036 g), ammonium formate (0.4 g) and methanol (4 ml) was stirred and heated to reflux for 2 hours The reaction mixture was filtered through diatomaceous earth. The filtrate was evaporated and the residue was purified by column chromatography using C18 reversed phase silica and decreasingly polar mixtures of water and methanol as eluent. There was thus obtained the required starting material (0.256 g); NMR Spectrum: (DMSOd$_6$) 1.59 (m, 2H), 2.14 (s, 6H), 2.26 (t, 2H), 2.77 (s, 3H), 3.18 (t, 2H), 3.52 (t, 4H), 3.71 (t, 4H), 6.67 (d, 1H), 6.82 (d, 1H), 6.93 (d, 1H), 7.11 (d, 1H), 7.29 (m, 2H), 7.39 (d, 1H), 7.46 (d, 1H), 8.17 (s, 1H), 8.26 (d, 1H), 10.05 (broad s, 1H), 10.31 (broad s, 1H); Mass Spectrum: M+H⁺ 532.

c) The product gave the following data: NMR Spectrum: (DMSOd₆) 1.64 (m, 2H), 2.11 (s, 9H), 2.21 (m, 2H), 2.96 (s, 3H), 3.43 (t, 2H), 3.51 (m, 4H), 3.7 (m, 4H), 7.09 (d, 1H), 7.15 (m, 2H), 7.23 (s, 1H), 7.33 (m, 1H), 7.48 (m, 2H), 7.73 (s, 1H), 7.83 (d, 1H), 8.27 (d, 1H), 10.49 (broad s, 1H); Mass Spectrum: M+H⁺ 556.

d) The product gave the following data: Mass Spectrum: M+H⁺ 540.

The N-[2-methyl-5-(2-morpholinopyrid-4-ylcarbonylamino)phenyl]-2-amino-5-(4-methylpiperazin-1-yl)benzamide used as a starting material was prepared as follows:-

In an analogous procedure to that described in the fifth paragraph of the portion of Note a) which is concerned with the preparation of starting materials, N-[2-methyl-5-(2-morpholinopyrid-4-ylcarbonylamino)phenyl]-5-chloro-2-nitrobenzamide was reacted with 1-methylpiperazine to give N-[2-methyl-5-(2-morpholinopyrid-4-ylcarbonylamino)phenyl]-5-(4-methylpiperazin-1-yl)-2-nitrobenzamide; NMR Spectrum: (DMSOd₆) 2.21 (s, 3H), 2.24 (s, 3H), 2.41-2.47 (m, 4H), 2.63-2.69 (m, 2H), 3.46-3.53 (m, 8H), 3.69-3.72 (m, 4H), 7.0 (s, 1H) 7.04-7.12 (m, 2H), 7.19 (d, 1H), 7.25 (s, 1H), 7.57 (d, 1H), 7.88 (s, 1H), 8.04 (d, 1H), 8.26 (d, 1H), 9.83 (s, 1H), 10.33 (s, 1H); Mass Spectrum: M+H⁺ 560.

In an analogous procedure to that described in the sixth paragraph of the portion of Note a) which is concerned with the preparation of starting materials, N-[2-methyl-5-(2-morpholinopyrid-4-ylcarbonylamino)phenyl]-5-(4-methylpiperazin-1-yl)-2-nitrobenzamide was reduced to give the required starting material; Mass Spectrum: M+H⁺ 530.

e) The product gave the following data: Mass Spectrum: M+H⁺ 554.

f) The product gave the following data: NMR Spectrum: (DMSOd₆) 2.22 (s, 3H), 2.4, (m, 4H), 3.3 (m, 4H), 3.51 (t, 4H), 3.71 (t, 4H), 7.1 (d, 1H), 7.25 (m, 2H), 7.47 (s, 1H), 7.54 (t, 1H), 7.6 (s, 2H), 7.87 (m, 2H), 8.14 (s, 1H), 8.28 (d, 1H), 10.52 (broad s, 1H); Mass Spectrum: M+H⁺ 526.

The N-[3-(2-morpholinopyrid-4-ylcarbonylamino)phenyl]-2-amino-5-(4-methylpiperazin-1-yl)benzamide used as a starting material was prepared as follows:-

In an analogous procedure to that described in the fifth paragraph of the portion of Note c) which is concerned with the preparation of starting materials, N-[3-(2-morpholinopyrid-4-ylcarbonylamino)phenyl]-5-chloro-2-nitrobenzamide was reacted with 1-methylpiperazine to give N-[3-(2-morpholinopyrid-4-ylcarbonylamino)phenyl]-5-(4-methylpiperazin-1-yl)-2-nitrobenzamide in 89% yield; NMR Spectrum: (DMSOd₆) 2.2 (s, 3H), 2.41 (m, 4H), 3.5 (m, 8H), 3.71 (t, 4H), 7.07 (m, 3H), 7.31 (m, 3H), 7.48 (d, 1H), 8.03 (d, 1H), 8.16 (s, 1H), 8.26 (d, 1H), 10.35 (broad s, 1H), 10.44 (broad s, 1H); Mass Spectrum: M+H⁺ 546.

In an analogous procedure to that described in the sixth paragraph of the portion of Note c) which is concerned with the preparation of starting materials, N-[3-(2-morpholinopyrid-4-ylcarbonylamino)phenyl]-5-(4-methylpiperazin-1-yl)-2-nitrobenzamide was reduced. The material so obtained was purified by column chromatography on an isolute SCX ion exchange column using initially methanol and then a 99:1 mixture of methanol and a saturated aqueous ammonium hydroxide solution as eluent. There was thus obtained the required starting material in 50% yield; NMR Spectrum: (DMSOd₆) 2.2 (s, 3H), 2.4 (m, 4H), 3.0 (t, 4H), 3.52 (t, 4H), 3.71 (t, 4H), 6.68 (d, 1H), 6.96 (d, 1H), 7.1 (m, 2H), 7.25 (m, 2H), 7.4 (m, 2H), 8.15 (s,. 1H), 8.26 (d, 1H), 10.01 (broad s, 1H), 10.31 (broad s, 1H); Mass Spectrum: M+H⁺ 516.

g) The product gave the following data: NMR Spectrum: (DMSOd₆) 2.12 (s, 3H), 2.21 (s, 3H), 2.5 (m, 4H), 3.22 (m, 4H), 3.51 (m, 4H), 3.7 (m, 4H), 7.09 (d, 1H), 7.18 (m, 2H), 7.37 (s, 1H), 7.54 (m, 3H), 7.74 (s, 1H), 7.83 (d, 1H), 8.27 (d, 1H), 10.5 (broad s, 1H), Mass Spectrum: M+H⁺ 540.

h) The product gave the following data: Mass Spectrum: M+H⁺ 556.

The N-[2-methyl-5-(2-morpholinopyrid-4-ylcarbonylamino)phenyl]-2-amino-3-[N-(3-dimethylaminopropyl)-N-methylamino]benzamide used as a starting material was prepared as follows:-

In an analogous procedure to that described in the fourth paragraph of the portion of Note a) which is concerned with the preparation of starting materials, 3-chloro-2-nitrobenzoyl chloride (obtained by the reaction of 3-chloro-2-nitrobenzoic acid and oxalyl chloride) was reacted with N-(3-amino-4-methylphenyl)-2-morpholinopyridine-4-carboxamide to give N-[2-methyl-5-(2-morpholinopyrid-4-ylcarbonylamino)phenyl]-3-chloro-2-nitrobenzamide; NMR Spectrum: (DMSOd₆) 2.2 (s, 3H), 3.49-3.53 (m, 4H) 3.69-3.73 (m, 4H), 7.1 (d, 1H), 7.18-7.24 (m, 2H), 7.58 (d, 1H), 7.68-7.78 (m, 2H), 7.58 (d, 1H), 7.68-7.78 (m, 2H), 7.84-8.0 (m, 2H), 8.25 (d, 1H); Mass Spectrum: M+H⁺ 496 and 498.

In an analogous procedure to that described in the fifth paragraph of the portion of Note a) which is concerned with the preparation of starting materials, N-[2-methyl-5-(2-morpholinopyrid-4-ylcarbonylamino)phenyl]-3-chloro-2-nitrobenzamide was reacted with N-(3-dimethylaminopropyl)-N-methylamine to give N-[2-methyl-5-(2-morpholinopyrid-4-ylcarbonylamino)phenyl]-3-[N-(3-dimethylaminopropyl)-N-methylamino]-2-nitrobenzamide; NMR Spectrum: (DMSOd₆) 1.44-1.58 (m, 2H), 2.06 (s, 6H), 2.15 (t, 2H), 2.21 (s, 3H), 2.69 (s, 3H), 3.02 (t, 2H), 3.48-3.53 (m, 4H) 3.69-3.73 (m, 4H), 7.1 (d, 1H) 7.19-7.25 (m, 2H), 7.44-7.62 (m, 3H), 7.74-7.64 (m, 1H), 7.94 (d, 1H), 8.26 (d, 1H), 10.13 (s, 1H), 10.32 (s, 1H); Mass Spectrum: M+H⁺ 576.

In an analogous procedure to that described in the sixth paragraph of the portion of Note a) which is concerned with the preparation of starting materials, N-[2-methyl-5-(2-morpholinopyrid-4-ylcarbonylamino)phenyl]-3-[N-(3-dimethylaminopropyl)-N-methylamino]-2-nitrobenzamide was reduced catalytically to give the required starting material; Mass Spectrum: M+H⁺ 546.

i) The product gave the following data: NMR Spectrum: (DMSOd₆) 1.6-1.75 (m, 2H), 2.05 (s, 3H), 2.28 (s, 3H), 2.47-2.52 (m, 2H), 2.99 (s, 3H), 3.49-3.53 (m, 6H), 3.69-3.73 (m, 4H), 7.08 (d, 1H), 7.22 (s, 2H), 7.34-7.24 (m, 2H), 7.6 (d, 1H) 7.75-7.8 (m, 2H) 7.97 (s, 1H) 8.28 (d, 1H), 10.42 (s, 1H); Mass Spectrum: M+H⁺ 542.

The N-[2-methyl-5-(2-morpholinopyrid-4-ylcarbonylamino)phenyl]-2-amino-5-[N-(3-methylaminopropyl)-N-methylamino]benzamide used as a starting material was prepared as follows:-

In an analogous procedure to that described in the fifth paragraph of the portion of Note a) which is concerned with the preparation of starting materials, N-[2-methyl-5-(2-morpholinopyrid-4-ylcarbonylamino)phenyl]-5-chloro-2-nitrobenzamide was reacted with N-(3-methylaminopropyl)-N-methylamine to give N-[2-methyl-5-(2-morpholinopyrid-4-ylcarbonylamino)phenyl)-5-[N-(3-methylaminopropyl)-N-methylamino]-2-nitrobenzamide; NMR Spectrum: (DMSOd₆) 1.61-1.74 (m, 2H), 2.35 (s, 3H), 2.26. (m, 3H), 2.38-2.44 (m, 2H), 3.09 (s, 3H), 3.5-3.55 (m, 6H), 3.7-3.74 (m, 4H), 6.78 (s, 1H), 6.84 (d, 1H), 7.14 (d, 1H), 7.21 (d, 1H), 7.27 (s, 1H), 7.6 (d, 1H), 7.9 (s, 1H), 8.04 (d, 1H), 8.27 (d, 1H), 9.83 (s, 1H), 10.55 (s, 1H); Mass Spectrum: M+H⁺ 562.

In an analogous procedure to that described in the sixth paragraph of the portion of Note a) which is concerned with the preparation of starting materials, N-[2-methyl-5-(2-morpholinopyrid-4-ylcarbonylamino)phenyl]-3-[N-(3-methylaminopropyl)-N-methylamino]-2-nitrobenzamide was reduced catalytically to give the required starting material; NMR Spectrum: (DMSOd$_6$) 1.57-1.62 (m, 2H), 2.2 (s, 3H), 2.25 (s, 3H), 2.47-2.5 (m, 2H), 2.77 (s, 3H), 3.19-3.23 (m, 2H), 3.5-3.54 (m, 4H), 3.69-3.73 (m, 4H), 5.6 (s, 2H), 6.68 (d, 1H), 6.82 (d, 1H), 7.04 (s, 1H), 7.1 (d, 1H), 7.2-7.23 (m, 2H), 7.54 (d, 1H), 7.83 (d, 1H), 8.26 (d, 1H), 9.75 (s, 1H), 10.28 (s, 1H); Mass Spectrum: M+H$^+$ 532.

EXAMPLE 4

Using an analogous procedure to that described in Example 1, the appropriate 2-aminobenzamide was reacted with triethyl or trimethyl orthoformate to give the compounds described in Table II.

TABLE II

| No. | (R$^1$)$_m$ | (R)$_p$ | Note |
|---|---|---|---|
| 1 | 6-(4-methylpiperazin-1-yl) | 3-morpholino-5-trifluoromethyl | a |
| 2 | 6-[N-(3-dimethylaminopropyl)-N-methylamino] | 3-morpholino-5-trifluoromethyl | b |
| 3 | 8-[N-(3-dimethylaminopropyl)-N-methylamino] | 3-morpholino-5-trifluoromethyl | c |
| 4 | 6-methoxy | 3-fluoro-5-morpholino | d |

Notes a) Trimethyl orthoformate was used as the reactant and the product gave the following Data: NMR Spectrum: (DMSOd$_6$) 2.05 (s, 3H), 2.23 (s, 3H), 2.5 (m, 4H), 3.3 (m, 8H), 3.76 (t, 4H), 7.44 (m, 3H), 7.72 (m, 6H), 8.1 (s, 1H), 10.52 (br s, 1H); Mass Spectrum: M+H$^+$ 607.

The N-[2-methyl-5-(3-morpholino-5-trifluoromethylbenzamido)phenyl]-2-amino-5-(4-methylpiperazin-1-yl)benzamide used as a starting material was prepared as follows:-

Ethyl 3-morpholino-5-trifluoromethylbenzoate was prepared from ethyl 3-fluoro-5-trifluoromethylbenzoate by the method described by Brown et al., *Tetrahedron Lett.*, 1999, 40, 1219. The material so obtained compound gave the following data:—NMR Spectrum: (CDCl$_3$) 1.36 (t, 3H), 3.19 (t, 4H), 3.81 (t, 4H), 4.34 (m, 2H), 7.22 (d, 1H), 7.72 (d, 1H), 7.76 (s, 1H).

A mixture of ethyl 3-morpholino-5-trifluoromethylbenzoate (0.67 g), 1N aqueous sodium hydroxide solution (3.3 ml) and ethanol (6 ml) was stirred and heated to reflux for 15 minutes and then left to stand for 16 hours. The ethanol was evaporated and the residue was dissolved in water (6 ml). Hydrochloric acid (1 M, 3.3 ml) was added and the resultant solid was isolated, washed with water and dried. There was thus obtained 3-morpholino-5-trifluoromethylbenzoic acid as a solid (0.464 g); NMR Spectrum: (DMSOd$_6$) 3.25 (t, 4H), 3.73 (t, 4H), 7.4 (s, 1H), 7.53 (s, 1H), 7.65 (s, 1H), 13.3 (s, 1H).

A solution of 3-morpholino-5-trifluoromethylbenzoyl chloride (11.43 g; obtained by the reaction of the benzoic acid with oxalyl chloride using a conventional procedure) in methylene chloride (200 ml) was added to a stirred mixture of 4-methyl-3-nitroaniline (5.47 g), triethylamine (10 ml) and methylene chloride (200 ml). The resultant mixture was stirred at ambient temperature for 18 hours. The reaction mixture was washed with water and with a saturated aqueous sodium bicarbonate solution, dried (MgSO$_4$) and evaporated. The resultant solid was stirred with diethyl ether (300 ml) for 16 hours. The resultant solid was collected, washed with diethyl ether and dried. There was thus obtained N-(4-methyl-3-nitrophenyl)-3-morpholino-5-fluorobenzamide as a solid (10.4 g); NMR Spectrum: (CDCl$_3$) 2.58 (s, 3H), 3.22 (t, 4H), 3.83 (t, 4H), 7.21 (s, 2H), 7.32 (d, 1H), 7.41 (s, 1H), 7.58 (s, 1H), 7.82 (m, 1H), 8.02 (s, 1H), 8.23 (d, 1H).

The compound so obtained was dissolved in ethyl acetate (500 ml) and hydrogenated over 10% palladium-on-carbon catalyst (1.1 g) under 3 atmospheres pressure of hydrogen until the uptake of hydrogen ceased. The catalyst was removed by filtration and the filtrate was evaporated. The residue was triturated under ethyl acetate to give N-(3-amino-4-methylphenyl)-3-morpholino-5-trifluoromethylbenzamide (8.1 g); NMR Spectrum: (CDCl$_3$) 2.01 (s, 3H), 3.23 (t, 4H), 3.75 (t, 4H), 4.81 (s, 2H), 6.77 (m, 1H), 6.83 (d, 1H), 7.02 (d, 1H), 7.25 (s, 1H), 7.58 (s, 1H), 7.63 (s, 1H), 9.9 (s, 1H).

Diisopropylethylamine (0.918 ml) was added to a mixture of N-(3-amino-4-methylphenyl)-3-morpholino-5-trifluoromethylbenzamide (1 g), 5-chloro-2-nitrobenzoic acid (0.584 g), 2-(7-azabenzotriazol-1-yl)-1,1,3,3-tetramethyluronium hexafluorophosphate(V) (1.2 g) and DMF (6 ml) and the reaction mixture was stirred at ambient temperature for 16 hours. The mixture was poured onto a mixture of ice and water and the resultant precipitate was isolated, washed in turn with methanol and isohexane and dried under vacuum at 55° C. There was thus obtained N-[2-methyl-5-3-morpholino-5-trifluoromethylbenzamido)phenyl]-5-chloro-2-nitrobenzamide (0.965 g); NMR Spectrum: (DMSOd$_6$) 2.24 (s, 3H), 3.3 (m, 4H), 3.76 (m, 4H), 7.23 (d, 1H), 7.36 (s, 1H), 7.6 d, 1H), 7.65 (s, 1H), 7.72 (s, 1H), 7.82 (d, 1H), 7.90 (m, 2H), 8.17 (d, 1H), 10.17 (s, 1H), 10.38 (s, 1H); Mass Spectrum: M+H$^+$ 563.

A mixture of a portion (0.45 g) of the material so obtained and N-methylpiperazine (2 ml) was stirred and heated to 120° C. for 16 hours. The reaction mixture was poured onto a mixture of ice and water. The resultant solid was isolated, washed with water and dried under vacuum at 55° C. The solid so obtained was purified by chromatography on an ion exchange column (isolute SCX column) using initially methanol and then a mixture of methanol and a 1% aqueous ammonium hydroxide solution as eluent. There was thus obtained N-[2-methyl-5-(3-morpholino-5-trifluoromethylbenzamido)phenyl]-5-(4-methylpiperazin-1-yl)-2-nitrobenzamide (0.29 g); NMR Spectrum: (DMSOd$_6$) 2.21 (s, 3H), 2.24 (s, 3H), 2.5-3.3 (m, 8H), 3.48 (m, 4H), 3.76 (m, 4H), 7.0 (d, 1H), 7.07 (d, 1H), 7.2 (d, 1H), 7.36 (s, 1H), 7.6 (m, 3H), 7.88 (s, 1H), 8.04 (d, 1H), 9.84 (s, 1H), 10.37 (s, 1H); Mass Spectrum: M+H$^+$ 627.

A mixture of the material so obtained, ammonium formate (0.146 g), 10% palladium-on-carbon catalyst (0.029 g) and methanol (5 ml) was stirred and heated to 65° C. for 2 hours. The resultant mixture was filtered and the filtrate was evaporated. The residue was triturated under methylene chloride and filtered. The filtrate was evaporated to give N-[2-methyl-5-(3-morpholino-5-trifluoromethylbenzamido)phenyl]-2-amino-5-(4-methylpiperazin-1-yl)benzamide which was used without further purification.

b) Trimethyl orthoformate was used as the reactant and the product gave the following data: NMR Spectrum: (DMSOd$_6$) 1.67 (m, 2H), 2.05 (s, 3H), 2.13 (s, 6H), 2.27 (m, 2H), 3.0 (s, 1H), 3.3 (m, 4H), 3.47 (m, 2H), 3.76 (br s, 4H), 7.25 (d, 1H), 7.39 (m, 3H), 7.62 (m, 3H), 7.73 (d, 1H), 7.81 (d, 1H), 8.0 (s, 1H), 10.51 (br s, 1H); Mass Spectrum: M+H$^+$ 623.

The N-[2-methyl-5-(3-morpholino-5-trifluoromethylbenzamido)phenyl]-2-amino-5-[N-(3-dimethylaminopropyl)-N-methylamino]benzamide used as a starting material was prepared as follows:-

A mixture of N-[2-methyl-5-(3-morpholino-5-trifluoromethylbenzamido)phenyl]-5-choro-2-nitrobenzamide (0.45 g), N-(3-dimethylaminopropyl)-N-methylamine (2 ml) and DMSO (1 ml) was stirred and heated to 120° C. for 16 hours. The reaction mixture was poured onto a mixture of ice and water. The resultant solid was isolated, washed with water and dried under vacuum at 55° C. There was thus obtained N-[2-methyl-5-(3-morpholino-5-trifluoromethylbenzamido)phenyl]-[N-(3-dimethylaminopropyl)-N-methylamino]-2-nitrobenzamide (0.51 g); NMR Spectrum: (DMSOd$_6$) 1.69 (m, 2H), 2.12 (s, 6H), 2.24 (s, 5H), 3.08 (s, 3H), 3.3 (m, 4H), 3.52 (t, 2H), 3.76 (m, 4H), 6.76 (s, 1H), 6.83 (d, 1H), 7.2 (d, 1H), 7.36 (s, 1H), 7.66 (m, 3H), 7.89 (s, 1H), 8.04 (d, 1H), 9.82 (s, 1H), 10.37 (s, 1H).

A mixture of the material so obtained, ammonium formate (0.24 g), 10% palladium-on-carbon catalyst (0.05 g) and methanol (10 ml) was stirred and heated to 65° C. for 7 hours. The resultant mixture was filtered and the filtrate was evaporated. The residue was triturated under methylene chloride and filtered. The filtrate was evaporated to give N-[2-methyl-5-(3-morpholino-5-trifluoromethylbenzamido)phenyl]-2-amino-5-[N-(3-dimethylaminopropyl)-N-methylamino]benzamide which was used without further purification.

c) Trimethyl orthoformate was used as the reactant and the product gave the following data: NMR Spectrum: (DMSOd$_6$) 1.72 (m, 2H), 2.06 (m, 9H), 2.19 (t, 2H), 2.94 (s, 3H), 3.3 (m, 4H), 3.49 (t, 2H), 3.76 (br s, 4H), 7.26 (d, 1H), 7.42 (m, 3H), 7.68 (m, 3H), 7.8 (m, 2H), 8.21 (s, 1H), 10.49 (br s, 1H); Mass Spectrum: M+H$^+$ 623.

The N-[2-methyl-5-(3-morpholino-5-trifluoromethylbenzamido)phenyl]-2-amino-3-[N-(3-dimethylaminopropyl)-N-methylamino]benzamide used as a starting material was prepared as follows:-

Diisopropylethylamine (0.46 ml) was added to a mixture of N-(3-amino-4-methylphenyl)-3-morpholino-5-trifluoromethylbenzamide (0.5 g), 3-chloro-2-nitrobenzoic acid (0.292 g), 2-(7-azabenzotriazol-1-yl)-1,1,3,3-tetramethyluronium hexafluorophosphate(V) (0.6 g) and DMF (3 ml) and the reaction mixture was stirred at ambient temperature for 16 hours. The mixture was poured onto a mixture of ice and water and the resultant precipitate was isolated, washed in turn with methanol and isohexane and dried under vacuum at 55° C. There was thus obtained N-[2-methyl-5-(3-morpholino-5-trifluoromethylbenzamido)phenyl]-3-chloro-2-nitrobenzamide (0.45 g); NMR Spectrum: (DMSOd$_6$) 2.22 (s, 3H), 3.3 (m, 4H), 3.76 (m, 4H), 7.25 (d, 1H), 7.37 (s, 1H), 7.71 (m, 5H), 7.96 (d, 2H), 10.36 (br s, 1H), 10.38 (br s, 1H); Mass Spectrum: M+H$^+$ 563.

A mixture of the material so obtained, N-(3-dimethylaminopropyl)-N-methylamine (2 ml) and DMSO (1 ml) was stirred and heated to 120° C. for 16 hours. The reaction mixture was poured onto a mixture of ice and water. The resultant solid was isolated, washed with water and dried under vacuum at 55° C. There was thus obtained N-[2-methyl-5-(3-morpholino-5-trifluoromethylbenzamido)phenyl]-3-[N-(3-dimethylaminopropyl)-N-methylamino]-2-nitrobenzamide (0.51 g); NMR Spectrum: (DMSOd$_6$) 1.52 (m, 2H), 2.06 (s, 6H), 2.15 (m, 2H), 2.22 (s, 3H), 2.69 (s, 3H), 3.03 (t, 2H), 3.3 (m, 4H), 3.76 (m, 4H), 7.22 (d, 1H), 7.36 (m, 2H), 7.53 (m, 4H), 7.73 (d, 2H), 10.14 (br s, 1H), 10.35 (br s, 1H).

A mixture of the material so obtained, ammonium formate (0.24 g), 10% palladium-on-carbon catalyst (0.05 g) and methanol (10 ml) was stirred and heated to 65° C. for 7 hours. The resultant mixture was filtered and the filtrate was evaporated. The residue was triturated under methylene chloride and filtered. The filtrate was evaporated to give. N-[2-methyl-5-(3-morpholino-5-trifluoromethylbenzamido)phenyl]-2-amino-3-N-(3-dimethylaminopropyl)-N-methylamino]benzamide which was used without further purification.

d) Trimethyl orthoformate was used as the reactant and the product gave the following data: NMR Spectrum: (DMSOd$_6$) 2.06 (s, 3H), 3.21 (m, 4H), 3.73 (m, 4H), 3.89 (s, 3H), 6.97 (d, 1H), 7.11 (d, 1H), 7.29 (s, 1H), 7.42 (d, 1H), 7.49 (d, 1H), 7.58 (d, 1H), 7.72 (d, 1H), 7.78 (m, 2H), 8.17 (s, 1H), 10.33 (s, 1H); Mass Spectrum: M+H$^+$ 489.

The N-[2-methyl-5-(3-fluoro-5-morpholinobenzamido)phenyl]-2-amino-5-methoxybenzamide used as a starting material was prepared as follows:-

A solution of 3,5-difluorobenzoyl chloride (2.82 g) in methylene chloride (20 ml) was added to a stirred mixture of 4-methyl-3-nitroaniline (2.28 g), triethylamine (4.35 ml) and methylene chloride (80 ml). The resultant mixture was stirred at ambient temperature for 16 hours. The precipitate was isolated, washed with methylene chloride and dried. There was thus obtained N-(4-methyl-3-nitrophenyl)-3,5-difluorobenzamide; NMR Spectrum: (DMSOd$_6$) 2.43 (s, 3H). 7.43 (m, 2H), 7.63 (m, 2H), 7.95 (m, 2H), 8.43 (d, 1H), 10.42 (s, 1H); Mass Spectrum: M+H$^+$ 293.

A mixture of a portion (1 g) of the material so obtained and morpholine (5 ml) was stirred and heated to 100° C. for 48 hours and then to 120° C. for 24 hours. The reaction mixture was cooled and poured into water (100 ml). The resultant solid was isolated, washed with water and dried. The material so obtained was purified by column chromatography on silica using a 1:1 mixture of isohexane and ethyl acetate as eluent. There was thus obtained N-(4-methyl-3-nitrophenyl)-3-fluoro-5-morpholinobenzamide as a solid (0.53 g); NMR Spectrum: (DMSOd$_6$) 2.46 (s, 3H), 3.22 (t, 4H), 3.75 (t, 4H), 6.98 (m, 1H), 7.12 (d, 1H), 7.27 (s, 1H), 7.46 (d, 1H), 7.96 (m, 1H), 8.43 (d, 1H), 10.48 (s, 1H); Mass Spectrum: M+H$^+$ 360.

A portion (0.483 g) of the compound so obtained was dissolved in ethyl acetate (40 ml) and hydrogenated over 10% palladium-on-carbon catalyst (0.6 g) under an atmosphere of hydrogen until the uptake of hydrogen ceased. The catalyst was removed by filtration and the filtrate was evaporated. The residue was triturated under diethyl ether (25 ml). The resultant solid was collected, washed with diethyl ether and dried. There was thus obtained N-(3-amino-4-methylphenyl)-3-fluoro-5-morpholinobenzamide (0.341 g); NMR Spectrum: (DMSOd$_6$) 1.99 (s, 3H), 3.19 (t, 4H), 3.76 (t, 4H), 4.8 (s, 2H), 6.75 (d, 1H), 6.82 (d, 1H), 6.9 (d, 1H), 7.02 (s, 1H), 7.04 (d, 1H), 7.23 (s, 1H), 9.81 (s, 1H).

Oxalyl chloride (0.523 ml) was added to a stirred mixture of 5-methoxy-2-nitrobenzoic acid (0.99 g), DMF (a few drops) and methylene chloride (30 ml) and the mixture was stirred at ambient temperature for for 3.5 hours. The mixture was evaporated and the residue was dissolved in methylene chloride (30 ml) and N-(3-amino-4-methylphenyl)-3-fluoro-5-morpholinobenzamide (1.65 g) and triethylamine (0.697 ml) were added in turn. The resultant mixture was stirred at ambient temperature for 2 hours. The mixture was evaporated and the residue was triturated under water. The resultant solid was isolated, washed in turn with a saturated aqueous sodium bicarbonate solution, water and diethyl ether and dried under vacuum at 55° C. There was thus obtained N-[2-methyl-5-(3-fluoro-5-morpholinobenzamido)phenyl]-5-methoxy-2-nitrobenzamide (2.29 g); NMR Spectrum: (DMSOd$_6$) 2.24 (s, 3H), 3.23 (m, 4H), 3.75 (m, 4H), 3.95 (s, 3H), 6.96 (d, 1H), 7.17 (m, 4H), 7.32 (s, 1H), 7.58 (d, 1H), 7.89 (s, 1H), 8.18 (d, 1H), 10.0 (s, 1H), 10.22 (s, 1H); Mass Spectrum: M+H$^+$ 509.

A mixture of a portion (1.28 g) of the material so obtained, 10% palladium-on-carbon catalyst (0.128 g) and methanol (60 ml) was stirred under an atmosphere of hydrogen gas for 20 hours. Ethyl acetate (30 ml) was added and the reaction mixture was stirred for an additional 2 hours under a hydrogen atmosphere. The reaction mixture was filtered and the filtrate was evaporated. The residue was dissolved in the minimum amount of ethyl acetate and a solid was precipitated by the addition of diethyl ether. The solid was isolated and dried under vacuum at 55° C. There was thus obtained N-[2-methyl-5-(3-fluoro-5-morpholinobenzamido)phenyl]-2-amino-5-methoxybenzamide (0.98 g); NMR Spectrum: (DMSOd$_6$) 2.2 (s, 3H), 3.22 (m, 4H), 3.74 (m, 7H), 5.93 (br s, 2H), 6.72 (d, 1H), 6.92 (m, 2H), 7.12 (d, 1H), 7.22 (d, 1H), 7.27 (m, 2H), 7.54 (d, 1H), 7.77 (s, 1H), 9.69 (s, 1H), 10.14 (s 1H); Mass Spectrum: M+H$^+$ 479.

EXAMPLE 5

3-[5-(2-Chloropyrid-4-ylcarbonylamino)-2-methylphenyl]-6-(4-methylpiperazin-1-yl)-3,4-dihydroquinazolin-4-one 2-Chloropyridine-4-carbonyl chloride (0.61 g) was added to a stirred mixture of 3-(5-amino-2-methylphenyl)-6-(4-methylpiperazin-1-yl)-3,4-dihydroquinazolin-4-one (1 g), triethylamine (1 g) and methylene chloride (15 ml) and the resultant mixture was stirred at ambient temperature for 18 hours. The mixture was washed with a saturated aqueous sodium bicarbonate solution and the organic phase was evaporated. There was thus obtained the title compound (1.28 g); NMR Spectrum: (DMSOd$_6$) 2.05 (s, 3H), 2.22 (s, 3H), 2.46-2.5 (m, 4H), 3.25-3.28 (m, 4H), 7.42-7.47 (m, 2H), 7.62 (s, 1H), 7.76-7.79 (m, 2H), 7.85 (d, 1H), 7.98 (s, 1H), 8.07 (s, 1H), 8.61 (d, 1H), 10.65 (s, 1H); Mass Spectrum: M+H$^+$ 489 & 491.

The 3-(5-amino-2-methylphenyl)-6-(4-methylpiperazin-1-yl)-3,4-dihydroquinazolin-4-one used as a starting material was prepared as follows:-

Oxalyl chloride (8.5 ml) was added dropwise to a stirred solution of 5-chloro-2-nitrobenzoic acid (15.1 g) in a mixture of methylene chloride (200 ml) and DMF (a few drops) which had been cooled to 0° C. The mixture was allowed to warm to ambient temperature and was stirred for a further 4 hours. The solvent was evaporated. The residue was dissolved in methylene chloride (300 ml) and added dropwise to a stirred mixture of 2-methyl-5-nitroaniline (10.6 g), triethylamine (27.2 ml) and methylene chloride (300 ml). The resultant mixture was stirred at ambient temperature for 16 hours. The precipitate was isolated, washed in turn with water and diethyl ether and dried under vacuum at 40° C. There was thus obtained N-(2-methyl-5-nitrophenyl)-5-chloro-2-nitrobenzamide (24.9 g); NMR Spectrum: (DMSOd$_6$) 2.34 (s, 3H), 7.46 (d, 1H), 7.75 (s, 1H), 7.88 (d, 1H), 8.03-8.16 (m, 2H), 8.56 (s, 1H); Mass Spectrum: M+H$^+$ 335.

A mixture of a portion (15 g) of the material so obtained and N-methylpiperazine (24.8 ml) was stirred and heated to 100° C. for 16 hours. The reaction mixture was cooled to ambient temperature and poured into water. The resultant precipitate was isolated, washed with water and dried under vacuum at 40° C. There was thus obtained N-(2-methyl-5-nitrophenyl)-5-(4-methylpiperazin-1-yl)-2-nitrobenzamide (14.8 g); NMR Spectrum: (DMSOd$_6$) 2.22 (s, 3H), 2.38 (s, 3H), 2.41-2.45 (m, 4H), 3.48-3.53 (m, 4H), 7.08 (d, 1H), 7.17 (s, 1H), 7.53 (d, 1H), 7.98 (d, 1H), 8.07 (d, 1H), 8.53 (s, 1H), 10.15 (s, 1H); Mass Spectrum: M+H$^+$400.

A mixture of the material so obtained, 10% palladium-on-carbon catalyst (1.48 g) and methanol (500 ml) was stirred under an atmosphere of hydrogen gas until hydrogen uptake ceased. The catalyst was filtered off and the filtrate was evaporated. There was thus obtained N-(5-amino-2-methylphenyl)-2-amino-5-(4-methylpiperazin-1-yl)benzamide (10.11 g); NMR Spectrum: (DMSOd$_6$) 2.02 (s, 3H), 2.2 (s, 3H), 2.4-2.45 (m, 4H), 2.97-3.0 (m, 4H), 4.84 (s, 2H), 5.82 (s, 2H), 6.36 (d, 1H), 6.57 (s, 1H), 6.66 (d, 1H), 6.85 (d, 1H), 6.92 (d, 1H), 7.18 (s, 1H), 9.4 (s, 1H); Mass Spectrum: M+H$^+$ 340.

A mixture of a portion (8.27 g) of the material so obtained, triethyl orthoformate (8.27 ml), glacial acetic acid (0.7 ml) and ethanol (150 ml) was stirred and heated to 70° C. for 16 hours. A 1N aqueous hydrochloric acid solution (24 ml) was added and the mixture was stirred at 60° C. for 1 hour. The resultant mixture was evaporated. The residue was dissolved in water, basified by the addition of sodium bicarbonate and extracted with methylene chloride. The organic extract was evaporated to give 3-(5-amino-2-methylphenyl)-6-(4-methylpiperazin-1-yl)-3,4-dihydroquinazolin-4-one (8.29 g); NMR Spectrum: (DMSOd$_6$) 1.86 (s, 3H), 2.22 (s, 3H), 2.42-2.45 (m, 4H), 3.24-3.28 (m, 4H), 5.14 (s, 2H), 6.47 (s, 1H), 6.61 (d, 1H), 7.02 (d, 1H), 7.45 (s, 1H), 7.59 (s, 1H), 7.96 (s, 1H); Mass Spectrum: M+H$^+$ 350.

EXAMPLE 6

3-[2-Methyl-5-(2-pyrrolidin-1-ylpyrid-4-ylcarbonylamino)phenyl]-6-(4-methylpiperazin-1-yl)-3,4-dihydroquinazolin-4-one A mixture of 3-[5-(2-chloropyrid-4-ylcarbonylamino)-2-methylphenyl]-6-4-methylpiperazin-1-yl)-3,4-dihydroquinazolin-4-one (0.18 g) and pyrrolidine (2 ml) was stirred and heated to 100° C. for 16 hours. The mixture was cooled to ambient temperature and poured into water. The resultant solid was isolated, washed with water and dried under vacuum at 40° C. There was thus obtained the title compound (0.11 g); NMR Spectrum: DMSOd$_6$) 1.94-1.97 (m, 4H), 2.04 (s, 3H), 2.22 (s, 3H), 2.45-2.49 (m, 4H), 3.25-3.28 (m, 4H), 3.4-3.45 (m, 4H), 6.85 (s, 1H), 6.96 (d, 1H), 7.42 (d, 1H), 7.42 (d, 1H), 7.44 (s, 1H), 7.62 (s, 2H), 7.77-7.79 (m, 2H), 8.07 (s, 1H), 8.2 (s, 1H), 10.42 (s, 1H); Mass Spectrum: M+H$^+$ 524.

EXAMPLE 7

Using an analogous procedure to that described in Example 6, the appropriate 6-substituted 3-[5-(2-chloropyrid-4-ylcarbonylamino)-2-methylphenyl]-3,4-dihydroquinazolin-4-one was reacted with the appropriate amine to give the compounds described in Table III.

TABLE III

| No. | $(R^1)_m$ | R | Note |
|---|---|---|---|
| 1 | 6-(4-methylpiperazin-1-yl) | piperidino | a |
| 2 | 6-(4-methylpiperazin-1-yl) | 3-pyrrolin-1-yl | b |
| 3 | 6-(4-methylpiperazin-1-yl) | homopiperidin-1-yl | c |
| 4 | 6-(4-methylpiperazin-1-yl) | azetidin-1-yl | d |
| 5 | 6-(4-methylhomopiperazin-1-yl) | piperidino | e |
| 6 | 6-(4-methylhomopiperazin-1-yl) | pyrrolidin-1-yl | f |
| 7 | 6-(4-methylhomopiperazin-1-yl) | morpholino | g |

Notes
a) The product gave the following data: NMR Spectrum: (DMSOd$_6$) 1.5-1.64 (m, 6H), 2.04 (s, 3H), 2.2 (s, 3H), 2.45-2.49 (m, 4H), 3.55-3.59 (m,4H), 6.98 (d, 1H), 7.19 (s, 1H), 7.42 (d, 1H), 7.47 (s, 1H), 7.76-7.78 (m, 2H), 8.07 (s, 1H), 8.21 (s, 1H), 10.42 (s, 1H); Mass Spectrum: M+H$^+$ 538.
b) The product gave the following data: NMR Spectrum: (DMSOd$_6$) 2.04 (s, 3H), 2.22 (s, 3H), 2.47-2.5 (m, 4H), 3.25-3.31 (m, 4H), 6.03 (s, 2H), 6.87 (s, 1H), 7.01 (d, 1H), 7.42 (d, 1H), 7.47 (s, 2H), 7.62 (d, 2H), 8.07 (s, 1H), 8.23 (d, 1H), 10.45 (s, 1H); Mass Spectrum: M+H$^-$ 522.
c) The product gave the following data: NMR Spectrum (DMSOd$_6$) 1.45-1.47 (m, 4H), 1.54-1.56 (m, 4H), 2.04 (s, 3H), 2.22 (s, 3H), 2.45-2.5 (m, 4H), 3.25-3.27 (m, 4H), 3.62-3.64 (m, 4H), 6.91 (d, 1H), 6.96 (s, 1H), 10.42 (s, 1H); Mass Spectrum: M+H$^+$ 5.52.
d) The product gave the following data: Mass Spectrum: M+H$^+$ 510.
e) The product gave the following data: NMR Spectrum: (CDCl$_3$) 1.42-1.46 (m, 6H), 1.78 (s, 3H), 1.92-2.04 (m, 2H), 2.48-2.56 (m, 2H), 2.64-2.72 (m, 2H), 3.44-3.58 (m, 6H), 3.6-3.64 (m, 2H), 6.78 (d, 1H), 7.01 (s, 1H), 7.15-7.2 (m, 2H), 7.38 (s, 1H), 7.5 (s, 1H), 7.58-7.68 (m, 3H), 8.12 (d, 1H), 8.4 (s, 1H); Mass Spectrum: M+H$^+$ 552.
f) The product gave the following data: NMR Spectrum: (CDCl$_3$) 1.84-2.04 (m, 9H), 2.32 (s, 3H), 2.48-2.58 (m, 2H), 2.64-2.7 (m, 2H), 3.32-3.44 (m, 4H), 3.5-3.58 (m, 2H), 3.6-3.64 (m, 2H), 6.72-6.79 (m, 2H), 7.14-7.2 (m, 2H), 7.38 (s, 1H), 7.52-7.62 (m, 3H), 7.64 (s, 1H), 8.12 (d, 1H), 8.44 (s, 1H); Mass Spectrum: M+H$^+$ 538.
g) The product gave the following data: NMR Spectrum: (CDCl$_3$) 1.98 (s, 3H), 2.02-2.12 (m, 2H), 2.39 (s, 3H0, 2.58-2.62 (m, 2H), 2.74-2.8 (m, 2H), 3.5-3.58 (m, 4H), 3.6-3.66 (m, 2H), 3.66-3.78 (m, 6H), 6.98 (d, 1H), 7.08 (s, 1H), 7.2-7.26 (m, 2H), 7.44 (s, 1H), 7.58 (s, 1H), 7.64 (d, 1H), 7.72-7.78 (m, 2H), 8.24 (d, 1H), 8.44 (s, 1H); Mass Spectrum: M+H$^+$ 554.

EXAMPLE 8

3-[5-(3,5-Difluorobenzamido)-2-methylphenyl]-6-(4-methylpiperazin-1-yl)-3,4-dihydroquinazolin-4one 3,5-Difluorobenzoyl chloride (0.91 g) was added to a stirred mixture of 3-(5-amino-2-methylphenyl)-6-(4-methylpiperazin-1-yl)-3,4-dihydroquinazolin-4-one (1.5 g), triethylamine (1.04 g) and methylene chloride (50 ml) and the resultant mixture was stirred at ambient temperature for 18 hours. The mixture was washed with a saturated aqueous sodium bicarbonate solution and the organic phase was evaporated. There was thus obtained the title compound (2.04 g); NMR Spectrum: (DMSOd$_6$) 2.05 (s, 3H), 2.22 (s, 3H), 2.45-2.5 (m, 4H), 3.24-3.3 (m, 4H), 7.41-7.56 (m, 3H), 7.61-7.68 (m, 4H), 7.75-7.79 (m, 2 H), 8.06 (s, 1H), 10.5 (s, 1H); Mass Spectrum: M+H$^+$ 490.

EXAMPLE 9

Using an analogous procedure to that described in Example 6, 3-[5-(3,5-difluorobenzamido)-2-methylphenyl]-6-(4-methylpiperazin-1-yl)-3,4-dihydroquinazolin-4-one, 3-[5-(3-fluoro-4-trifluoromethylbenzamido)-2-methylphenyl]-6-(4-methylpiperazin-1-yl)-3,4-dihydroquinazolin-4-one or 3-[5-(3,5-difluorobenzamido)-2-methylphenyl]-6-(4-methylhomopiperazin-1-yl)-3,4-dihydroquinazolin-4-one as appropriate was reacted with the appropriate amine to give the compounds described in Table IV.

TABLE IV

| No. | $(R^1)_m$ | $(R)_p$ | Note |
|---|---|---|---|
| 1 | 6-(4-methylpiperazin-1-yl) | 3-fluoro-5-pyrrolidin-1-yl | a |
| 2 | 6-(4-methylpiperazin-1-yl) | 3-fluoro-5-piperidino | b |
| 3 | 6-(4-methylpiperazin-1-yl) | 3-azetidin-1-yl-5-fluoro | c |
| 4 | 6-(4-methylpiperazin-1-yl) | 3-fluoro-5-(3-pyrrolin-1-yl) | d |
| 5 | 6-(4-methylpiperazin-1-yl) | 3-fluoro-3-morpholino | e |

TABLE IV-continued

[Structure: Quinazolinone with (R¹)ₘ at position 6, N-aryl group with Me and NHCO-phenyl(R)ₚ substituent, position 3]

| No. | (R¹)ₘ | (R)ₚ | Note |
|---|---|---|---|
| 6 | 6-(4-methylpiperazin-1-yl) | 3-morpholino-5-trifluoromethyl | f |
| 7 | 6-(4-methylhomopiperazin-1-yl) | 3-fluoro-5-pyrrolidin-1-yl | g |
| 8 | 6-(4-methylhomopiperazin-1-yl) | 3-fluoro-5-piperidino | h |

Notes a) The product gave the following data: NMR Spectrum: (DMSOd$_6$) 1.95-2.0 (m, 4H), 2.04 (s, 3H), 2.18 (s, 3H), 2.0-2.23 (m, 4H), 2.47-2.5 (m, 4H), 3.25-3.3 (m, 4H), 6.84-6.89 (m, 2H), 7.22 (d, 1H), 7.4 (d, 1H), 7.6-7.62 (m, 2H), 7.76-7.82 (m, 2H), 8.07 s, 1H), 10.27 (s, 1H); Mass Spectrum: M+H$^+$ 541.

b) The product gave the following data: NMR Spectrum: (DMSOd$_6$) 1.22-1.58 (m, 6H), 2.04 (s, 3H), 2.2 (s, 3H), 2.45-2.5 (m, 4H), 3.25-3.29 (m, 4H), 6.91 (d, 1H), 7.02 (d, 1H), 7.26 (s, 1H), 7.4 (d, 1H), 7.47 (s, 1H), 7.62 (s, 2H), 7.76-7.81 (m, 2H), 8.06 (s, 1H), 10.3 (s, 1H); Mass Spectrum: M+H$^+$ 555.

c) The product gave the following data: Mass Spectrum: M+H$^+$ 527 d) The product gave the following data: Mass Spectrum: M+H$^+$ 539 e) The product gave the following data: Mass Spectrum: M+H$^+$ 557 f) 3-[5-(3-Fluoro-4-trifluoromethylbenzamido)-2-methylphenyl]-6-(4Methylpiperazin-1-yl)-3,4-dihydroquinazolin-4-one and morpholine were heated together at 130° C. for 4 days. The product gave the following data: NMR Spectrum: (DMSOd$_6$) 2.05 (s, 3H), 2.22 (s, 3H), 2.4-2.6 (m, 4H), 2.86-2.96 (m, 4H), 3.22-3.32 (m, 4H), 3.65-3.74 (m, 4H), 7.4-7.48 (m, 2H), 7.62 (s, 2H), 7.76-7.86 (m, 4H), 8.06 (d, 2H), 10.53 (s, 1H); Mass Spectrum: M+H$^+$ 607.

g) 3-[5-(3,5-Diflorobenzamido)-2-methylphenyl]-6-(4-methylhomopiperazin-1-yl)-3,4-dihydroquinazolin-4-one and pyrrolidine were heated together at 95° C. for 16 hours and at 105° C. for 4 hours. The product gave the following data: NMR Spectrum: (CDCl$_3$) 1.98-2.1 (m, 9H), 2.19 (s, 3H), 2.58-2.62 (m, 2H), 2.72-2.8 (m, 2H), 3.24-3.32 (m, 4H), 3.58-3.62 (m, 2H), 3.68-3.72 (m, 2H), 6.32 (d, 1H), 6.76 (d, 1H), 6.82 (s, 1H), 7.2-7.3 (m, 2H, 7.44 (s, 1H), 7.6-7.68 (m, 3H, 7.78 (s, 1H), 8.19 (s, 1H); Mass Spectrum: M+H$^+$ 555.

h) the product gave the following data: NMR Spectrum: (CDCl$_3$) 1.52-1.74 (m, 6H), 2.02-2.1 (m, 5H), 2.4 (s, 3H), 2.58-2.6 (m, 2H), 2.76-2.8 (m, 2H), 3.18-3.28 (m, 4H), 3.58-3.62 (m, 2H), 3.68-3.72 (m, 2H), 6.68 (d, 1H), 6.88 (d, 1H), 7.18 (s, 1H), 7.2-7.32 (m, 2H), 7.44 (s, 1H), 7.6-7.68 (m, 3H), 7.78 (s, 1H), 8.17 (s, 1H); Mass Spectrum: M+H$^+$ 569.

EXAMPLE 10

3-[5-Dibenzofuran-4-ylcarbonylamino-2-methylphenyl]-6-(4-methylpiperazin-1-yl)-3,4-dihydroquinazolin-4-one A solution of 3-(5-amino-2-methylphenyl)-6-(4-methylpiperazin-1-yl)-3,4-dihydroquinazolin-4-one (0.165 g) in DMF (0.5 ml) was added to a stirred mixture of dibenzofuran-4-carboxylic acid (0.1 g), diisopropyethylamine (0.164 ml), 2-(7-azabenzotriazol-1-yl)-1,1,3,3-tetramethyluronium hexafluorophosphate(V) (0.214 g) and DMF (0.5 ml) and the reaction mixture was stirred at ambient temperature for 16 hours. The mixture was diluted with water and the resultant solid was isolated, washed in turn with water and diethyl ether and dried under vacuum at 55° C. There was thus obtained the title compound (0.228 g); NMR Spectrum: (DMSOd$_6$) 2.07 (s, 3H), 2,25 (s, 3H), 2.5-3.3 (m, 8H), 7.55 (m, 7H), 7.83 (m, 4H), 8.12 (s, 1H), 8.21 (d, 1H), 8.34 (d, 1H), 10.59 (s, 1H); Mass Spectrum: M+H$^+$ 544.

EXAMPLE 11

Using an analogous procedure to that described in Example 10, 3-(5-amino-2-methylphenyl)-6-(4-methylpiperazin-1-yl)-3,4-dihydroquinazolin-4-one, 3-(5-amino-2-methylphenyl)-6-4-methylhomopiperazin-1-yl)-3,4-dihydroquinazolin-4-one or 3-(5-amino-2-methylphenyl)-8-(4-methylpiperazin-1-yl)-3,4-dihydroquinazolin-4-one was reacted with the appropriate carboxylic acid to give the compounds described in Table V.

TABLE V

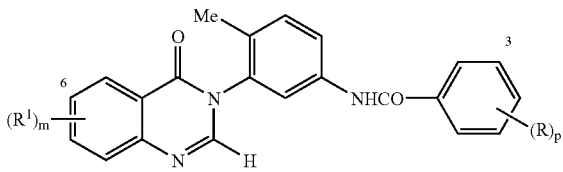

| No. | $(R^1)_m$ | $(R)_p$ | Note |
|---|---|---|---|
| 1 | 6-(4-methylpiperazin-1-yl) | 2-methoxy-3-phenyl | a |
| 2 | 6-(4-methylpiperazin-1-yl) | 3-(4-fluorophenyl) | b |
| 3 | 6-(4-methylpiperazin-1-yl) | 3-(2-furyl) | c |
| 4 | 6-(4-methylpiperazin-1-yl) | 3-cyclopentyloxy | d |
| 5 | 6-(4-methylpiperazin-1-yl) | 3-cyclopentyloxy-4-methoxy | e |
| 6 | 6-(4-methylpiperazin-1-yl) | 3-acetamido | f |
| 7 | 6-(4-methylpiperazin-1-yl) | 3-(N-methylmethanesulphonamido) | g |
| 8 | 6-(4-methylpiperazin-1-yl) | 3-(1,1-dioxidoisothiazolidin-2-yl) | h |
| 9 | 6-(4-methylpiperazin-1-yl) | 3-morpholino | i |
| 10 | 6-(4-methylpiperazin-1-yl) | 3-fluoro-4-trifluoromethyl | j |
| 11 | 6-(4-methylpiperazin-1-yl) | 3-tetrahydrofuranyloxy | k |
| 12 | 6-(4-methylpiperazin-1-yl) | 2-methoxy | l |
| 13 | 6-(4-methylpiperazin-1-yl) | 3-ethoxy | m |
| 14 | 6-(4-methylpiperazin-1-yl) | 3-(1,1,2,2-tetrafluoroethoxy) | n |
| 15 | 6-(4-methylhomopiperazin-1-yl) | 3-morpholino | o |
| 16 | 6-(4-methylhomopiperazin-1-yl) | 3-fluoro-5-morpholino | p |
| 17 | 6-(4-methylhomopiperazin-1-yl) | 3-morpholino-5-trifluoromethyl | q |
| 18 | 6-(4-methylhomopiperazin-1-yl) | 3-(2-furyl) | r |
| 19 | 8-(4-methylpiperazin-1-yl) | 3-morpholino | s |
| 20 | 8-(4-methylpiperazin-1-yl) | 3-fluoro-5-morpholino | t |
| 21 | 8-(4-methylpiperazin-1-yl) | 3-morpholino-5-trifluoromethyl | u |
| 22 | 8-(4-methylpiperazin-1-yl) | 3-(2-furyl) | v |
| 23 | 8-(4-methylpiperazin-1-yl) | 3-(4-fluorophenyl) | w |

Notes a) The reaction product was purified by column chromatography on reversed-phase silica using initially water and then decreasingly polar mixtures of methanol and water as eluent. There was thus obtained the required product in 33% yield; NMR Spectrum: (DMSOd$_6$) 2.04 (s, 3H) 2.27 (s, 3H), 2.5-3.3 (m, 8H), 3.42 (s, 3H), 7.54 (m, 13H), 7.72 d, 1H), 8.09 (s, 1H), 10.52 (s, 1H); Mass Spectrum: M+H$^+$ 560.

The 2-methoxy-3-phenylbenzoic acid used as a starting material was prepared as follows:-

Methyl iodide (0.409 ml) was added to a stirred mixture of methyl 2-hydroxy-3-phenylbenzoate (0.5 g), potassium carbonate (0.606 g) and acetone (5 ml) and the reaction mixture was stirred at 55° C. for 2.5 hours. The mixture was evaporated and the residue was partitioned between ethyl acetate and water. The organic phase was dried (MgSO$_4$) and evaporated to give a mixture of the starting material and methyl 2-methoxy-3-phenylbenzoate. This mixture was dissolved in DMF (1 ml) and potassium carbonate (0.606 g) and dimethyl sulphate (0.207 ml) were added and the resultant reaction mixture was stirred at 80° C. for 16 hours. The mixture was partitioned between ethyl acetate and water. The organic phase was dried (MgSO$_4$) and evaporated to give methyl 2-methoxy-3-phenylbenzoate (0.458 g) as an oil; NMR Spectrum: (DMSOd$_6$) 3.48 (s, 3H), 3.94 (s, 3H), 7.21 (m, 1H), 7.4 (m, 6H), 7.73 (d, 1H).

A mixture of the material so obtained, 2N aqueous sodium hydroxide solution (5 ml), methanol (10 ml) and THF (3 ml) was stirred at ambient temperature for 16 hours. The organic solvents were evaporated and the aqueous reaction mixture was acidified by the addition of 2N aqueous hydrochloric acid solution. The precipitate was isolated, washed with water and dried under vacuum at 55° C. There was thus obtained 2-methoxy-3-phenylbenzoic acid (0.395 g); NMR Spectrum: (DMSOd$_6$) 3.4 (s, 3H), 7.25 (t, 1H), 7.4 (m, 6H), 7.62 (d, 1H), 12.92 (br s, 1H).

b) The starting material 3-(4-fluorophenyl)benzoic acid is described in Tetrahedron, 1997, 53, 14437-14450. The product gave the following data: NMR Spectrum: (DMSOd$_6$) 2.02 (s, 3H), 2.32 (s, 3H), 2.42-2.49 (m, 4H), 3.25-3.29 (m, 4H), 7.28-7.38 (m, 2H), 7.41-7.48 (m, 2H), 7.57-7.84 (m, 3H), 7.84-7.88 (m, 5H), 7.92 (d, 1H), 8.06 (s, 1H), 8.19 (s, 1H); Mass Spectrum: M+H$^+$ 548.

c) The starting material 3-(2-furyl)benzoic acid is described in Tetrahedron Letters, 1998, 39, 4175-4178. The product was purified by column chromatography on an isolute SCX ion exchange column using initially methanol and then a 99:1 mixture of methanol and a saturated aqueous ammonium hydroxide solution as eluent and gave the following data:

NMR Spectrum: (DMSOd$_6$) 2.05 (s, 3H), 2.23 (s, 3H), 2.45-2.5 (m, 4H), 3.2-3.35 (m, 4H), 6.62 (s, 1H), 7.06 (s, 1H), 7.42 (d, 1H), 7.48 (s, 1H), 7.57-7.63 (m, 3H), 7.78-7.84 (m, 4H), 7.9 (d, 1H), 8.08 (s, 1H), 8.24 (s, 1H), 10.49 (s, 1H); Mass Spectrum: M+H$^+$ 520.

d) The product gave the following data: NMR Spectrum: (DMSOd$_6$) 1.69-1.8 (m, 6H), 1.84-1.98 (m, 2H), 2.04 (s, 3H), 2.24 (s, 3H), 2.45-2.5 (m, 4H), 3.25-3.29 (m, 4H), 4.86-4.92 (m, 1H), 7.05 (d, 1H), 7.37-7.48 (m, 5H), 7.63 (s, 2H), 7.79 (d, 2H), 8.07 (s, 1H), 10.32 (s, 1H); Mass Spectrum: M+H$^+$ 538.

The 3-cyclopentyloxybenzoic acid used as a starting material was prepared as follows:-

1,1'-Azodicarbonyldipiperidine (6.64 g) was added to a stirred mixture of cyclopentanol (1.59 ml), ethyl 3-hydroxybenzoate (4.37 g), tributylphosphine (6.48 ml) and THF (100 ml) and the resultant mixture was stirred at ambient temperature for 16 hours. The mixture was filtered and the filtrate was evaporated. The residue was purified by column chromatography on silica using isohexane as eluent. There was thus obtained ethyl 3-cyclopentyloxybenzoate (4.3 g); Mass Spectrum: M+H+ 235.

A mixture of a portion (1 g) of the material so obtained, 2N aqueous sodium hydroxide solution (4.27 ml), methanol (20 ml) and water (5 ml) was stirred at ambient temperature for 4 hours. The mixture was evaporated and the residue was partitioned between methylene chloride and water. The aqueous phase was acidified by the addition of 1N aqueous hydrochloric acid solution and extracted with methylene chloride. The organic extract was evaporated. There was thus obtained 3-cyclopentyloxybenzoic acid (0.864 g); NMR Spectrum: (DMSOd$_6$) 1.51-1.75 (m, 6H), 1.8-2.0 (m, 2H), 4.8-4.86 (m, 1H), 7.12 (d, 1H), 7.34-7.49 (m, 2H), 7.46-7.49 (m, 1H), 12.89 (s, 1H).

e) The reaction product was purified by column chromatography on reversed-phase silica using initially water and then decreasingly polar mixtures of methanol and water as eluent. The purified product gave the following data: NMR Spectrum: (DMSOd$_6$) 1.48-1.62 (m, 2H), 1.64-1.78 (m, 4H), 1.8-1.95 (m, 2H), 2.04 (s, 3H), 2.23 (s, 3H), 2.45-2.5 (m, 4H), 3.2-3.35 (m, 4H), 3.81 (s, 3H), 7.06 (d, 1H), 7.39 (d, 1H), 7.48 (d, 2H), 7.57-7.63 (m, 3H), 7.77-7.82 (m, 2H), 8.07 (s, 1H), 10.17 (s, 1H); Mass Spectrum: M+H+ 568.

The 3-cyclopentyloxy-4-methoxybenzoic acid used as a starting material is commercially available from Maybridge International, Tintagel, Cornwall, United Kingdom or may be prepared from ethyl 3-hydroxy-4-methoxybenzoate using analogous procedures to those described in Note d) above for the preparation of 3-cyclopentyloxybenzoic acid.

f) The reaction product was purified by column chromatography on reversed-phase silica using initially water and then decreasingly polar mixtures of methanol and water as eluent. The purified product gave the following data: NMR Spectrum: (DMSOd$_6$) 2.04 (s, 3H), 2.05 (s, 3H), 2.22 (s, 3H), 2.45-2.5 (m, 4H), 3.2-3.35 (m, 4H), 7.38-7.47 (m, 3H), 7.58-7.62 (m, 3H), 7.75-7.81 (m, 3H), 8.05-8.08 (m, 2H), 10.39 (s, 1H); Mass Spectrum: M+H+ 511.

g) The reaction product was purified by column chromatography on reversed-phase silica using initially water and then decreasingly polar mixtures of methanol and water as eluent. The purified product gave the following data: NMR Spectrum: (DMSOd$_6$) 2.02 (s, 3H), 2.22 (s, 3H), 2.43-2.5 (m, 4H), 2.98 (s, 3H), 3.21-3.3 (m, 4H), 7.4-7.48 (m, 2H), 7.52-7.62 (m, 4H), 7.78-7.82 (m, 2H), 7.88 (d, 1H), 7.92 (s, 1H), 8.06 (s, 1H), 10.55 (s, 1H); Mass Spectrum: M+H+ 561.

The 3-(N-methylmethanesulphonamido)benzoic acid used as a starting material was prepared as follows:-

Methanesulphonyl chloride (12.1 ml) was added to a stirred mixture of ethyl 3-aminobenzoate (24.55 g), pyridine (14.42 ml) and methylene chloride (300 ml) and the reaction mixture was stirred at ambient temperature for 18 hours. The mixture was washed in turn with water, 1N aqueous hydrochloric acid solution and water. The organic phase was dried (MgSO$_4$) and evaporated. There was thus obtained ethyl 3-methanesulphonamidobenzoate (35.2 g); NMR Spectrum: (DMSOd$_6$) 1.3 (t, 3H), 3.0 (s, 3H), 4.3 (m, 2H), 7.46 (m, 2H), 7.66 (m, 1H), 7.8 (m, 1H), 9.95 (s, 1H), Mass Spectrum: (M−H)− 242.

Methyl iodide (4.23 ml) was added to a stirred mixture of ethyl 3-methanesulphonamidobenzoate (15 g), caesium carbonate (22.12 g) and DMF (60 ml) and the reaction mixture was stirred at ambient temperature for 18 hours. The mixture was partitioned between ethyl acetate and water. The organic phase was washed with water, dried (MgSO$_4$) and evaporated. There was thus obtained ethyl 3-(N-methylmethanesulphonamido)benzoate (14.87 g); NMR Spectrum: (DMSOd$_6$) 1.32 (t, 3H), 2.95 (s, 3H), 3.26 (s, 3H), 4.32 (m, 2H), 7.55 (t, 1H), 7.68 (m, 1H), 7.87 (m, 1H), 7.92 (m, 1H), Mass Spectrum: (M+H)+ 258.

A mixture of the material so obtained, 10N aqueous sodium hydroxide solution (11.5 ml), ethanol (150 ml) and water (30 ml) was stirred at ambient temperature for 4 hours. The mixture was evaporated and 1N aqueous hydrochloric acid solution (125 ml) was added to the residue resulting in the formation of a white precipitate which was isolated, washed in turn with water and diethyl ether and dried under vacuum at 60° C. There was thus obtained 3-(N-methylmethanesulphonamido)benzoic acid (9.72 g); NMR Spectrum: (DMSOd$_6$) 2.94 (s, 3H), 3.26 (s, 3H), 7.52 (t, 1H), 7.65 (m, 1H), 7.84 (m, 1H), 7.91 (m, 1H), Mass Spectrum: (M−H)− 228.

h) The reaction product was purified by column chromatography on reversed-phase silica using initially water and then decreasingly polar mixtures of methanol and water as eluent. The purified product gave the following data: NMR Spectrum: (DMSOd$_6$) 2.04 (s, 3H), 2.23 (s, 3H), 2.4-2.5 (m, 6H), 3.25-3.29 (m, 4H), 3.53 (t, 2H), 3.81 (t, 2H), 7.39-7.58 (m, 4H), 7.61 (s, 1H), 7.67-7.68 (m, 2H), 7.78-7.79 (m, 2H), 8.07 (s, 1H), 10.43 (s, 1H); Mass Spectrum: M+H+ 573.

The 3-(1,1-dioxidoisothiazolidin-2-yl)benzoic acid used as a starting material was prepared as follows:-

3-Chloropropanesulphonyl chloride (5.1 g) was added dropwise to a stirred mixture of ethyl 3-aminobenzoate (4.5 g), pyridine (2.423 ml), 4-dimethylaminopyridine (0.03 g) and methylene chloride (100 ml) and the reaction mixture was stirred at ambient temperature for 48 hours. The mixture was washed with 2N aqueous hydrochloric acid solution and the organic phase was dried (MgSO$_4$) and evaporated. There was thus obtained ethyl 3-(3-chloropropanesulphonamido)benzoate (8.19 g); NMR Spectrum: (DMSOd$_6$) 1.29 (t, 3H), 2.19 (m, 2H), 3.24 (t, 2H), 3.72 (t, 2H), 4.31 (m, 2H), 7.47 (m, 2H), 7.68 (m, 1H), 7.83 (m, 1H), 10.12 (s, 1H); Mass Spectrum: (M−H)− 303 & 305.

A mixture of the material so obtained, triethylamine (7.3 ml) and ethanol (120 ml) was stirred and heated to reflux for 6 hours. The mixture was evaporated. The residue was partitioned between methylene chloride and water. The organic phase was dried (MgSO$_4$) and evaporated. There was thus obtained ethyl 3-(1,1-dioxidoisothiazolidin-2-yl)benzoate (6.99 g); NMR Spectrum: (DMSOd$_6$) 1.3 (t, 3H), 2.42 (m, 2H), 3.53 (t, 2H), 3.78 (t, 2H), 4.32 (m, 2H), 7.43 (m, 1H), 7.52 (t, 1H), 7.66 (m, 1H), 7.78 (m, 1H), Mass Spectrum: (M+H)+ 269.

A mixture of a portion (6.87 g) of the material so obtained, 10N aqueous sodium hydroxide solution (5.1 ml), ethanol (80 ml) and water (14 ml) was stirred at ambient temperature for 18 hours. The mixture was evaporated and 1N aqueous hydrochloric acid solution (160 ml) was added to the residue resulting in the formation of a white precipitate which was isolated, washed in turn with water and diethyl ether and dried under vacuum at 60° C. There was thus obtained 3-(1,1-dioxidoisothiazolidin-2-yl)benzoic acid (5.45 g); NMR Spectrum: (DMSOd$_6$) 2.43 (m, 2H), 3.5 (t, 2H), 3.78 (t, 2H), 7.39 (m, 1H), 7.48 (t, 1H), 7.66 (m, 1H), 7.78 (m, 1H), 13.06 (s, 1H), Mass Spectrum: (M−H)− 239.

i) The product gave the following data: NMR Spectrum: (DMSOd$_6$) 2.04 (s, 3H), 2.48 (s, 3H), 2.78-2.88 (m, 4H), 3.15-3.19 (m, 4H), 3.28-3.42 (m, 4H), 3.73-3.77 (m, 4H), 7.1-7.18 (m, 1H), 7.35-7.42 (m, 4H), 7.51 (s, 1H), 7.65 (s, 2H), 7.77-7.8 (m, 2H), 8.1 (s, 1H), 10.29 (s, 1H); Mass Spectrum: M+H$^+$ 539.

The 3-morpholinobenzoic acid used as a starting material was prepared as follows:-

A mixture of ethyl 3-bromobenzoate (1.92 ml), morpholine (1.25 ml), 2,2'-bis(diphenylphosphino)-1,1'-binaphthyl (0.336 g), sodium tert-butoxide (1.615 g) and tris(dibenzylideneacetone)dipalladium(0) (0.33 g) and toluene (25 ml) was stirred and heated to 90° C. for 18 hours under argon. The reaction mixture was allowed to cool to ambient temperature and extracted with 1N aqueous hydrochloric acid. The aqueous phase was basified with concentrated sodium hydroxide solution and extracted with ethyl acetate. The organic phase was dried (MgSO$_4$) and evaporated. The residual oil was purified by column chromatography on silica gel using a 47:3 mixture of methylene chloride and methanol as eluent. There was thus obtained N-(3-morpholinobenzoyl)morpholine (0.45 g).

A mixture of the material so obtained, 5M sodium hydroxide solution (2.5 ml) and butanol (2 ml) was stirred and heated to 115° C. for 18 hours. The mixture was evaporated and the residue was acidified by the addition of 1N aqueous hydrochloric acid solution (12.5 ml). The resultant precipitate was isolated, washed with water and dried to give 3-morpholinobenzoic acid (0.15 g); NMR Spectrum: (DMSOd$_6$) 3.1 (t, 4H), 3.73 (t, 4H), 7.19 (d, 1H), 7.32 (d, 1H), 7.38 (t, 1H), 7.42 (s, 1H).

j) The product gave the following data: NMR Spectrum: (DMSOd$_6$) 2.05 (s, 3H), 2.26 (s, 3H), 2.47-2.53 (m, 4H), 3.2-3.3 (m, 4H), 7.42-7.48 (m, 2H), 7.62 (s, 2H), 7.76-7.8 (m, 2H), 7.93-8.07 (m, 4H), 7.93-8.07 (m, 4H), 10.64 (s, 1H); Mass Spectrum: M+H$^+$ 540.

k) The product gave the following data: NMR Spectrum: (DMSOd$_6$) 1.97 (s, 3H), 2.18-2.28 (m, 2H), 2.38 (s, 3H), 2.62-2.78 (m, 4H), 3.2-3.41 (m, 4H), 3.7-3.92 (m, 4H), 5.04-5.14 (m, 1H), 7.14 (d, 1H), 7.39-7.57 (m, 5H), 7.64 (s, 2H), 7.77-7.82 (m, 2H), 8.08 (s, 1H), 10.35 (s, 1H); Mass Spectrum: M+H$^+$ 540.

The 3-tetrahydrofuranyloxybenzoic acid used as a starting material was prepared using analogous procedures to those described in Note d) above except that 3-hydroxytetrahydrofuran was used in place of cyclopentanol.

l) The product gave the following data: NMR Spectrum: (DMSOd$_6$) 2,05 (s, 3H), 2.25 (s, 3H), 2.5 (m, 4H), 3.28 (m, 4H), 3.88 (s, 3H), 7.06 (t, 1H), 7.18 (d, 1H), 7.4 (d, 1H), 7.5 (m, 2H), 7.62 (m, 3H), 7.74-7.81 (m, 2H), 8.1 (s, 1H), 10.29 (s, 1H); Mass Spectrum: M+H$^+$ 484.

m) The product gave the following data: NMR Spectrum: (DMSOd$_6$) 1.34 (t, 3H), 2.05 (s, 3H), 2.25 (s, 3H), 2.5 (m, 4H), 3.25 (m, 4H), 4.08 (q, 2H), 7.14 (m, 1H), 7.39-7.55 (m, 5H), 7.64 (m, 2H), 7.8 (m, 2H), 8.1 (s, 1H), 10.36 (s, 1H); Mass Spectrum: M+H$^+$ 498.

n) The product gave the following data: NMR Spectrum: (DMSOd$_6$) 2.05 (s, 3H), 2.25 (s, 3H), 2.5-3.3 (m, 8H), 6.85 (m, 1H), 7.40-7.55 (m, 3H), 7.65 (m, 3H), 7.8 (m, 3H), 7.98 (m, 1H), 8.1 (s, 1H), 10.55 (s, 1H); Mass Spectrum: M+H$^+$ 570.

o) The product gave the following data: NMR Spectrum: (DMSOd$_6$) 1.86-1.98 (m, 2H), 2.04 (s, 3H), 2.25 (s, 3H), 2.42-2.5 (m, 2H), 2.62-2.66 (m, 2H), 3.15-3.19 (m, 4H), 3.53 (t, 2H), 3.58-3.64 (m, 2H), 3.72-3.76 (m, 4H), 7.1-7.18 (m, 1H), 7.24 (s, 1H), 7.34-7.44 (m, 5H), 7.58 (d, 1H), 7.76-7.82 (m, 2H), 7.96 (s, 1H), 10.29 (s, 1H); Mass Spectrum: M+H$^+$ 553.

p) The product gave the following data: NMR Spectrum: (DMSOd$_6$) 1.86-1.98 (m, 2H), 2.04 (s, 3H), 2.25 (s, 3H), 2.42-2.5 (m, 2H), 2.62-2.66 (m, 2H), 3.19-3.23 (m, 4H), 3.53 (t, 2H). 3.58-3.64 (m, 2H), 3.71-3.75 (m, 4H), 6.98 (d, 1H), 7.12 (d, 1H), 7.24 (s, 1H). 7.28 (s, 1H), 7.32-7.44 (m, 2H), 7.58 (d, 1H), 7.74-7.82 (m, 2H), 7.96 (s, 1H), 10.32 (s, 1H); Mass Spectrum: M+H$^+$ 571.

The 3-fluoro-5-morpholinobenzoic acid used as a starting material was prepared as follows:-

A mixture of ethyl 3-fluoro-5-morpholinobenzoate (*Tetrahedron*, 1999, 55, 13285-13300; 6.7 g), 10M sodium hydroxide solution (13.6 ml), water (13.6 ml) and ethanol (67 ml) was stirred at ambient temperature for 20 hours. The mixture was concentrated by evaporation and the residue was acidified by the addition of concentrated hydrochloric acid. The resultant precipitate was isolated, washed with water and dried to give 3-fluoro-5-morpholinobenzoic acid (5.7 g); NMR Spectrum: (DMSOd$_6$) 3.16 (t, 4H), 3.71 (t, 4H), 7.01 (m, 2H), 7.27 (s, 1H).

q) The product gave the following data: NMR Spectrum: (DMSOd$_6$) 1.86-1.98 (m, 2H), 2.05 (s, 3H), 2.25 (s, 3H), 2.42-2.5 (m, 2H), 2.62-2.66 (m, 2H), 3.24-3.34 (m, 4H), 3.53 (t, 2H), 3.58-3.64 (m, 2H), 3.73-3.77 (m, 4H), 7.24 (s, 1H), 7.32-7.43 (m, 3H), 7.58 (d, 1H), 7.63 (s, 1H), 7.7 (s, 1H), 7.74 (s, 1H), 7.8 (d, 1H), 7.97 (s, 1H), 10.45 (s, 1H); Mass Spectrum: M+H$^+$ 621.

r) The product gave the following data: NMR Spectrum: (DMSOd$_6$) 1.86-1.98 (m, 2H), 2.05 (s, 3H), 2.25 (s, 3H), 2.42-2.5 (m, 2H), 2.62-2.66 (m, 2H), 3.53 (t, 2H), 3.58-3.64 (m, 2H), 6.61 (s, 1H), 7.04 (s, 1H), 7.24 (s, 1H), 7.38 (d, 1H), 7.42 (d, 1H), 7.52-7.6 (m, 2H), 7.78-7.92 (m, 5H), 7.98 (s, 1H), 8.24 (s, 1H), 10.49 (s, 1H); Mass Spectrum: M+H$^+$ 534.

s) The reaction residue was purified by column chromatography on an SCX isolute ion exchange column using initially methanol and then a 99:1 mixture of methanol and a saturated aqueous ammonium hydroxide solution as eluent. The material so obtained was dissolved in acetone and precipitated by the addition of isohexane. The product so obtained gave the following data: NMR Spectrum: (DMSOd$_6$) 2.05 (s, 3H), 2.25 (s, 3H), 3.3-3.4 (m, 4H), 3.7-3.8 (m, 4H), 7.1-7.2 (m, 1H), 7.3-7.5 (m, 7H), 7.75-7.85 (m, 3H), 8.25 (s, 1H), 10.3 (s, 1H); Mass Spectrum: M+H$^+$ 539.

The 3-(5-amino-2-methylphenyl)-8-(4-methylpiperazin-1-yl)-3,4-dihydroquinazolin-4-one used as a starting material was prepared as follows:-

Oxalyl chloride (8.5 ml) was added dropwise to a stirred solution of 3-chloro-2-nitrobenzoic acid (15.1 g) in a mixture of methylene chloride (200 ml) and DMF (a few drops) which had been cooled to 0° C. The mixture was allowed to warm to ambient temperature and was stirred for a further 16 hours. The solvent was evaporated. The residue was dissolved in methylene chloride (300 ml) and added dropwise to a stirred mixture of 2-methyl-5-nitroaniline (10.6 g), triethylamine (27.2 ml) and methylene chloride (300 ml). The resultant mixture was stirred at ambient temperature for 16 hours. The precipitate was isolated, washed in turn with a saturated aqueous sodium bicarbonate solution and diethyl ether and dried under vacuum at 40° C. There was thus obtained N-(2-methyl-5-nitrophenyl)-3-chloro-2-nitrobenzamide (14.2 g); NMR Spectrum: (DMSOd$_6$) 2.37 (s, 3H), 7.57 (d, 1H), 7.8-7.85 (m, 1H), 7.95-8.05 (m, 3H), 8.35 (m, 1H); Mass Spectrum: M+H$^+$335.

A mixture of the material so obtained and N-methylpiperazine (24.5 ml) was stirred and heated to 100° C. for 16 hours. The reaction mixture was cooled to ambient temperature and poured into water. The resultant precipitate was isolated, washed with water and dried under vacuum at 40° C. There was thus obtained N-(2-methyl-5-nitrophenyl)-3-(4-methylpiperazin-1-yl)-2-nitrobenzamide (11.8 g); NMR Spectrum: (DMSOd$_6$) 2.2 (s, 3H), 2.35-2.45 (m, 7H), 2.9-3.0 (m, 4H), 7.5-7.7 (m, 4H), 8.0-8.05 (m, 1H), 8.3 (s, 1H); Mass Spectrum: M+H$^+$ 400.

A mixture of the material so obtained, 10% palladium-on-carbon catalyst (1.2 g) and methanol (600 ml) was stirred under an atmosphere of hydrogen gas until hydrogen uptake ceased. The catalyst was filtered off and the filtrate was evaporated. The material so obtained was purified by column chromatography on silica using a 4:1 mixture of methylene chloride and methanol as eluent. There was thus obtained N-(5-amino-2-methylphenyl)-2-amino-3-(4-methylpiperazin-1-yl)benzamide (7.36 g); NMR Spectrum: (DMSOd$_6$) 2.0 (s, 3H), 2.2 (s, 3H), 2.75-2.85 (m, 4H), 4.85 (s, 2H), 6.0 (s, 2H), 6.35-6.4 (m, 1H), 6.57 (m, 2H), 6.85 (d, 1H), 7.07 (d, 1H), 7.45 (d, 1H), 9.35 (s, 1H); Mass Spectrum: M+H$^+$ 340:

A mixture of a portion (4 g) of the material so obtained, triethyl orthoformate (3.92 ml), glacial acetic acid (0.34 ml) and ethanol (72 ml) was stirred and heated to 80° C. for 2 days. The reaction mixture was cooled and evaporated. The residue was dissolved in water, basified by the addition of sodium bicarbonate and extracted with methylene chloride. The organic extract was evaporated and the residue was purified by column chromatography on silica using a 20:1 mixture of methylene chloride and methanol as eluent. There was thus obtained 3-(5-amino-2-methylphenyl)-8-(4-methylpiperazin-1-yl)-3,4-dihydroquinazolin-4-one (4.1 g); NMR Spectrum: (DMSOd$_6$) 1.85 (s, 3H), 2.2 (s, 3H), 2.5-2.6 (m, 4H), 5.15 (s, 2H), 6.5 (d, 1H), 6.6-6.65 (m, 1H), 7.0 (d, 1H), 7.3 (d, 1H), 7.42 (t, 1H), 7.75 (d, 1H), 8.15 (s, 1H); Mass Spectrum: M+H$^+$ 350.

t) The product gave the following data: NMR Spectrum: (DMSOd$_6$) 2.05 (s, 3H), 2.25 (s, 3H), 3.2-3.25 (m, 4H), 3.7-3.8 (m, 4H), 6.95-7.0 (m, 1H), 7.1-7.15 (m, 1H), 7.3-7.4 (m, 2H), 7.4-7.5 (m, 2H), 7.75-7.8 (m, 3H), 8.25 (s, 1H), 10.33 (s, 1H); Mass Spectrum: M+H$^-$ 557.

u) The product gave the following data: NMR Spectrum: (DMSOd$_6$) 2.05 (s, 3H), 2.25 (s, 3H), 3.7-3.8 (m, 4H), 7.3-7.5 (m, 4H), 7.6-7.85 (m, 5H), 8.25 (s, 1H), 10.48 (s, 1H); Mass Spectrum: M+H$^+$ 607.

v) The product gave the following data: NMR Spectrum: (DMSOd$_6$) 2.05 (s, 3H), 2.25 (s, 3H), 6.6-6.65 (m, 1H), 7.05 (m, 1H), 7.3-7.35 (m, 1H), 7.4-7.5 (m, 2H), 7.5-7.6 (m, 1H), 7.75-7.95 (m, 6H), 8.25-8.3 (m, 2H), 10.5 (s, 1H); Mass Spectrum: M+H$^+$ 520.

w) The product gave the following data: NMR Spectrum: (DMSOd$_6$) 2.05 (s, 3H), 2.25 (s, 3H), 7.3-7.4 (m, 3H), 7.4-7.5 (m, 2H), 7.55-7.65 (m, 1H), 7.75-7.95 (m, 7H), 8.18 (s, 1H), 8.3 (s, 1H), 10.48 (s, 1H); Mass Spectrum: M+H$^+$ 548.

EXAMPLE 12

Using an analogous procedure to that described in Example 1 or Example 2 as appropriate, the appropriate 2-aminobenzamide was reacted with triethyl orthoformate or triethyl orthoacetate to give the compounds described in Table VI.

TABLE VI

| No. | (R$^1$)$_m$ | (R$^2$)$_n$ | R$^3$ | (R)$_p$ | Note |
|---|---|---|---|---|---|
| 1 | 8-morpholino | 4-methyl | H | 3-(4-methylpiperazin-1-yl)methyl | a |
| 2 | 8-morpholino | 4-methyl | methyl | 3-(4-methylpiperazin-1-yl)methyl | b |

Notes a) The reaction mixture was heated to 70° C. for 48 hours. the product gave the following data: NMR Spectrum: (DMSOd$_6$) 2.1 (s, 3H), 2.2-2.45 (m, 11H), 3.5 (s, 2H), 3.7-3.8 (m, 4H), 7.3-7.35 m, 2H), 7.4-7.55 (m, 4H), 7.55-7.6 (m, 1H), 7.8 (d, 1H), 7.8-7.9 (m, 2H), 8.3 (s, 1H), 10.0 (s, 1H); Mass Spectrum: M+H$^+$ 553.

The N-{3-[3-(4-methylpiperazin-1-ylmethyl)benzamido]-4-methylphenyl}-2-amino-3-morpholinobenzamide used as a starting material was prepared as follows:-

3-Chloromethylbenzoyl chloride (24.8 ml) was added to a stirred mixture of 2-methyl-5-nitroaniline (26.6 g), triethylamine (49 ml) and methylene chloride (800 ml) and the mixture was stirred at ambient temperature for 16 hours. The precipitate was isolated, washed with 1N aqueous hydrochloric acid solution and with diethyl ether and dried under vacuum at 40° C. There was thus obtained 3-chloromethyl-N-(2-methyl-5-nitrophenyl)benzamide (43.5 g); NMR Spectrum: (DMSOd$_6$) 2.38 (s, 3H), 2.85 (s, 2H), 7.53-7.58 (m, 2H), 7.67 (d, 1H), 7.95 (d, 1H), 8.01-8.04 (m, 2H), 8.32 (s, 1H), 10.19 (s, 1H); Mass Spectrum: M+H$^+$ 305.

1-Methylpiperazine (8.03 ml) was added to a stirred mixture of a portion (20 g) of the material so obtained, potassium carbonate (18.2 g) and acetone (750 ml) and the mixture was heated to 54° C. and stirred for 16 hours. The resultant solution was evaporated and the residue was dissolved in methylene chloride. The organic solution was washed with water and evaporated. There was thus obtained N-(2-methyl-5-nitrophenyl)-3-(4-methylpiperazin-1-ylmethyl)benzamide (26.4 g); NMR Spectrum: (DMSOd$_6$) 2.06 (s, 3H), 2.12 (s, 3H), 2.31-2.37 (m, 8H), 3.52 (s, 2H), 7.48-7.57 (m, 3H), 7.87 (d, 2H), 8.01 (m, 1H), 8.33 (s, 1H); Mass Spectrum: M+H$^+$ 369.

Iron powder was added to a stirred mixture of a portion (18.0 g) of the material so obtained, ethanol (500 ml), water (50 ml) and acetic acid (10 ml). The resultant mixture was stirred and heated to reflux for 5 hours. Water (50 ml) was added and the mixture was basified by the addition of sodium carbonate. The mixture was filtered and the filtrate was evaporated to dryness. The residue was triturated under water and the resultant solid was isolated and dried under vacuum at 40°

C. There was thus obtained N-(5-amino-2-methylphenyl)-3-(4-methylpiperazin-1-ylmethyl)benzamide (11.1 g); NMR Spectrum: (DMSOd$_6$) 2.03 (s, 3H), 2.13 (s, 3H), 2.24-2.4 (m, 8H), 3.5 (s, 2H), 4.86 (s, 2H) 6.35 (d, 1H), 6.57 (s, 1H), 6.86 (d, 1H), 7.40-7.48 (m, 2H), 7.78-7.83 (m, 2H), 9.57 (s, 1H); Mass Spectrum: M+H$^+$ 339.

Oxalyl chloride (0.83 ml) was added to a mixture of 3-chloro-2-nitrobenzoic acid (1.45 g), methylene chloride (30 ml) and a few drops of DMF which had been cooled to 0° C. The reaction mixture was stirred at ambient temperature for 4 hours. The mixture was evaporated. The residue was dissolved in methylene chloride (10 ml) and a portion (5 ml) of the solution was added to a mixture of N-(5-amino-2-methylphenyl)-3-(4-methylpiperazin-1-ylmethyl)benzamide (1.01 g), triethylamine (1 ml) and methylene chloride (20 ml). The resultant mixture was stirred at ambient temperature for 16 hours. The mixture was evaporated and the residue was partitioned between methylene chloride and a saturated aqueous sodium bicarbonate solution. The organic phase was dried (MgSO$_4$) and evaporated. There was thus obtained N-{3-[3-(4-methylpiperazin-1-ylmethyl)benzamido]-4-methylphenyl}-3-chloro-2-nitrobenzamide (1.69 g); NMR Spectrum: (DMSOd$_6$) 2.15 (s, 3H), 2.2 (s, 3H), 2.2-2.4 (m, 8H), 3.5 (s, 2H), 7.2-7.3 (m, 1H), 7.4-7.5 (m, 3H), 7.7-7.95 (m, 6H), 9.9 (s, 1H), 10.78 (s, 1H); Mass Spectrum: M+H$^+$ 522.

A mixture of the material so obtained and morpholine (2.71 ml) was stirred and heated to 105° C. for 16 hours. The mixture was cooled to ambient temperature and poured into water. The precipitate was isolated, washed with water and partitioned between a saturated aqueous sodium bicarbonate solution and methylene chloride. The organic phase was dried (MgSO$_4$) and evaporated. There was thus obtained N-{3-[3-(4-methylpiperazin-1-ylmethyl)benzamido]-4-methylphenyl}-2-nitro-3-morpholinobenzamide (1.47 g); NMR Spectrum: (DMSOd$_6$) 2.15 (s, 3H), 2.2 (s, 3H), 2.2-2.45 (m, 8H), 2.85-2.95 (m, 4H), 3.5 (s, 2H), 3.6-3.7 (m, 4H), 7.2 (d, 1H), 7.4-7.5 (m, 3H), 7.5-7.6 (m, 1H), 7.6-7.7 (m, 2H), 7.75 (s, 1H), 7.8-7.9 (m, 2H), 9.9 (s, 1H), 10.62 (s, 1H); Mass Spectrum: M+H$^+$ 573.

A mixture of the material so obtained, iron powder (1.435 g), ethanol (25.7 ml), water (2.57 ml) and glacial acetic acid (0.52 ml) was stirred and heated to 95° C. for 8 hours. The resultant mixture was cooled to ambient temperature and basified to pH9 by the addition of sodium bicarbonate. The mixture was filtered and the filtrate was evaporated. The residue was partitioned between ethyl acetate and a saturated aqueous sodium bicarbonate solution. The organic phase was dried (MgSO$_4$) and evaporated. The material so obtained was dissolved in ethyl acetate and precipitated by the addition of isohexane. The solid was isolated. There was thus obtained N-{3-[3-(4-methylpiperazin-1-ylmethyl)benzamido]-4-methylphenyl}-2-amino-3-morpholinobenzamide (0.95 g); NMR Spectrum: (DMSOd$_6$) 2.1 (s, 3H), 2.2 (s, 3H), 2.2-2.4 (m, 8H), 2.75-2.8 (m, 4H), 3.5 (s, 2H), 3.7-3.8 (m, 4H), 6.05 (s, 2H), 6.6 (t, 1H), 7.1 (d, 1H), 7.2 (d, 1H), 7.4-7.5 (m, 4H), 7.8 (d, 1H), 7.8-7.9 (m, 2H), 9.85 (s, 1H), 9.95 (s, 1H); Mass Spectrum: M+H$^+$ 543.

b) The reaction mixture was heated to 70° C. for 48 hours. The product gave the following data: NMR Spectrum: (DMSOd$_6$) 2.1 (s, 3H), 2.2 (s, 3H), 2.2-2.4 (m, 11H), 3.5 (s, 2H), 3.7-3.85 (m, 4H), 7.2-7.3 (m, 2H), 7.3-7.5 (m, 5H), 7.65 (d, 1H), 7.8-7.9 (m, 2H), 10.0 (s, 1H); Mass Spectrum: M+H$^+$ 567.

EXAMPLE 13

Using an analogous procedure to that described in Example 1 or Example 2 as appropriate, the appropriate 2-aminobenzamide was reacted with triethyl orthoformate or triethyl orthoacetate to give the compounds described in Table VII. In each case the reaction product was purified by column chromatography on an isolute SCX ion exchange column using initially methanol and then a 99:1 mixture of methanol and a saturated aqueous ammonium hydroxide solution as eluent.

TABLE VII

| No. | (R$^1$)$_m$ | R$^3$ | (R)$_p$ | Note |
|---|---|---|---|---|
| 1 | 6-(4-methylpiperazin-1-yl) | methyl | 3-fluoro-5-morpholino | a |
| 2 | 6-(4-methylpiperazin-1-yl) | H | 3-fluoro-5-morpholino | b |
| 3 | 6-[N-(3-dimethylaminopropyl)-N-methylamino] | methyl | 3-fluoro-5-morpholino | c |
| 4 | 6-[N-(3-dimethylaminopropyl)-N-methylamino] | H | 3-fluoro-5-morpholino | d |
| 5 | 6-(3-dimethylaminopropylamino) | methyl | 3-fluoro-5-morpholino | e |
| 6 | 6-(3-dimethylaminopropylamino) | H | 3-fluoro-5-morpholino | f |
| 7 | 6-[N-(3-methylaminopropyl)-N-methylamino] | methyl | 3-fluoro-5-morpholino | g |
| 8 | 6-[N-(3-methylaminopropyl)-N-methylamino] | H | 3-fluoro-5-morpholino | h |

Notes a) The product gave the following data: Mass Spectrum: M+H$^+$591.

The 3-[2-amino-5-(4-methylpiperazin-1-yl)benzamido]-4-chloro-N-(3-fluoro-5-morpholinophenyl)benzamide used as a starting material was prepared as follows:-

A mixture of 3,5-difluoronitrobenzene (31.1 g) and morpholine (85.2 g) was stirred and heated at 100° C. for 66 hours. The mixture was evaporated and the residue was purified by column chromatography on silica gel using a 4:1 mixture of isohexane and ethyl acetate as eluent. There was thus obtained 3-fluoro-5-morpholinonitrobenzene (33.3 g); NMR Spectrum: (DMSOd$_6$) 3.2-3.3 (m, 4H), 3.6-3.8 (m, 4H), 7.25 (m, 1H), 7.37 (m, 1H), 7.5 (m, 1H).

A mixture of the material so obtained, 10% palladium-on-carbon (3.3 g) and ethanol (1400 ml) was stirred under an atmosphere pressure of hydrogen gas for 16 hours. The mixture was filtered and the filtrate was evaporated to give 3-fluoro-5-morpholinoaniline (27.5 g); NMR Spectrum: (DMSOd$_6$) 2.9-3.05 (m, 4H), 3.6-3.7 (m, 4H), 5.15 (s, 2H), 5.75-5.9 (m, 3H).

A solution of 4-chloro-3-nitrobenzoyl chloride (41.2 g) in methylene chloride (120 ml) was added to a mixture of 3-fluoro-5-morpholinoaniline (27 g), triethylamine (52.6 ml) and methylene chloride (600 ml) which had been cooled in an ice-bath. The resultant mixture was stirred at ambient temperature for 16 hours. The mixture was evaporated. Methylene chloride and a saturated aqueous sodium bicarbonate solution were added and the resultant precipitate was isolated, washed with diethyl ether and dried under vacuum. There was thus obtained 4-chloro-3-nitro-N-(3-fluoro-5-morpholinophenyl)benzamide (36.1 g); NMR Spectrum: (DMSOd$_6$) 3.05-3.15 (m, 4H), 3.7-3.75 (m, 4H), 6.5-6.6 (m, 1H), 7.1-7.2 (m, 2H), 7.95 (d, 1H), 8.2-8.3 (m, 1H), 8.6 (s, 1H).

A mixture of the material so obtained, iron powder (50.6 g), glacial acetic acid (19 ml), water(95 ml) and ethanol (600 ml) was stirred and heated to reflux for 6 hours. The mixture was cooled to ambient temperature and water was added. The mixture was carefully basified to pH9 by the addition of a saturated aqueous sodium bicarbonate solution and extracted with ethyl acetate. The organic phase was dried over magnesium sulphate and evaporated to give 3-amino-4-chloro-N-(3-fluoro-5-morpholinophenyl)benzamide (24.3 g); NMR Spectrum: (DMSOd$_6$) 3.0-3.1 (m, 4H), 3.7-3.75 (m, 4H), 5.6 (s, 1H), 6.45-6.55 (m, 1H), 7.0-7.2 (m, 3H), 7.3-7.35 (m, 2H), 10.09 (br s, 1H); Mass Spectrum: M+H$^+$350.

Oxalyl chloride (1.05 ml) was added dropwise to a stirred mixture of 5-chloro-2-nitrobenzoic acid (2.08 g), methylene chloride (100 ml) and DMF (a few drops) which had been cooled to 0° C. The mixture was allowed to warm to ambient temperature and was stirred for 4 hours. The mixture was evaporated and the residue was dissolved in methylene chloride (10 ml) and added dropwise to a stirred mixture of 3-amino-4-chloro-N-(3-fluoro-5-morpholinophenyl)benzamide (3.0 g) and pyridine (40 ml). The resultant mixture was heated at 80° C. for 16 hours. The solvent was evaporated and the residue was dissolved in methylene chloride (50 ml) and water (50 ml) and stirred for one hour. The resultant solid was filtered, washed with water and diethyl ether and dried under vacuum at 40° C. There was thus obtained 4-chloro-3-(5-chloro-2-nitrobenzamido)-N-(3-fluoro-5-morpholinophenyl)benzamide (1.07 g); NMR Spectrum: (DMSOd$_6$) 3.09-3.14 (m, 4H), 3.69-3.74 (m, 4H), 6.58 (d, 1H), 7.15-7.2 (m, 2H), 7.71 (d, 1H), 7.82-7.92 (m, 3H), 8.2 (d, 1H), 8.29 (s, 1H), 10.37 (s, 1H), 10.61 (s, 1H); Mass Spectrum: M+H$^+$533 and 535.

A portion (0.8 g) of the material so obtained was dissolved in 1-methylpiperazine (3 ml) and the mixture was stirred and heated to 100° C. for 16 hours. The mixture was cooled and poured into water. The resultant solid was isolated, washed in turn with water and diethyl ether and dried under vacuum at 40° C. There was thus obtained 4-chloro-N-(3-fluoro-5-morpholinophenyl)-3-[5-(4-methylpiperazin-1-yl)-2-nitrobenzamido]benzamide (0.803 g); NMR Spectrum: (DMSOd$_6$) 2.21 (s, 3H), 2.4-2.45 (m, 4H), 3.08-3.13 (m, 4H), 3.46-3.5 (m, 4H), 3.69-3.74 (m, 4H), 6.58 (d, 1H), 6.84 (s, 1H), 7.0-7.2 (m, 4H), 7.68 (d, 1H), 7.80 (d, 1H), 8.04 (d, 1H), 8.36 (s, 1H); Mass Spectrum: M+H$^+$597.

Iron powder (0.726 g) was added to a stirred suspension of 4-chloro-N-(3-fluoro-5-morpholinophenyl)-3-[5-(4-methylpiperazin-1-yl)-2-nitrobenzamido]benzamide (0.76 g), water (2 ml), acetic acid (0.5 ml) and ethanol (15 ml) and the resultant mixture was stirred and heated to reflux for 1 hour. The mixture was cooled to ambient temperature. Water (80 ml) was added and the mixture was basified by the addition of sodium carbonate. The resultant mixture was filtered through diatomaceous earth and the separated solids were washed in turn with methylene chloride and methanol. The combined filtrates were evaporated and the residue was triturated under ethyl acetate. The mixture was filtered and the filtrate was evaporated to give 3-[2-amino-5-(4-methylpiperazin-1-yl)benzamido]-4-chloro-N-(3-fluoro-5-morpholinophenyl)benzamide (0.385 g); Mass Spectrum: M+H$^+$567.

b) The product gave the following data: Mass Spectrum: M+H$^+$577.

c) The product gave the following data: NMR Spectrum: (DMSOd$_6$) 1.6-1.7 (m, 2H), 2.09 (s, 3H), 2.11 (s, 6H), 2.21 (t, 2H), 2.96 (s, 3H), 3.06-3.14 (m, 4H), 3.37-3.43 (m, 2H), 3.69-3.8 (m, 4H), 6.56 (d, 1H), 7.09 (s, 1H), 7.15-7.19 (m, 2H) 7.32-7.38 (m, 1H), 7.53 (d, 1H), 7.9 (d, 1H), 8.09 (d, 1H), 8.16 (s, 1H), 10.31 (s, 1H); Mass Spectrum: M+H$^+$ 607.

The 3-{2-amino-5-[N-(3-dimethylaminopropyl)-N-methylamino]benzamido]-4-chloro-N-(3-fluoro-5-morpholinophenyl)benzamide used as a starting material was prepared as follows:-

A mixture of 4-chloro-3-(5-chloro-2-nitrobenzamido)-N-(3-fluoro-5-morpholinophenyl)benzamide (0.8 g) and N-(3-dimethylaminopropyl)-N-methylamine (3 ml) was stirred and heated to 100° C. for 16 hours. The mixture was cooled and poured into water. The resultant solid was isolated, washed in turn with water and-diethyl ether and dried under vacuum at 40° C. There was thus obtained 4-chloro-3-{5-[N-(3-dimethylaminopropyl)-N-methylamino]-2-nitrobenzamido}-N-(3-fluoro-5-morpholinophenyl)benzamide; NMR Spectrum: (DMSOd$_6$) 1.62-1.74 (m, 2H), 2.12 (s, 6H), 2.21 (t, 2H), 3.08 (s, 3H), 3.1-3.13 (m, 4H), 3.52 (t, 2H), 3.71-3.74 (m, 4H), 6.68 (d, 1H), 6.78 (s, 1H), 6.84 (d, 1H), 7.16-7.20 (m, 2H), 7.68 (d, 1H), 7.82 (d, 1H), 8.04 (d, 1H), 8.31 (s, 1H); Mass Spectrum M+H$^+$ 613 and 615.

Using an analogous procedure to that described in the last paragraph of the portion of Note a) immediately above which is concerned with the preparation of starting materials, 4-chloro-3-{5-[N-(3-dimethylaminopropyl)-N-methylamino]-2-nitrobenzamido}-N-(3-fluoro-5-morpholinophenyl)-benzamide was reduced to give 3-{2-amino-5-[N-(3-dimethylaminopropyl)-N-methylamino]benzamido]-4-chloro-N-(3-fluoro-5-morpholinophenyl)benzamide; NMR Spectrum: (DMSOd$_6$) 1.54-1.62 (m, 2H), 2.1 (s, 6H), 2.18-2.22 (m, 2H), 2.77 (s, 3H), 3.09-3.16 (m, 4H), 3.18-3.22 (m, 2H), 3.7-3.74 (m, 4H), 6.57 (d, 1H), 6.7 (d, 1H), 6.84 (d, 1H), 7.08-7.24 (m, 3H), 7.7 (d, 1H), 7.8 (d, 1H), 8.27 (s, 1H); Mass Spectrum: M+H$^+$583.

d) The product gave the following data: Mass Spectrum: M+H$^+$593.

e) The product gave the following data: Mass Spectrum: M+H$^+$593.

The 3-[2-amino-5-(3-dimethylaminopropylamino)benzamido]-4-chloro-N-(3-fluoro-5-morpholinophenyl)benzamide used as a starting material was prepared as follows:-

Using an analogous procedure to that described in the sixth paragraph of the portion of Note a) immediately above which is concerned with the preparation of starting materials, 4-chloro-3-(5-chloro-2-nitrobenzamido)-N-(3-fluoro-5-morpholinophenyl)benzamide was reacted with 3-dimethylaminopropylamine to give 4chloro-3-[5-(3-dimethylaminopropylamino)-2-nitrobenzamido]-N-(3-fluoro-5-morpholinophenyl)benzamide in 76% yield; NMR Spectrum: (DMSOd$_6$) 1.62-1.74 (m, 2H). 2.12 (s, 6H), 2.27 (t, 2H), 3.08-3.13 (m, 4H), 3.18-3.22 (m, 2H), 3.69-3.74 (m, 4H), 6.58 (d, 1H), 6.67 (m, 2H), 7.15-7.2 (m, 2H), 7.42 (t, 1H), 7.69 (d, 1H), 7.68 (d, 1H), 7.82 (d, 1H), 8.04 (d, 1H), 8.26 (s, 1H), 10.32 (s, 1H); Mass Spectrum: M+H$^+$599.

Using an analogous procedure to that described in the last paragraph of the portion of Note a) immediately above which is concerned with the preparation of starting materials, 4-chloro-3-[5-(3-dimethylaminopropylamino)-2-nitrobenzamido]-N-(3-fluoro-5-morpholinophenyl)benzamide was reduced to give the required starting material; NMR Spectrum: (DMSOd$_6$) 1.62-1.78 (m, 2H), 2.15 (s, 6H), 2.33 (t, 2H), 2.99 (t, 2H), 3.09-3.13 (m, 4H), 3.69-3.74 (m, 4H), 6.56 (d, 1H), 6.66 (s, 2H), 6.94 (s, 1H), 7.15-7.22 (m, 3H), 7.68 (d, 1H), 7.78 (d, 1H), 8.32 (s, 1H), 10.29 (s, 1H); Mass Spectrum: M+H$^+$569.

f) The product gave the following data: Mass Spectrum: M+H$^+$579.

g) The product gave the following data: Mass Spectrum: M+H$^+$593.

The 3-{2-amino-5-[N-(3-methylaminopropyl)-N-methylamino]benzamido]-4-chloro-N-(3-fluoro-5-morpholinophenyl)benzamide used as a starting material was prepared as follows:-

Using an analogous procedure to that described in the sixth paragraph of the portion of Note a) immediately above which is concerned with the preparation of starting materials, 4-chloro-3-(5-chloro-2-nitrobenzamido)-N-(3-fluoro-5-morpholinophenyl)benzamide was reacted with N-(3-methylaminopropyl)-N-methylamine to give 4-chloro-3-(5-chloro-2-nitrobenzamido)-N-(3-fluoro-5-morpholinophenyl)benzamide; NMR Spectrum: (DMSOd$_6$) 1.62-1.74 (m, 2H), 2.25 (s, 3H), 2.46-2.49 (m, 2H), 3.07 (s, 3H), 3.12 (t, 2H), 3.55 (t, 2H), 3.69-3.74 (m, 4H), 6.58 (d, 1H), 6.79 (s, 1H), 6.86 (d, 1H), 7.16-7.2 (m, 2H), 7.69 (d, 1H), 7.82 (d, 1H), 8.12 (s, 1H); Mass Spectrum: M+H$^+$599.

Using an analogous procedure to that described in the last paragraph of the portion of Note a) immediately above which is concerned with the preparation of starting materials, 4-chloro-N-(3-fluoro-5-morpholinophenyl)-3-{5-[N-(3-methylaminopropyl)-N-methylamino]-2-nitrobenzamido}benzamide was reduced to give 3-{2-amino-5-[N-(3-methylaminopropyl)-N-methylamino]benzamido]-4-chloro-N-(3-fluoro-5-morpholinophenyl)benzamide; Mass Spectrum: M+H$^+$569 and 571.

h) The product gave the following data: Mass Spectrum: M+H$^+$579.

EXAMPLE 14

3-{3-[N-(3-fluoro-5-morpholinophenyl)carbamoyl]phenyl}-8-[N-(3-dimethylaminopropyl)-N-methylamino]-3,4-dihydroquinazolin-4-one Using an analogous procedure to that described in Example 1, 3-{2-amino-3-[N-(3-dimethylaminopropyl)-N-methylamino]benzamido]-N-(3-fluoro-5-morpholinophenyl)benzamide was reacted with triethyl orthoformate. The reaction product was purified by column chromatography on an isolute SCX ion exchange column using initially methanol and then a 99:1 mixture of methanol and a saturated aqueous ammonium hydroxide solution as eluent. There was thus obtained the title compound Mass Spectrum: M+H$^+$559.

The 3-{2-amino-3-[N-(3-dimethylaminopropyl)-N-methylamino]benzamido]-N-(3-fluoro-5-morpholinophenyl)benzamide used as a starting material was prepared as follows:-

Oxalyl chloride (0.51 g) was added dropwise to a stirred mixture of 3-chloro-2-nitrobenzoic acid (0.694 g), methylene chloride (50 ml) and DMF (a few drops) which had been cooled to 0° C. The mixture was allowed to warm to ambient temperature and was stirred for 4 hours. The mixture was evaporated and the residue was dissolved in methylene chloride (10 ml) and added dropwise to a stirred mixture of 3-amino-4-chloro-N-(3-fluoro-5-morpholinophenyl)benzamide (1.0 g) and pyridine (20 ml). The resultant mixture was heated at 80° C. for 16 hours. The solvent was evaporated and the residue was dissolved in methylene chloride (50 ml) and water (50 ml) and stirred for one hour. The resultant solid was filtered, washed with water and diethyl ether and dried under vacuum at 40° C. There was thus obtained 4-chloro-3-(3-chloro-2-nitrobenzamido)-N-(3-fluoro-5-morpholinophenyl)benzamide (1.07 g); NMR Spectrum: (DMSOd$_6$) 3.09-3.13 (m, 4H), 3.5-3.74 (m, 4H), 6.48 (d, 1H), 7.14-7.21 (m, 2H), 7.63 (d, 1H), 7.7-7.77 (m, 2H), 7.89 (d, 1H), 8.04 (d, 1H), 8.14 (s, 1H), 10.27 (s, 1H), 10.8 (s, 1H); Mass Spectrum: M+H$^+$533 and 535.

A mixture of 4-chloro-3-(3-chloro-2-nitrobenzamido)-N-(3-fluoro-5-morpholinophenyl)benzamide (0.51 g) and N-(3-dimethylaminopropyl)-N-methylamine (2 ml) was stirred and heated to 100° C. for 16 hours. The mixture was cooled and poured into water. The resultant solid was isolated, washed in turn with water and diethyl ether and dried under vacuum at 40° C. There was thus obtained 4-chloro-3-{3[N-(3-dimethylaminopropyl)-N-methylamino]-2-nitrobenzamido}-N-(3-fluoro-5-morpholinophenyl)benzamide (0.45 g); NMR Spectrum: (DMSOd$_6$) 1.48-1.58 (m, 2H), 2.07 (s, 6H), 2.15 (t, 2H), 2.69 (s, 3H), 3.03 (t, 2H), 3.08-3.15 (m, 4H), 3.7-3.75 (m, 4H), 6.74 (d, 1H), 7.15-7.2 (m, 2H), 7.44 (d, 1H), 7.52-7.64 (d, 2H), 7.7 (d, 1H), 7.82 (d, 1H), 8.08 (s, 1H), 10.32 (s, 1H); Mass Spectrum: M+H$^+$613 and 615.

A mixture of a portion (0.25 g) of the material so obtained, 10% palladium-on-carbon (0.025 g) and methanol (25 ml) was stirred under an atmosphere of hydrogen gas. After cessation of hydrogen uptake, the catalyst was removed by filtration through diatomaceous earth and the filtrate was evaporated. The reaction product was purified by column chromatography on an isolute SCX ion exchange column using initially methanol and then a 99:1 mixture of methanol and a saturated aqueous ammonium hydroxide solution as eluent. There was thus obtained 3-{2-amino-3-[N-(3-dimethylaminopropyl)-N-methylamino]benzamido]-N-(3-fluoro-5-morpholinophenyl)benzamide (0.102 g); NMR Spectrum: (DMSOd$_6$) 1.58-1.62 (m, 2H), 2.09 (s, 6H), 2.25 (t, 2H), 2.56 (s, 3H), 2.77 (t, 2H), 3.09-3.13 (m, 6H), 3.7-3.73 (m, 4H), 6.39 (s, 1H), 6.48-6.64 (m, 3H), 7.08-7.24 (m, 4H), 7.4-7.5 (m, 1H), 7.62 (d, 1H), 7.92 (d, 1H) 8.26 (s, 1H), 10.14 (s, 1H), 10.22 (s, 1H); Mass Spectrum: M+H$^+$549.

EXAMPLE 15

3-[5-(2-Chloropyrid-4-ylcarbonylamino)-2-methylphenyl]-6-(4-methylhomopiperazin-1-yl)-3,4-dihydroquinazolin-4-one Using an analogous procedure to that described in Example 5, 3-(5-amino-2-methylphenyl)-6-(4-methylhomopiperazin-1-yl)-3,4-dihydroquinazolin-4-one was reacted with 2-chloropyridine-4-carbonyl chloride to give the title compound; NMR Spectrum: (DMSOd$_6$) 1.84-1.96 (m, 2H), 2.06 (s, 3H), 2.29 (s, 3H), 2.42-2.49 (m, 2H), 2.62-2.68 (m, 2H), 3.53 (t, 2H), 3.58-3.64 (m, 2H), 7.22 (d, 1H), 7.34 (m, 1H), 7.44 (m, 1H), 7.58 (d, 1H), 7.73-7.78 (m, 2H), 7.82-7.86 (m, 1H), 7.96-7.98 (m, 2H), 8.50-8.62 (m, 1H), 10.68 (s, 1H); Mass Spectrum: M+H$^+$503 & 505.

The 3-(5-amino-2-methylphenyl)-6-(4-methylhomopiperazin-1-yl)-3,4-dihydroquinazolin-4-one used as a starting material was prepared as follows:-

A mixture of N-(2-methyl-5-nitrophenyl)-5-chloro-2-nitrobenzamide (5 g), N-methylhomopiperazine (9.28 ml) and DMSO (4 ml) was stirred and heated to 80° C. for 4 hours. The reaction mixture was cooled to ambient temperature and poured into water. The resultant precipitate was isolated, washed with water and with diethyl ether and dried under vacuum at 40° C. There was thus obtained N-(2-methyl-5-nitrophenyl)-5-(4-methylhomopiperazin-1-yl)-2-nitrobenzamide (5.42 g); NMR Spectrum: (DMSOd$_6$) 1.82-1.96 (m, 2H), 2.26 (s, 3H), 2.38 (s, 3H), 2.42-2.52 (m, 2H), 2.61-2.65 (m, 2H), 3.59-3.63 (m, 2H), 3.67-3.71 (m, 2H), 6.84-6.93 (m, 2H), 7.52 (d, 1H), 7.98 (d, 1H), 8.05 (d, 1H), 8.55 (s, 1H), 10.13 (s, 1H); Mass Spectrum: M+H$^+$414.

A mixture of the material so obtained, 10% palladium-on-carbon catalyst (0.54 g) and methanol (150 ml) was stirred under an atmosphere of hydrogen gas until hydrogen uptake ceased. The catalyst was filtered off and the filtrate was evaporated. There was thus obtained N-(5-amino-2-methylphenyl)-2-amino-5-(4-methylhomopiperazin-1-yl)benzamide (3.64 g); NMR Spectrum: (DMSOd$_6$) 1.8-1.92 (m, 2H), 2.04 (s, 3H), 2.25 (s, 3H), 2.42-2.48 (m, 2H), 2.57-2.60 (m, 2H), 3.34-3.39 (m, 2H), 3.4-3.45 (m, 2H), 4.85 (s, 2H), 5.46 (s, 2H), 6.37 (d, 1H), 6.62-6.74 (m, 3H), 6.84 (d, 1H), 6.94 (s, 1H), 9.46 (d, 1H); Mass Spectrum: M+H$^+$354.

A mixture of the material so obtained, triethyl orthoformate (3.41 ml), glacial acetic acid (0.3 ml) and ethanol (75 ml) was stirred and heated to 70° C. for 16 hours. A 1N aqueous hydrochloric acid solution (20.6 ml) was added and the mixture was stirred at 60° C. for 3 hours. The resultant mixture was evaporated. The residue was dissolved in water, basified by the addition of sodium bicarbonate and extracted with methylene chloride. The organic extract was evaporated to give 3-(5-amino-2-methylphenyl)-6-(4-methylhomopiperazin-1-yl)-3,4-dihydroquinazolin-4-one (3.78 g); NMR Spectrum: (DMSOd$_6$) 1.86 (s, 3H), 1.89-1.92 (m, 2H), 2.24 (s, 3H), 2.44-2.49 (m, 2H), 2.6-2.63 (m, 2H), 3.49-3.53 (m, 2H), 3.58-3.62 (m, 2H), 5.14 (s, 2H), 6.46 (s, 1H), 6.6 (d, 1H), 7.01 (d, 1H), 7.22 (s, 1H), 7.32 (d, 1H), 7.55 (d, 1H), 7.86 (s, 1H); Mass Spectrum: M+H$^+$364.

EXAMPLE 16

3-[5-(3,5-Difluorobenzamido)-2-methylphenyl]-6-(4-methylhomopiperazin-1-yl)-3,4-dihydroquinazolin-4-one Using an analogous procedure to that described in Example 5, 3-(5-amino-2-methylphenyl)-6-(4-methylhomopiperazin-1-yl)-3,4dihydroquinazolin-4-one was reacted with 3;5-difluorobenzoyl chloride to give the title compound; NMR Spectrum: (DMSOd$_6$) 1.84-1.96 (m, 2H), 2.05 (s, 3H), 2.25 (s, 3H), 2.42-2.5 (m, 2H), 2.62-2.64 (m, 2H), 3.53 (t, 2H), 3.58-3.64 (m, 2H), 7.24 (d, 1H), 7.38 (m, 1H), 7.40-7.44 (m, 1H), 7.48-7.54 (m, 1H), 7.58 (d, 1H), 7.64-7.67 (m, 2H), 7.75-7.78 (m, 2H), 7.96 (s, 1H), 10.49 (s, 1H); Mass Spectrum: M+H$^+$504.

EXAMPLE 17

Using an analogous procedure to that described in Example 10, the appropriate 3-(5-amino-2-methylphenyl)-3,4-dihydroquinazolin-4-one was reacted with the appropriate carboxylic acid to give the compounds described in Table VIII.

TABLE VIII

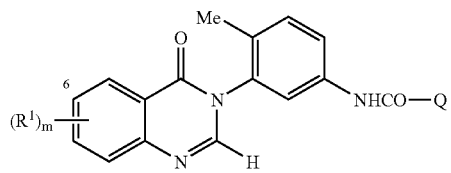

| No. | (R$^1$)$_m$ | Q | Note |
|---|---|---|---|
| 1 | 6-(4-methylpiperazin-1-yl) | 1-fluorenyl | a |
| 2 | 6-(4-methylpiperazin-1-yl) | 3,4-methylenedioxyphenyl | b |
| 3 | 6-(4-methylpiperazin-1-yl) | 3,4-trimethylenedioxyphenyl | c |
| 4 | 6-(4-methylpiperazin-1-yl) | 2,3-dihydrobenzofuran-7-yl | d |
| 5 | 6-(4-methylpiperazin-1-yl) | 2-methyl-2,3-dihydrobenzofuran-7-yl | e |
| 6 | 6-(4-methylpiperazin-1-yl) | 2,2-dimethylchroman-6-yl | f |
| 7 | 6-(4-methylhomopiperazin-1-yl) | dibenzofuran-4-yl | g |
| 8 | 6-(4-methylhomopiperazin-1-yl) | 1-fluorenyl | h |
| 9 | 6-(4-methylpiperazin-1-yl) | 5-(3-chlorophenyl)furan-2-yl | i |
| 10 | 6-(4-methylpiperazin-1-yl) | 5-(4-chlorophenyl)furan-2-yl | j |
| 11 | 6-(4-methylpiperazin-1-yl) | 5-(4-chlorophenyl)thien-2-yl | k |
| 12 | 6-(4-methylpiperazin-1-yl) | 4-(4-chlorophenyl)thien-2-yl | l |
| 13 | 6-(4-methylpiperazin-1-yl) | 4-(4-methoxyphenyl)thien-2-yl | m |
| 14 | 6-(4-methylpiperazin-1-yl) | 3-phenylisothiazol-5-yl | n |
| 15 | 8-(4-methylpiperazin-1-yl) | dibenzofuran-4-yl | o |
| 16 | 8-(4-methylpiperazin-1-yl) | 1-fluorenyl | p |
| 17 | 6-piperazin-1-yl | 1-fluorenyl | q |
| 18 | 6-piperazin-1-yl | dibenzofuran-4-yl | r |

Notes a) The product gave the following data: NMR Spectrum: (DMSOd$_6$) 2.05 (s, 3H), 2.23 (s, 3H), 2.47-2.5 (m, 4H), 3.2-3.3 (m, 4H), 4.18 (s, 2H), 7.3-7.48 (m, 4H), 7.5-7.63 (m, 4H), 7.75 (d, 1H), 7.8 (d, 1H), 7.87 (s, 1H), 7.95 (d, 1H), 8.08-8.11 (m, 2H), 10.49 (s, 1H); Mass Spectrum: M+H$^+$542.

b) The product gave the following data: NMR Spectrum: (DMSOd$_6$) 2.05 (s, 3H), 2.25 (s, 3H), 2.50 (m, 4H), 3.26 (m, 4H), 6.12 (s, 2H), 7.06 (d, 1H), 7.41 (d, 1H), 7.49 (d, 2H), 7.58(m, 1H), 7.65 (d, 2H), 7.88 (m, 2H), 8.08 (s, 1H), 10.23 (s, 1H); Mass Spectrum: M+H$^+$498.

c) The product gave the following data: NMR Spectrum: (DMSOd$_6$) 2.05 (s, 3H), 2.15 (m, 2H), 2.25 (s, 3H), 2.5-3.35 (m, 8H), 4.2 (m, 4H), 7.6 (d, 1H), 7.4 (d, 1H)7.48 (s, 1H), 7.55-7.65(m, 4H), 7.76-7.85 (m, 2H), 8.1 (s,1H), 10.26 (s, 1H); Mass Spectrum: M+H$^+$526.

d) The product gave the following data: NMR Spectrum: (DMSOd$_6$) 2.05 (s, 3H), 2.3 (s, 3H), 2.55 (m, 4H), 3.25 (m 2H), 3.3 (m, 4H), 4.75 (t, 2H), 6.98 (m, 1H) 7.39-7.49 (m, 3H), 7.58-7.65 (m, 3H), 7.8 (m, 2H), 8.1 (s, 1H), 9.9 (s, 1H); Mass Spectrum: M+H$^+$496.

e) The 2-methyl-2,3-dihydrobenzofuran-7-carboxylic acid, used as a starting material, was obtained as described in *Monatschefte fur Chemie,* 1990, 121, 883-891.The product gave the following data: NMR Spectrum: (DMSOd$_6$) 1.50 (m, 3H), 2.05 (s, 3H), 2.25 (s, 3H), 2.55 (m, 4H), 3.28 (m, 4H), 3.39 (m, 2H), 5.12 (m, 1H) 6.98 (s, 1H), 7.41 (d, 2H), 7.49 (s, 1H), 7.61 (m, 3H), 7.8 (m, 2H), 8.1 (s, 1H), 9.87 (s, 1H); Mass Spectrum: M+H$^+$510.

f) The 2,2-dimethylchroman-6-carboxylic acid, used as a starting material, was obtained as described in *Tetrahedron,* 1982, 38, 3673-3677. The product gave the following data: NMR Spectrum: (DMSOd$_6$) 1.30 (m, 6H), 1.79 (m, 2H), 2.05 (s, 3H), 2.25 (s, 3H), 2.5 (m, 4H) 2.8 (m, 2H), 3.3 (m, 4H), 6.8 (d, 1H), 7.38 (m, 1H), 7.46 (m, 1H), 7.62(m, 2H), 7.69-7.98 (m, 4H), 8.09 (s, 1H), 10.18 (s, 1H); Mass Spectrum: M+H$^+$538.

g) The product gave the following data: NMR Spectrum: (DMSOd$_6$) 1.84-1.94 (m, 2H), 2.07 (s, 3H), 2.25 (s, 3H), 2.42-2.5 (m, 2H), 2.62-2.66 (m, 2H), 3.53 (t, 2H), 3.58-3.64 (m, 2H), 7.26 (s, 1H), 7.38 (d, 1H), 7.4-7.5 (m, 2H), 7.51-7.61 (m, 3H), 7.78-7.86 (m, 4H), 8.01 (s, 1H), 7.92-7.99 (m, 2H), 8.22 (d, 1H), 8.38 (d, 1H), 10.59 (s, 1H); Mass Spectrum: M+H$^+$558.

h) The product gave the following data: NMR Spectrum: (DMSOd$_6$) 1.86-1.98 (m, 2H), 2.06 (s, 3H), 2.25 (s, 3H), 2.42-2.5 (m, 2H), 2.62-2.66 (m,2H), 3.53 (t, 2H), 3.58-3.64 (m, 2H), 4.12 (s, 2H), 7.24 (s, 1H), 7.32-7.43 (m, 4H), 7.52-7.61 (m, 3H), 7.72 (d, 1H), 7.8 (d, 1H), 7.85 (s, 1H), 7.92-7.99 (m, 2H), 8.18 (d, 1H), 10.49 (s, 1H); Mass Spectrum: M+H$^+$556.

i) The 5-(3-chlorophenyl)furan-2-carboxylic acid, used as a starting material, was obtained as described in *Chem. Pharm. Bull.,* 1981, 29, 2420-2430. The product gave the following data: NMR Spectrum: (DMSOd$_6$) 2.05 (s, 3H), 2.22 (s, 3H), 2.47-2.5 (m, 4H), 3.25-3.35 (m, 4H), 7.28 (d, 1H), 7.38-7.48 (m, 5H), 7.63 (s, 2H), 7.76 (s, 1H), 7.84 (m, 1H), 7.9 (d, 1H), 8.08 (s, 2H), 10.38 (s, 1H); Mass Spectrum: M+H$^+$554 & 556.

j) The 5-(4-chlorophenyl)furan-2-carboxylic acid, used as a starting material, was obtained using analogous procedures to those described in *Chem. Pharm. Bull.,* 1981, 29, 2420-2430. The product gave the following data: NMR Spectrum: (DMSOd$_6$) 2.05 (s, 3H), 2.22 (s, 3H), 2.47-2.5 (m, 4H), 3.2-3.3 (m, 4H), 7.2 (d, 1H), 7.39-7.48(m, 3H) 7.54 (d, 2H), 7.63 (s, 2H), 7.75 (s, 1H), 7.84 (m, 1H), 7.98 (m, 2H), 8.08 (s, 1H), 10.34 (s, 1H); Mass Spectrum: M+H$^+$554 & 556.

k) The product gave the following data: NMR Spectrum: (DMSOd$_6$) 2.04 (s, 3H), 2.46 (s, 3H), 2.47-2.5 (m, 4H), 3.2-3.3 (m, 4H), 7.41 (d, 1H), 7.48-7.51 (m, 3H), 7.6-7.65 (m, 3H), 7.73-7.8 (m, 4H), 8.01 (d, 1H), 8.07 (s, 1H), 10.5 (s, 1H); Mass Spectrum: M+H$^+$570 & 572.

l) The product gave the following data: NMR Spectrum: (DMSOd$_6$) 2.05 (s, 3H), 2.22(s, 3H), 2.47-2.5 (m, 4H), 3.2-3.3 (m, 4H), 7.38-7.53 (m, 4H), 7.61-7.65 (m, 2H), 7.72-7.8 (m, 4H), 8.08 (s, 1H),8.22 (s, 1H), 8.47 (s, 1H), 10.5 (s, 1H); Mass Spectrum: M+H$^+$570 & 572.

m) The product gave the following data: NMR Spectrum: (DMSOd$_6$) 2.05 (s, 3H), 2.23(s, 3H), 2.47-2.5 (m, 4H), 3.2-3.3 (m,4H), 3.7 (s, 3H), 7.01 (d, 2H), 7.43 (d, 1H), 7.48 (s, 1H), 7.6-7.66 (m, 4H), 7.74-7.8 (m, 2H), 8.02 (s, 1H), 8.08 (s, 1), 8.4 (s, 1H), 10.41 (s, 1H); Mass Spectrum: M+H$^+$566.

n) The 3-phenyl)isothiazole-5-carboxylic acid, used as a starting material, was obtained as described in *Helv. Chim. Acta,* 1966, 49, 2466-2469. The product gave the following data: NMR Spectrum: (DMSOd$_6$) 2.03 (s, 3H), 2.22 (s, 3H), 2.47-2.5 (m, 4H), 3.25-3.35 (m, 4H), 7.35 (d, 1H), 7.44-7.52 (m, 5H), 7.62 (s, 1H), 7.64-7.73 (m, 2H), 7.98 (d, 2H), 8.06 (s, 1H), 8.4 (s, 1H), 10.38 (s, 1H); Mass Spectrum: M+H$^+$537.

o) The product gave the following data: NRM Spectrum: (DMSOd$_6$) 2.05 (s, 3H), 2.2 (s, 4H), 7.3-7.35 (m, 1H), 7.4-7.6 (m, 5H), 7.75-7.9 (m, 5H), 8.2 (d, 1H), 8.3-8.4 (m, 2H), 10.6(s, 1H); Mass Spectrum: M+H$^+$544.

p) The product gave the following data: NMR Spectrum: (DMSOd$_6$) 2.05 (s, 3H), 2.3 (s, 3H), 2.5-2.65 (m,4H), 4.18 (s, 2H), 7.3-7.65 (m, 7H), 7.7-7.8 (m, 3H), 7.9 (s, 1H), 7.95 (d, 1H), 8.1 (d, 1H), 8.3 (s, 1H), 10.5 (s, 1H); Mass Spectrum: M+H$^+$542.

q) 3-(5-Amino-2-methylphenyl)-6-(4-tert-butoxycarbonylpiperazin-1-yl)-3,4-dihydroquinazolin-4-one was used as a starting material. The initial reaction product was 3-[5-fluoren-1-ylcarbonylamino-2-methylphenyl]-6-(4-tert-butoxycarbonylpiperazin-1-yl)-3,4-dihydroquinazolin-4-one which was treated with a saturated solution of hydrogen chloride in ethanol to cleave the tert-butoxycarbonyl protecting group. The resultant product gave the following data: NMR Spectrum: (DMSOd$_6$) 2.07 (s, 3H), 3.26 (m, 4H), 3.5 (m, 4H), 4.18 (s, 2H), 7.32-7.5 (m, 4H), 7.55-7.63 (m, 3H), 7.69-7.81 (m, 4H), 7.91-8.0 (m, 3H), 8.11 (s, 1H), 8.87 (s, 1H); Mass Spectrum: M+H$^+$528.

The 3-(5-amino-2-methylphenyl)-6-(4-tert-butoxycarbonylpiperazin-1-yl)-3,4-dihydroquinazolin-4-one used as a starting material was prepared as follows:-

A mixture of N-(2-methyl-5-nitrophenyl)-5-chloro-2-nitrobenzamide (5.02 g), piperazine (5.13 g) and DMSO (15 ml) was stirred and heated to 100° C. for 2 hours. The mixture was cooled to ambient temperature and poured into water. The resultant solid was isolated, washed in turn with water and diethyl ether and dried under vacuum at 55° C. There was thus obtained N-(2-methyl-5-nitrophenyl)-2-nitro-5-piperazin-1-ylbenzamide (4.88 g); NMR Spectrum: (DMSOd$_6$) 2.38 (s, 3H), 2.8 (m, 4H), 3.43 (m, 4H), 7.04 (m, 1H), 7.14 (d, 1H), 7.52 (d, 1H), 8.01 (m, 1H), 8.06 (d, 1H), 8.53 (d, 1H), 10.14 (s, 1H); Mass Spectrum: M+H$^+$386.

2-(tert-Butoxycarbonyloxyimino)phenylacetonitrile (2.55 g) was added to a mixture of N-(2-methyl-5-nitrophenyl)-2-nitro-5-piperazin-1-ylbenzamide (2.5 g), triethylamine (1.7 ml), water (30 ml) and 1,4-dioxane (30 ml) and the reaction mixture was stirred at ambient temperature for 16 hours. The mixture was diluted with water and the resultant solid was isolated and washed in turn with water and diethyl ether. There was thus obtained N-(2-methyl-5-nitrophenyl)-5-(4-tert-butoxycarbonylpiperazin-1-yl)-2-nitrobenzamide (2.85 g); NMR Spectrum: (CDCl$_3$) 1.48 (s, 9H), 2.37 (s, 3H), 3.48 (m, 4H), 3.61 (m, 4H), 6.77 (m, 1H), 6.87 (m, 1H), 7.33 (d, 1H), 7.56 (s, 1H), 7.95 (m, 1H), 8.04 (d, 1H), 8.68 (s, 1H); Mass Spectrum: M+H$^+$484.

The material so obtained was hydrogenated in the presence of 10% palladium-on-carbon catalyst using an analogous procedure to that described in the third paragraph of the portion of Example 5 which is concerned with the preparation of starting materials. There was thus obtained N-(5-amino-2-methylphenyl)-2-amino-5-4-tert-butoxycarbonylpiperazin-1-yl)benzamide in 96% yield; NMR Spectrum: (CDCl$_3$) 1.5 (s, 9H), 2.21 (s, 3H), 3.0 (m, 4H), 3.6 (m, 4H), 3.65 (s, 2H), 4.98 (s, 2H), 6.47 (m, 1H), 6.73 (d, 1H), 7.01 (m, 2H), 7.11 (d, 1H), 7.41 (d, 1H), 7.8 (s, 1H); Mass Spectrum: M+H$^+$426.

A mixture of the material so obtained (2.12 g), triethyl orthoformate (1.7 ml), glacial acetic acid (0.07 ml) and ethanol (50 ml) was stirred and heated to 70° C. for 16 hours. A sodium hydroxide solution (1M, 5.0 ml) was added and the mixture was stirred and heated to 60° C. for 16 hours. A further portion of sodium hydroxide solution (1M, 2.5 ml) was added and the mixture was again heated to 60° C. for 16 hours. The resultant mixture was cooled to ambient temperature and evaporated. The residue was dissolved in water and extracted with methylene chloride. The organic phase was dried and evaporated. The material so obtained was purified by column chromatography on silica using a 20:1 mixture of methylene chloride and methanol. There was thus obtained 3-(5-amino-2-methylphenyl)-6-(4-tert-butoxycarbonylpiperazin-1-yl)-3,4-dihydroquinazolin-4-one (1.51 g); NMR Spectrum: (CDCl$_3$) 1.5 (s, 9H), 2.06 (s, 3H), 3.27 (m, 4H), 3.62 (m, 4H), 3.72 (s, 2H), 6.58 (d, 1H), 6.74 (m, 1H), 7.15 (d, 1H), 7.44 (m, 1H), 7.68 (m, 2H), 7.86 (s, 1H); Mass Spectrum: M+H$^+$436.

r) 3-(5-Amino-2-methylphenyl)-6-(4-tert-butoxycarbonylpiperazin-1-yl)-3,4-dihydroquinazolin-4-one was used as a starting material. The initial reaction product was 3-[5-dibenzofuran-4-ylcarbonylamino-2-methylphenyl]-6-(4-tert-butoxycarbonylpiperazin-1-yl)-3,4-dihydroquinazolin-4-one which was treated with a saturated solution of hydrogen chloride in ethanol to cleave the tert-butoxycarbonyl protecting group. The resultant product gave the following data: NMR Spectrum: (DMSOd$_6$) 2.07 (s, 3H), 3.29 (m, 4H), 3.5 (m, 4H), 7.42-7.6 (m, 6H), 7.67 (m, 1H), 7.8-7.9 (m, 4H), 7.95 (s, 1H), 8.20-8.27 (m, 2H), 8.36 (d, 1H), 8.85 (s, 1H); Mass Spectrum: M+H$^+$530.

EXAMPLE 18

3-[2-Fluoro-5-(3-fluoro-5-morpholinobenzamido) phenyl]-6-(4-methylpiperazin-1-yl)-3,4-dihydroquinazolin-4-one Triethyl orthoformate (0.123 ml) was added to a stirred mixture of N-[2-fluoro-5-(3-fluoro-5-morpholinobenzamido)phenyl]-2-amino-5-(4-methylpiperazin-1-yl)benzamide (0.31 g), glacial acetic acid (0.016 ml) and ethanol (4 ml) and the resultant mixture was heated to 76° C. for 18 hours. The mixture was evaporated and the residue was partitioned between methylene chloride and a saturated aqueous solution of sodium bicarbonate. The organic solution was washed with water and with a saturated aqueous sodium chloride solution, dried (MgSO$_4$) and evaporated. The residue was purified by column chromatography on silica using increasingly polar mixtures of methylene chloride and methanol as eluent. There was thus obtained the title compound (0.119 g); NMR Spectrum: (DMSOd$_6$) 2.23 (s, 3H), 3.22 (m, 4H), 3.72 (m, 4H), 6.99 (d, 1H), 7.12 (d, 1H), 7.29 (s, 1H), 7.47 (m, 2H), 7.63 (s, 1H), 7.89 (m, 1H), 7.97 (m, 1H), 8.18 (s, 1H), 10.44 (s, 1H); Mass Spectrum: M+H$^+$561.

The N-[2-fluoro-5-(3-fluoro-5-morpholinobenzamido) phenyl]-2-amino-5-(4-methylpiperazin-1-yl)benzamide used as a starting material was prepared as follows:-

Oxalyl chloride (0.55 g) was added dropwise to a stirred mixture of 3-fluoro-5-morpholinobenzoic acid (6.36 g), DMF (a few drops) and methylene chloride (200 ml) which had been cooled to 0° C. The mixture was allowed to warm to ambient temperature and was stirred for 4 hours. The mixture was evaporated. The residue was dissolved in methylene chloride (100 ml) and was added dropwise to a stirred mixture of 4-fluoro-3-nitroaniline (4.05 g), triethylamine (12.0 ml) and methylene chloride (100 ml). The resultant mixture was stirred at ambient temperature for 20 hours. The mixture was evaporated and the residue was partitioned between methylene chloride and water. The organic phase was washed with a saturated aqueous sodium chloride solution, dried (MgSO$_4$) and evaporated. There was thus obtained N-(4-fluoro-3-nitrophenyl)-3-fluoro-5-morpholinobenzamide (7.06 g); NMR Spectrum: (DMSOd$_6$) 3.24 (m, 4H), 3.73 (m, 4H), 7.0 (m, 1H), 7.13 (d, 1H), 7.3 (s, 1H), 7.58 (t, 1H), 8.11 (m, 1H), 8.63 (m, 1H), 10.56 (s, 1H); Mass Spectrum: (M−H)$^-$362.

A mixture of a portion (4.34 g) of the material so obtained, 30% palladium-on-carbon (0.68 g) and methanol (500 ml) was stirred under an atmosphere of hydrogen gas. After cessation of hydrogen uptake, the catalyst was removed by filtration and the filtrate was evaporated. There was thus obtained N-(3-amino-4-fluorophenyl)-3-fluoro-5-morpholinobenzamide (3.49 g); NMR Spectrum: (DMSOd$_6$) 3.22 (m, 4H), 3.75 (m, 4H), 5.12 (s, 2H), 6.81 (m, 1H), 6.89-6.96 (m, 2H), 7.08 (d, 1H), 7.24 (m, 2H), 9.92 (s, 1H); Mass Spectrum: M+H$^+$334.

Diisopropylamine (3.13 ml) was added to a mixture of N-(3-amino-4-fluorophenyl)-3-fluoro-5-morpholinobenzamide (1.99 g), 5-chloro-2-nitrobenzoic acid (1.45 g), 2-(7-azabenzotriazol-1-yl)-1,1,3,3-tetramethyluronium hexafluorophosphate(V) (2.74 g) in DMF (12 ml) and the reaction mixture was stirred at ambient temperature for 18 hours. The mixture was poured into water and the resultant precipitate was isolated, washed with water and dried under vacuum at 55° C. There was thus obtained N-[2-fluoro-5-(3-fluoro-5-morpholinobenzamido)phenyl]-5-chloro-2-nitrobenzamide (1.64 g); NMR Spectrum: (DMSOd$_6$) 3.22 (m, 4H), 3.74 (m, 4H), 6.97 (d, 1H), 7.15 (d, 1H), 7.25-7.32 (m, 2H), 7.66 (m, 1H), 7.82 (m, 2H), 7.88 (s, 1H), 8.18 (d, 1H), 8.34 (m, 1H), 10.32 (s, 1H), 10.58 (s, 1H); Mass Spectrum: M+H$^+$517 and 519.

A mixture of a portion (0.55 g) of the material so obtained and N-methylpiperazine (2 ml) was stirred and heated to 80° C. for 18 hours. The reaction mixture was cooled to ambient temperature and poured into water. The resultant precipitate was isolated, washed with water and dried under vacuum at 55° C. There was thus obtained N-[2-fluoro-5-(3-fluoro-5-morpholinobenzamido)phenyl]-5-(4-methylpiperazin-1-yl-2-nitrobenzamide (0.55 g); NMR Spectrum: (DMSOd$_6$) 2.2 (s, 3H), 2.41 (m, 3H), 3.22 (m, 4H), 3.48 (m, 4H), 3.72 (m, 4H), 6.93 (m, 2H), 7.07 (m, 1H), 7.16 (d, 1H), 7.25 (t, 1H), 7.32 (s, 1H), 7.63 (m, 1H), 8.14 (d, 1H); 8.36 (m, 1H), 10.26 (s, 1H), 10.3 (s, 1H); Mass Spectrum: M+H$^+$581.

A mixture of the material so obtained, 30% palladium-on-carbon (0.075 g) and ethanol (500 ml) was stirred under an atmosphere of hydrogen gas. After cessation of hydrogen uptake, the catalyst was removed by filtration and the filtrate was evaporated. There was thus obtained N-[2-fluoro-5-(3-fluoro-5-morpholinobenzamido)phenyl]-2-amino-5-(4-methylpiperazin-1-yl)benzamide (0.52 g); NMR Spectrum: (DMSOd$_6$) 2.22 (s, 3H), 2.44 (m, 4H), 2.98 (m, 4H), 3.21 (m, 4H), 3.72 (m, 4H), 5.93 (br s, 1H), 6.69 (d, 1H) 6.94-7.01 (m, 2H), 7.12 (d, 1H), 7.2-7.3 (m, 3H), 7.59 (m, 1H), 7.97 (m, 1H), 10.24 (s, 1H); Mass Spectrum: M+H$^+$551.

EXAMPLE 19

3-[2-Fluoro-5-(3-fluoro-5-morpholinobenzamido)phenyl]-6-(4-methylhomopiperazin-1-yl)-3,4-dihydroquinazolin-4-one Using an analogous procedure to that described in Example 18, N-[2-fluoro-5-(3-fluoro-5-morpholinobenzamido)phenyl]-2-amino-5-(4-methylhomopiperazin-1-yl)benzamide was reacted with triethyl orthoformate to give the title compound in 63% yield; NMR Spectrum: (DMSOd$_6$) 1.92 (m, 2H), 2.25 (s, 3H), 2.46 (m, 2H), 2.64 (m, 2H), 3.21 (t, 4H), 3.53 (t, 2H), 3.6 (m, 2H), 3.72 (t, 4H), 6.99 (d, 1H), 7.12 (d, 1H), 7.23 (m, 1H), 7.3 (s, 1H), 7.36 (m, 1H), 7.48 (t, 1H), 7.58 (d, 1H), 7.87 (m, 1H), 7.96 (m, 1H), 8.06 (s, 1H), 10.43 (s, 1H); Mass Spectrum: M+H$^+$575.

The N-[2-fluoro-5-(3-fluoro-5-morpholinobenzamido)phenyl]-2-amino-5-(4-methylhomopiperazin-1-yl)benzamide used as a starting material was prepared as follows:-

A mixture of N-[2-fluoro-5-(3-fluoro-5-morpholinobenzamido)phenyl]-5-chloro-2-nitrobenzamide (0.55 g) and N-methylhomopiperazine (2 ml) was stirred and heated to 80° C. for 18 hours. The reaction mixture was cooled to ambient temperature and poured into water. The resultant precipitate was isolated, washed with water and dried under vacuum at 55° C. There was thus obtained N-[2-fluoro-5-(3-fluoro-5-morpholinobenzamido)phenyl]-5-(4-methylhomopiperazin-1-yl-2-nitrobenzamide (0.58 g); NMR Spectrum: (DMSOd$_6$) 1.89 (m, 2H), 2.25 (s, 3H), 2.44 (m, 2H), 2.63 (m, 2H), 3.22 (t, 4H), 3.59 (t, 2H), 3.66 (m, 2H), 3.74 (t, 4H), 6.72 (d, 1H), 6.87, (m, 1H), 6.97 (d, 1H), 7.16 (d, 1H), 7.23 (t, 1H), 7.31 (s, 1H), 7.63 (m, 1H), 8.02 (d, 1H), 8.34 (m, 1H), 10.3 (s, 1H); Mass Spectrum: M+H$^+$595.

A mixture of the material so obtained, 30% palladium-on-carbon (0.08 g) and ethanol (500 ml) was stirred under an atmosphere of hydrogen gas. After cessation of hydrogen uptake, the catalyst was removed by filtration and the filtrate was evaporated. There was thus obtained N-[2-fluoro-5-(3-fluoro-5-morpholinobenzamido)phenyl]-2-amino-5-(4-methylhomopiperazin-1-yl)benzamide (0.48 g); NMR Spectrum: (DMSOd$_6$) 1.86 (m, 2H), 2.24 (s, 3H), 2.44 (m, 2H), 2.59 (m, 2H), 3.22 (t, 4H), 3.38 (t, 2H), 3.43 (m, 2H), 2.72 (t, 4H), 6.68 (d, 1H), 6.76 (m, 1H), 6.98 (m, 2H), 7.12 (m, 1H), 7.22-7.31 (m, 2H), 7.58 (m, 1H), 8.08 (m, 1H), 10.25 (br s, 1H); Mass Spectrum: M+H$^+$565.

EXAMPLE 20

Pharmaceutical Compositions

The following illustrate representative pharmaceutical dosage forms of the invention as defined herein (the active ingredient being termed "Compound X"), for therapeutic or prophylactic use in humans:

| (a) | Tablet I | mg/tablet |
|---|---|---|
| | Compound X | 100 |
| | Lactose Ph.Eur | 182.75 |
| | Croscarmellose sodium | 12.0 |
| | Maize starch paste (5% w/v paste) | 2.25 |
| | Magnesium stearate | 3.0 |
| (b) | Tablet II | mg/tablet |
| | Compound X | 50 |
| | Lactose Ph.Eur | 223.75 |
| | Croscarmellose sodium | 6.0 |
| | Maize starch | 15.0 |
| | Polyvinylpyrrolidone (5% w/v paste) | 2.25 |
| | Magnesium stearate | 3.0 |
| (c) | Tablet III | mg/tablet |
| | Compound X | 1.0 |
| | Lactose Ph.Eur | 93.25 |
| | Croscarmellose sodium | 4.0 |
| | Maize starch paste (5% w/v paste) | 0.75 |
| | Magnesium stearate | 1.0 |
| (d) | Capsule | mg/capsule |
| | Compound X | 10 |
| | Lactose Ph.Eur | 488.5 |
| | Magnesium | 1.5 |
| (e) | Injection I | (50 mg/ml) |
| | Compound X | 5.0% w/v |
| | 1 M Sodium hydroxide solution | 15.0% v/v |
| | 0.1 M Hydrochloric acid (to adjust pH to 7.6) | |
| | Polyethylene glycol 400 | 4.5% w/v |
| | Water for injection to 100% | |
| (f) | Injection II | (10 mg/ml) |
| | Compound X | 1.0% w/v |
| | Sodium phosphate BP | 3.6% w/v |
| | 0.1 M Sodium hydroxide solution | 15.0% v/v |
| | Water for injection to 100% | |
| (g) | Injection III | (1 mg/ml, buffered to pH6) |
| | Compound X | 0.1% w/v |
| | Sodium phosphate BP | 2.26% w/v |
| | Citric acid | 0.38% w/v |
| | Polyethylene glycol 400 | 3.5% w/v |
| | Water for injection to 100% | |
| (h) | Aerosol I | mg/ml |
| | Compound X | 10.0 |
| | Sorbitan trioleate | 13.5 |
| | Trichlorofluoromethane | 910.0 |
| | Dichlorodifluoromethane | 490.0 |
| (i) | Aerosol II | mg/ml |
| | Compound X | 0.2 |
| | Sorbitan trioleate | 0.27 |
| | Trichlorofluoromethane | 70.0 |
| | Dichlorodifluoromethane | 280.0 |
| | Dichlorotetrafluoroethane | 1094.0 |
| (j) | Aerosol III | mg/ml |
| | Compound X | 2.5 |
| | Sorbitan trioleate | 3.38 |
| | Trichlorofluoromethane | 67.5 |
| | Dichlorodifluoromethane | 1086.0 |
| | Dichlorotetrafluoroethane | 191.6 |

-continued

| (k) | Aerosol IV | mg/ml |
|---|---|---|
| | Compound X | 2.5 |
| | Soya lecithin | 2.7 |
| | Trichlorofluoromethane | 67.5 |
| | Dichlorodifluoromethane | 1086.0 |
| | Dichlorotetrafluoroethane | 191.6 |
| (l) | Ointment | ml |
| | Compound X | 40 mg |
| | Ethanol | 300 μl |
| | Water | 300 μl |
| | 1-Dodecylazacycloheptan-2-one | 50 μl |
| | Propylene glycol | to 1 ml |

Note

The above formulations may be obtained by conventional procedures well known in the pharmaceutical art. The tablets (a)-(c) may be enteric coated by conventional means, for example to provide a coating of cellulose acetate phthalate. The aerosol formulations (h)-(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid.

The invention claimed is:

1. An amide derivative of the Formula Ia

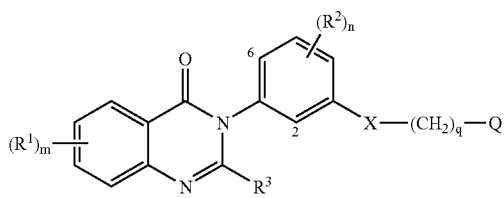

wherein X is —NHCO— or CONH—;

m is 1, 2 or 3;

at least one $R^1$ is a piperazinyl group and any other $R^1$ that is not a piperazinyl group is selected from hydroxy, halogeno, trifluoromethyl, cyano, mercapto, nitro, amino, carboxy, carbamoyl, formyl, (1-6C)alkyl, (2-6C)alkenyl, (2-6C)alkynyl, (1-6C)alkoxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (1-6C)alkanoylamino, N-(1-6C)alkyl-(1-6C)alkanoylamino, N-(1-6C)alkylsulphamoyl, N,N-di-[(1-6C)alkyl]sulphamoyl, (1-6C)alkanesulphonylamino, N-(1-6C)alkyl-(1-6C)alkanesulphonylamino, halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, carboxy-(1-6C)alkyl, (1-6C)alkoxycarbonyl-(1-6C)alkyl, carbamoyl-(1-6C)alkyl, N-(1-6C)alkylcarbamoyl-(1-6C)alkyl, N,N-di-[(1-6C)alkyl]carbamoyl-(1-6C)alkyl, halogeno-(2-6C)alkoxy, hydroxy-(2-6C)alkoxy, (1-6C)alkoxy-(2-6C)alkoxy, cyano-(1-6C)alkoxy, carboxy-(1-6C)alkoxy, (1-6C)alkoxycarbonyl-(1-6C)alkoxy, carbamoyl-(1-6C)alkoxy, N-(1-6C)alkylcarbamoyl-(1-6C)alkoxy, N,N-di-[(1-6C)alkyl]carbamoyl-(1-6C)alkoxy, amino-(2-6C)alkoxy, (1-6C)alkylamino-(2-6C)alkoxy, di-[(1-6C)alkyl]amino-(2-6C)alkoxy, halogeno-(2-6C)alkylamino, hydroxy-(2-6C)alkylamino, (1-6C)alkoxy-(2-6C)alkylamino, cyano-(1-6C)alkylamino, carboxy-(1-6C)alkylamino, (1-6C)alkoxycarbonyl-(1-6C)alkylamino, carbamoyl-(1-6C)alkylamino, N-(1-6C)alkylcarbamoyl-(1-6C)alkylamino N,N-di-[(1-6C)alkyl]carbamoyl-(1-6C)alkylamino, amino-(2-6C)alkylamino, (1-6C)alkylamino-(2-6C)alkylamino, di-[(1-6C)alkyl]amino-(2-6C)alkylamino, N-(1-6C)alkyl-halogeno-(1-6C)alkylamino, N-(1-6C)alkyl-hydroxy-(2-6C)alkylamino, N-(1-6C)alkyl-(1-6C)alkoxy-(2-6C)alkylamino, N-(1-6C)alkyl-cyano-(1-6C)alkylamino, N-(1-6C)alkyl-carboxy-(1-6C)alkylamino, N-(1-6C)alkyl-(1-6C)alkoxycarbonyl-(1-6C)alkylamino N-(1-6C)alkyl-carbamoyl-(1-6C)alkylamino, N-(1-6C)alkyl-N-(1-6C)alkylcarbamoyl-(1-6C)alkylamino, N-(1-6C)alkyl-N,N-di-[(1-6C)alkyl]carbamoyl-(1-6C)alkylamino, N-(1-6C)alkyl-amino-(2-6C)alkylamino, N-(1-6C)alkyl-(1-6C)alkylamino-(2-6C)alkylamino, N-(1-6C)alkyl-di-[(1-6C)alkyl]amino-(2-6C)alkylamino, halogeno-(2-6C)alkanoylamino, hydroxy-(2-6C)alkanoylamino, (1-6C)alkoxy-(2-6C)alkanoylamino, cyano-(2-6C)alkanoylamino, carboxy-(2-6C)alkanoylamino, (1-6C)alkoxycarbonyl-(2-6C)alkanoylamino, carbamoyl-(2-6C)alkanoylamino, N-(1-6C)alkylcarbamoyl-(2-6C)alkanoylamino N,N-di-[(1-6C)alkyl]carbamoyl-(2-6C)alkanoylamino, amino-(2-6C)alkanoylamino, (1-6C)alkylamino-(2-6C)alkanoylamino or di-[(1-6C)alkyl]amino-(2-6C)alkanoylamino and (1-3C)alkylenedioxy, and wherein any of the $R^1$ substituents defined hereinbefore which comprises a $CH_2$ group which is attached to 2 carbon atoms or a $CH_3$ group which is attached to a carbon atom may optionally bear on each said $CH_2$ or $CH_3$ group a substituent selected from hydroxy, amino, (1-6C)alkoxy, (1-6C)alkylamino and di-[(1-6C)alkyl]amino, and wherein any piperazinyl group in a $R^1$ substituent may optionally bear 1 or 2 substituents selected from hydroxy, halogeno, (1-6C)alkyl, (1-6C)alkoxy, carboxy, (1-6C)alkoxycarbonyl, N-(1-6C)alkylcarbamoyl, N,N-di-[(1-6C)alkyl]carbamoyl, (2-6C)alkanoyl, amino, (1-6C)alkylamino, di-[(1-6C)alkyl]amino, halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, aryl and aryl-(1-6C)alkyl, and wherein any piperazinyl group in a $R^1$ substituent may optionally bear 1 or 2 oxo or thioxo substituents;

n is 0, 1 or 2;

$R^2$ is hydroxy, halogeno, trifluoromethyl, cyano, mercapto, nitro, amino, carboxy, (1-6C)alkoxycarbonyl, (1-6C)alkyl, (2-6C)alkenyl, (2-6C)alkynyl, (1-6C)alkoxy, (1-6C)alkylamino or di-[(1-6C)alkyl]amino;

$R^3$ is hydrogen, halogeno, (1-6C)alkyl or (1-6C)alkoxy;

q is 0, 1, 2, 3 or 4; and

Q is heteroaryl, optionally substituted with 1, 2 or 3 substituents selected from hydroxy, halogeno, trifluoromethyl, cyano, mercapto, nitro, amino, carboxy, carbamoyl, formyl, (1-6C)alkyl, (2-6C)alkenyl, (2-6C)alkynyl, (1-6C)alkoxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (1-6C)alkanoylamino, N-(1-6C)alkyl-(1-6C)alkanoylamino, N-(1-6C)alkylsulphamoyl, N,N-di-[(1-6C)alkyl]sulphamoyl, (1-6C)alkanesulphonylamino, N-(1-6C)alkyl-(1-6C)alkanesulphonylamino, halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di[(1-6C)alkyl]amino-(1-6C)alkyl, carboxy-(1-6C)alkyl, (1-6C)alkoxycarbonyl-(1-6C)alkyl, carbamoyl-(1-6C)alkyl, N-(1-6C)alkylcarbamoyl-(1-6C)alkyl, N,N-di-[(1-6C)alkyl]carbamoyl-(1-6C)alkyl, halogeno-(2-6C)alkoxy, hydroxy-(2-6C)alkoxy, (1-6C)alkoxy-(2-6C)alkoxy, cyano-(1-6C)alkoxy, carboxy-(1-6C)alkoxy, (1-6C)alkoxycarbonyl-(1-6C)alkoxy, carbamoyl(1-6C)alkoxy, N-(1-6C)alkylcarbamoyl-(1-6C)alkoxy, N,N-di-[(1-6C)alkyl]carbamoyl-(1-6C)alkoxy, amino-(2-6C)alkoxy, (1-6C)alkylamino-(2-6C)alkoxy, di-[(1-6C)alkyl]amino-(2-6C)alkoxy, halogeno-(2-6C)alkylamino, hydroxy-(2-6C)alkylamino, (1-6C)alkoxy-(2-6C)alkylamino, cyano-(1-6C)alkylamino, carboxy-(1-6C)alkylamino, (1-6C)alkoxycarbonyl-(1-6C)alkylamino, carbamoyl-(1-6C)alkylamino, N-(1-6C)alkylcarbamoyl-(1-6C)alkylamino, N,N-di-[(1-6C)alkyl]carbamoyl-(1-6C)alkylamino, amino-(2-6C)alkylamino, (1-6C)alkylamino-(2-6C)alkylamino, di-[(1-6C)alkyl]amino-(2-6C)alkylamino, N-(1-6C)alkyl-halogeno-(1-6C)alkylamino, N-(1-6C)alkyl-hydroxy-(2-6C)alkylamino, N-(1-6C)alkyl-(1-6C)alkoxy-(2-6C)alkylamino, N-(1-6C)alkyl-cyano-(1-6C)alkylamino, N-(1-6C)alkyl-carboxy-(1-6C)alkylamino, N-(1-6C)alkyl-(1-6C)alkoxycarbonyl-(1-6C)alkylamino, N-(1-6C)alkyl-carbamoyl-(1-6C)alkylamino, N-(1-6C)alkyl-N-(1-6C)alkylcarbamoyl-(1-6C)alkylamino, N-(1-6C)alkyl-N,N-di-[(1-6C)alkyl]carbamoyl-(1-6C)alkylamino, N-(1-6C)alkyl-amino-(2-6C)alkylamino, N-(1-6C)alkyl-(1-6C)alkylamino-(2-6C)alkylamino, N-(1-6C)alkyl-di-[(1-6C)alkyl]amino-(2-6C)alkylamino, halogeno-(2-6C)alkanoylamino, hydroxy-(2-6C)alkanoylamino, (1-6C)alkoxy-(2-6C)alkanoylamino, cyano-(2--6C)alkanoylamino, carboxy-(2-6C)alkanoylamino, (1-6C)alkoxycarbonyl-(2-6C)alkanoylamino, carbamoyl-(2-6C)alkanoylamino N-(1-6C)alkylcarbamoyl-(2-6C)alkanoylamino, N,N-di-[(1-6C)alkyl]carbamoyl-(2-6C)alkanoylamino, amino-(2-6C)alkanoylamino, (1-6C)alkylamino--(2-6C)alkanoylamino, di-[(1-6C)alkyl]amino-(2-6C)alkanoylamino, aryl, aryl-(1-6C)alkyl, aryl-(1-6C)alkoxy, aryloxy, arylamino, N-(1-6C)alkyl-arylamino, aryl-(1-6C)alkylamino, N-(1-6C)alkyl-aryl-(1-6C)alkylamino, aroylamino, arylsulphonylamino, N-arylsulphamoyl, aryl-(2-6C)alkanoylamino and (1-3C)alkylenedioxy, and wherein any of the substituents on Q defined hereinbefore which comprises a $CH_2$ group which is attached to 2 carbon atoms or a $CH_3$ group which is attached to a carbon atom may optionally bear on each said $CH_2$ or $CH_3$ group a substituent selected from hydroxy, amino, (l-6C)alkoxy, (1-6C)alkylamino and di-[(l -6C)alky]amino, and wherein any aryl group in a substituent on Q may optionally bear 1 or 2 substituents selected from hydroxy, halogeno, (1-6C)alkyl, (1-6C)alkoxy, carboxy, (1-6C)alkoxycarbonyl, N-(1-6C)alkylcarbamoyl, N,N-di-[(1-6C)alkyl]carbamoyl, (2-6C)alkanoyl, amino, (1-6C)alkylamino, di-[(1-6C)alkyl]amino, halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, aryl and aryl-(1-6C)alkyl;

or a pharmaceutically-acceptable salt or in-vivo-cleavable ester formed on an available carboxy group thereof.

2. An amide derivative of the Formula Ib

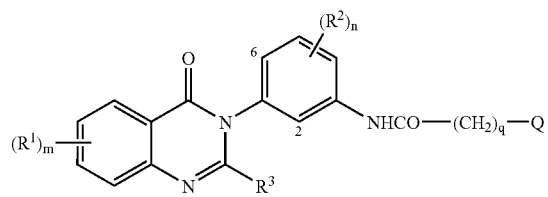

wherein m is 1, 2 or 3;

at least one $R^1$ is a piperazinyl group and any other $R^1$ group that is not a piperazinyl group is selected from hydroxy, halogeno, trifluoromethyl, cyano, mercapto, nitro, amino, carboxy, carbamoyl, formyl, (1-6C)alkyl, (2-6C)alkenyl, (2-6C)alkynyl, (1-6C)alkoxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (1-6C)alkanoylamino, N-(1-6C)alkylsulphamoyl N,N-di-[(1-6C)alkyl]sulphamoyl, (1-6C)alkanesulphonylamino, N-(1-6C)alkyl-(1-6C)alkanesulphonylamino, halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, carboxy-(1-6C)alkyl, (1-6C)alkoxycarbonyl-(1-6C)alkyl, carbamoyl-(1-6C)alkyl, N-(1-6C)alkylcarbamoyl-(1-6C)alkyl, N,N-di-[(1-6C)alkyl]carbamoyl-(1-6C)alkyl, halogeno-(2-6C)alkoxy, hydroxy-(2-6C)alkoxy, (1-6C)alkoxy-(2-6C)alkoxy, cyano-(1-6C)alkoxy, carboxy-(1-6C)alkoxy, (1-6C)alkoxycarbonyl-(1-6C)alkoxy, carbamoyl-(1-6C)alkoxy, N-(1-6C)alkylcarbamoyl-(1-6C)alkoxy, N,N-di-[(1-6C)alkyl]carbamoyl-(1-6C)alkoxy, amino-(2-6C)alkoxy, (1-6C)alkylamino-(2-6C)alkoxy, di[(1-6C)alkyl]amino-(2-6C)alkoxy, halogeno-(2-6C)alkylamino, hydroxy-(2-6C)alkylamino, (1-6C)alkoxy-(2-6C)alkylamino, cyano-(1-6C)alkylamino, carboxy-(1-6C)alkylamino, (1-6C)alkoxycarbonyl-(1-6C)alkylamino, carbamoyl-(1-6C)alkylamino, N-(1-6C)alkylcarbamoyl-(1-6C)alkylamino, N,N-di-[(1-6C)alkyl]carbamoyl-(1-6C)alkylamino, amino-(2-6C)alkylamino, (1-6C)alkylamino-(2-6C)alkylamino, di-[(1-6C)alkyl]amino-(2-6C)alkylamino, N-(1-6C)alkyl-halogeno-(1-6C)alkylamino, N-(1-6C)alkyl-hydroxy-(2-6C)alkylamino, N-(1-6C)alkyl-(1-6C)alkoxy-(2-6C)alkylamino, N-(1-6C)alkyl-cyano-(1-6C)alkylamino, N-(1-6C)alkyl-carboxy-(1-6C)alkylamino, N-(1-6C)alkyl-(1-6C)alkoxycarbonyl-(1-6C)alkylamino, N-(1-6C)alkyl-carbamoyl-(1-6C)alkylamino, N-(1-6C)alkyl-N-(1-6C)alkylcarbamoyl-(1-6C)alkylamino, N-(1-6C)alkyl-N,N-di-[(1-6C)alkyl]carbamoyl-(1-6C)alkylamino, N-(1-6C)alkyl-amino-(2-6C)alkylamino, N-(1-6C)alkyl-(1-6C)alkylamino-(2-6C)alkylamino, N-(1-6C)alkyl-di-[(1-6C)alkyl]amino-(2-6C)alkylamino, halogeno-(2-6C)alkanoylamino, hydroxy-(2-

6C)alkanoylamino, (1-6C)alkoxy-(2-6C)alkanoylamino, cyano-(2-6C)alkanoylamino, carboxy-(2-6C)alkanoylamino, (1-6C)alkoxycarbonyl-(2-6C)alkanoylamino, carbamoyl-(2-6C)alkanoylamino, N-(1-6C)alkylcarbamoyl-(2-6C)alkanoylamino N N-di-[(1-6C)alkyl]carbamoyl-(2-6C)alkanoylamino, amino-(2-6C)alkanoylamino, (1-6C)alkylamino-(2-6C)alkanoylamino, di-[(1-6C)alkyl]amino-(2-6C)alkanoylamino and (1-3C)alkylenedioxy, and wherein any of the $R^1$ substituents defined hereinbefore which comprises a $CH_2$ group which is attached to 2 carbon atoms or a $CH_3$ group which is attached to a carbon atom may optionally bear on each said $CH_2$ or $CH_3$ group a substituent selected from hydroxy, amino, (1-6C)alkoxy, (1-6C)alkylamino and di-[(1-6C)alkyl]amino, and wherein any piperazinyl group in a $R^1$ substituent may optionally bear 1 or 2 substituents selected from hydroxy, halogeno, (1-6C)alkyl, (1-6C)alkoxy, carboxy, (1-6C)alkoxycarbonyl, N-(1-6C)alkylcarbamoyl, N,N-di-[(1-6C)aikyl]carbamoyl, (2-6C)alkanoyl, amino, (1-6C)alkylamino, di-[(1-6C)alkyl]amino, halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, aryl and aryl-(1-6C)alkyl, n is 0, 1 or 2;

$R^2$ is hydroxy, halogeno, trifluoromethyl, cyano, mercapto, nitro, amino, carboxy, (1-6C)alkoxycarbonyl, (1-6C)alkyl, (2-6C)alkenyl, (2-6C)alkynyl, (1-6C)alkoxy, (1-6C)alkylamino or di-[(1-6C)alkyl]amino;

$R^3$ is hydrogen, halogeno, (1-6C)alkyl or (1-6C)alkoxy;

q is 0, 1, 2, 3 or 4; and

Q is heteroaryl, optionally substituted with 1, 2 or 3 substituents selected from hydroxy, halogeno, trifluoromethyl, cyano, mercapto, nitro, amino, carboxy, carbamoyl, formyl, (1-6C)alkyl, (2-6C)alkenyl, (2-6C)alkynyl, (1-6C)alkoxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (1-6C)alkanoylamino N-(1-6C)alkylsulphamoyl, N,N-di-[(1-6C)alkyl]sulphamoyl, (1-6C)alkanesulphonylamino N-(1-6C)alkyl-(1-6C)alkanesulphonylamino, halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, carboxy-(1-6C)alkyl, (1-6C)alkoxycarbonyl-(1-6C)alkyl, carbamoyl-(1-6C)alkyl, N-(1-6C)alkylcarbamoyl-(1-6C)alkyl, N,N-di-[(1-6C)alkyl]carbamoyl-(1-6C)alkyl, halogeno-(2-6C)alkoxy, hydroxy-(2-6C)alkoxy, (1-6C)alkoxy-(2-6C)alkoxy, cyano-(1-6C)alkoxy, carboxy-(1-6C)alkoxy, (1-6C)alkoxycarbonyl-(1-6C)alkoxy, carbamoyl-(1-6C)alkoxy, N-(1-6C)alkylcarbamoyl-(1-6C)alkoxy, N,N-di-[(1-6C)alkyl]carbamoyl-(1-6C)alkoxy, amino-(2-6C)alkoxy, (1-6C)alkylamino-(2-6C)alkoxy, di-[(1-6C)alkyl]amino-(2-6C)alkoxy, halogeno-(2-6C)alkylamino, hydroxy-(2-6C)alkylamino, (1-6C)alkoxy-(2-6C)alkylamino, cyano-(1-6C)alkylamino, carboxy-(1-6C)alkylamino, (1-6C)alkoxycarbonyl-(1-6C)alkylamino, carbamoyl-(1-6C)alkylamino, N-(1-6C)alkylcarbamoyl-(1-6C)alkylamino, N,N-di-[(1-6C)alkyl]carbamoyl-(1-6C)alkylamino, amino-(2-6C)alkylamino, (1-6C)alkylamino-(2-6C)alkylamino, di-[(1-6C)alkyl]amino-(2-6C)alkylamino, N-(1-6C)alkyl-halogeno-(1-6C)alkylamino, N-(1-6C)alkyl-hydroxy-(2-6C)alkylamino, N-(1-6C)alkyl-(1-6C)alkoxy-(2-6C)alkylamino, N-(1-6C)alkyl-cyano-(1-6C)alkylamino, N-(1-6C)alkyl-carboxy-(1-6C)alkylamino, N-(1-6C)alkyl-(1-6C)alkoxycarbonyl-(1-6C)alkylamino, N-(1-6C)alkyl-carbamoyl-(1-6C)alkylamino, N-(1-6C)alkyl-N-(1-6C)alkylcarbamoyl-(1-6C)alkylamino, N-(1-6C)alkyl-N,N-di-[(1-6C)alkyl]carbamoyl-(1-6C)alkylamino, N-(1-6C)alkyl-amino-(2-6C)alkylamino, N-(1-6C)alkyl-(1-6C)alkylamino-(2-6C)alkylamino, N-(1-6C)alkyl-di-[(1-6C)alkyl]amino-(2-6C)alkylamino, halogeno-(2-6C)alkanoylamino, hydroxy-(2-6C)alkanoylamino, (1-6C)alkoxy-(2-6C)alkanoylamino, cyano-(2-6C)alkanoylamino, carboxy-(2-6C)alkanoylamino, (1-6C)alkoxycarbonyl-(2-6C)alkanoylamino, carbamoyl-(2-6C)alkanoylamino, N-(1-6C)alkylcarbamoyl-(2-6C)alkanoylamino, N,N-di-[(1-6C)alkyl]carbamoyl-(2-6C)alkanoylamino, amino-(2-6C)alkanoylamino, (1-6C)alkylamino-(2-6C)alkanoylamino, di-[(1-6C)alkyl]amino-(2-6C)alkanoylamino, aryl, aryl-(1-6C)alkyl, aryl-(1-6C)alkoxy, aryloxy, arylamino, N-(1-6C)alkyl-arylamino, aryl(1-6C)alkylamino, N-(1-6C)alkyl-aryl-(1-6C)alkylamino, aroylamino, arylsulphonylamino, N-arylsulphamoyl, aryl-(2-6C)alkanoylamino and (1-3C)alkylenedioxy, and wherein any of the substituents on Q defined hereinbefore which comprises a $CH_2$ group which is attached to 2 carbon atoms or a $CH_3$ group which is attached to a carbon atom may optionally bear on each said $CH_2$ or $CH_3$ group a substituent selected from hydroxy, amino, (1-6C)alkoxy, (1-6C)alkylamino and di-[(1-6C)alkyl]amino, and wherein any aryl group in a substituent on Q may optionally bear 1 or 2 substituents selected from hydroxy, halogeno, (1-6C)alkyl, (1-6C)alkoxy, carboxy, (1-6C)alkoxycarbonyl, N-(1-6C)alkylcarbamoyl, N,N-di-[(1-6C)alkyl]carbamoyl, (2-6C)alkanoyl, amino, (1-6C)alkylamino, di-[(1-6C)alkyl]amino, halogeno-(1-6C)alkyl, hydroxy-(1-6C)alkyl, (1-6C)alkoxy-(1-6C)alkyl, cyano-(1-6C)alkyl, amino(1-6C)alkyl, (1-6C)alkylamino-(1-6C)alkyl, di-[(1-6C)alkyl]amino-(1-6C)alkyl, aryl and aryl-(1-6C)alkyl;

or a pharmaceutically-acceptable salt or in-vivo-cleavable ester formed on an available carboxy group thereof.

3. An amide derivative of the Formula Ia according to claim 1 wherein X is —NHCO— or —CONH—;

$R^3$ is hydrogen, methyl or ethyl;

m is 1 or 2;

at least one $R^1$ is a piperazinyl group and any other $R^1$ group that is not a piperazinyl group is selected from hydroxy, fluoro, chloro, bromo, trifluoromethyl, cyano, methyl, ethyl, methoxy, ethoxy, amino, methylamino, ethylamino, dimethylamino, diethylamino, methylaminomethyl, ethylaminomethyl, dimethylaminomethyl, diethylaminomethyl, 2-aminoethoxy, 3-aminopropoxy, 2-methylaminoethoxy, 2-ethylaminoethoxy, 3-methylaminopropoxy, 3-ethylaminopropoxy, 2-dimethylaminoethoxy, 2-diethylaminoethoxy, 3-dimethylaminopropoxy, 3-diethylaminopropoxy, 2-aminoethylamino, 3-aminopropylamino, 2-methylaminoethylamino, 2-ethylaminoethylamino, 3-methylaminopropylamino, 3-ethylaminopropylamino, 2-dimethylaminoethylamino, 2-diethylaminoethylamino, 3-dimethylaminopropylamino, 3-diethylaminopropylamino N-(2-aminoethyl)-N-methylamino, N-(3-aminopropyl)-N- methylamino, N-(2-methylaminoethyl)-N-methylamino, N-(2-ethylaminoethyl)-N-methylamino, N-(3-methylaminopropyl)-N-methylamino, N-(3-ethylaminopropyl)-N-methylamino, N-(2-dimethylaminoethyl)-N-methylamino, N-(2-diethylaminoethyl)-N-methylamino, N-(3-dimethylaminopropyl)-N-methylamino, and N-(3-diethylaminopropyl)-N-methylamino;

n is 0 or 1;

$R^2$ is fluoro, chloro, bromo, methyl or ethyl;

q is 0; and

Q is furyl, thienyl, oxazolyl, isoxazolyl, imidazolyl, pyrazolyl, thiazolyl, isothiazolyl, pyridyl, pyridazinyl, pyrimidinyl, pyrazinyl, beuzofuranyl, indolyl, benzothienyl, benzoxazolyl, benzimidazolyl, benzothiazolyl, indazolyl, benzofurazanyl, quinolyl, isoquinolyl, quinazolinyl, quinoxalinyl, naphthyridinyl, carbazolyl, dibenzofuranyl, dibenzothiophenyl or xanthenyl which optionally bears 1 or 2 substituents selected from hydroxy, fluoro, chloro, trifluoromethyl, cyano, amino, methyl, ethyl, methoxy, ethoxy, propoxy, isopropoxy, cyclopentyloxy, methylenedioxy, methylamino, ethylamino, dimethylamino, diethylamino, acetamido, propionamido N-methylacetamido, methanesulphonamido N-methylmethanesulphonamido, aminomethyl, methylaminomethyl, ethylaminomethyl, dimethylaminomethyl, diethylaminomethyl, 2-hydroxyethoxy, 3-hydroxypropoxy, 2-methoxyethoxy, 2-ethoxyethoxy, 3-methoxypropoxy, 3-ethoxypropoxy, 2-aminoethoxy, 3-aminopropoxy, 2-methylaminoethoxy, 2-ethylaminoethoxy, 3-methylaminopropoxy, 3-ethylaminopropoxy, 2-dimethylaminoethoxy, 2-diethylaminoethoxy, 3-dimethylaminopropoxy, 3-diethylaminopropoxy and phenyl, and wherein any phenyl group in a substituent on Q may optionally bear 1 or 2 substituents selected from fluoro, chloro, methyl and methoxy;

or a pharmaceutically-acceptable salt thereof.

4. An amide derivative of the Formula Ib according to claim 2 wherein $R^3$ is hydrogen or methyl;

m is 1;

$R^1$ is 4-methylpiperazin-1-yl;

n is 0 or 1;

$R^2$ is 6-methyl;

q is 0; and

Q is dibenzofuran-4-yl;

or a pharmaceutically-acceptable salt thereof.

5. An amide derivative of the Formula Ib according to claim 2 wherein $R^3$ is hydrogen;

m is 1;

$R^1$ is piperazin-1-yl or 4-methylpiperazin-1-yl;

n is 0 or 1;

$R^2$ is 6-methyl or 6-fluoro;

q is 0; and

Q is dibenzofuran-4-yl, 5-(4-chlorophenyl)furan-2-yl or 4-(4-chlorophenyl)thien-2-yl;

or a pharmaceutically-acceptable salt thereof.

6. An amide derivative of the Formula Ia according to claim 1 selected from:

3-[5-dibenzofuran-4-ylcarbonylamino-2-methylphenyl]-6-(4methylpiperazin 1-yl)-3,4-dihydroquinazolin-4-one, and 3-[5-(2-chloropyrid-4-ylcarbonylamino)-2-methylphenyl]-6-(4-methylpiperazin-1-yl)-3,4-dihydroquinazolin-4-one, or a pharmaceutically-acceptable salt thereof.

7. A process for the preparation of an amide derivative of the Formula Ia or Ib, or a pharmaceutically-acceptable salt or in-vivo-cleavable ester formed on an available carboxy group thereof, according to claim 1 or claim 2 which comprises:-

(a) reacting an N-phenyl-2-aminobenzamide of the Formula II

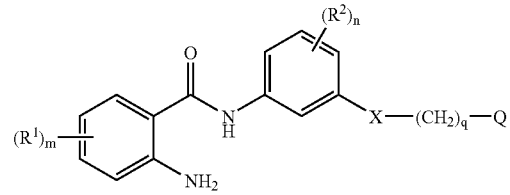

with a carboxylic acid of the Formula III, or a reactive derivative thereof,

wherein variable groups are as defined in claim 1 and wherein any functional group is protected if necessary, and:
(i) removing any protecting groups; and
(ii) optionally forming a pharmaceutically-acceptable salt or in-vivo-cleavable ester;

(b) reacting an aniline of the Formula X

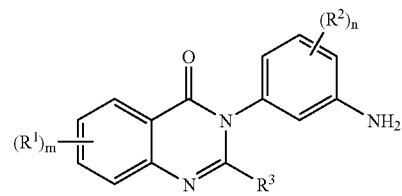

with a carboxylic acid of the Formula VI, or a reactive derivative thereof,

under standard amide bond forming conditions, wherein variable groups are as defined in claim 1 and wherein any functional group is protected if necessary, and:
(i) removing any protecting groups; and
(ii) optionally forming a pharmaceutically-acceptable salt or in-vivo-cleavable ester;

(c) for the preparation of an amide derivative of the Formula Ia wherein $R^1$ or a substituent on Q is (1-6C)alkoxy or substituted (1-6C)alkoxy, (1-6C)alkylthio, (1-6C)alkylamino, di-[(1-6C)alkyl]amino or substituted (1-6C)alkylamino, the alkylation, conveniently in the presence of a suitable base, of an amide derivative of the Formula Ia wherein $R^1$ or a substituent on Q is hydroxy, mercapto or amino as appropriate;

(d) for the preparation of an amide derivative of the Formula Ia wherein a substituent on Q is amino, (1-6C)alkylamino, di-[(1-6C)alkyl]amino, substituted (1-6C)alkylamino, substituted N-(1-6C)alkyl-(2-6C)

alkylamino or a N-linked heterocyclyl group, the reaction, conveniently in the presence of a suitable base, of an amide derivative of the Formula Ia wherein a substituent on Q is a suitable leaving group with an appropriate amine;

(e) for the preparation of an amide derivative of the Formula Ia wherein $R^1$ or a substituent on Q is (1-6C)alkanoylamino or substituted (2-6C)alkanoylamino, the acylation of a compound of the Formula Ia wherein $R^1$ or a substituent on Q is amino;

(f) for the preparation of an amide derivative of the Formula Ia wherein $R^1$ or a substituent on Q is (1-6C)alkanesulphonylamino, the reaction of a compound of the Formula Ia wherein $R^1$ or a substituent on Q is amino with a (1-6C)alkanesulphonic acid, or an activated derivative thereof;

(g) for the preparation of an amide derivative of the Formula Ia wherein $R^1$ or a substituent on Q is carboxy, carboxy-(1-6C)alkyl, carboxy-(1-6C)alkoxy, carboxy-(1-6C)alkylamino, N-(1-6C)alkyl-carboxy-(1-6C)alkylamino or carboxy-(2-6C)alkanoylamino, the cleavage of a compound of the Formula Ia wherein $R^1$ or a substituent on Q is (1-6C)alkoxycarbonyl, (1-6C)alkoxycarbonyl-(1-6C)alkyl, (1-6C)alkoxycarbonyl-(1-6C)alkoxy, (1-6C)alkoxycarbonyl-(1-6C)alkylamino, N-(1-6C)alkyl-(1-6C)alkoxycarbonyl-(1-6C)alkylamino or (1-6C)alkoxycarbonyl-(2-6C)alkanoylamino as appropriate; or (h) for the preparation of an amide derivative of the Formula Ia wherein $R^1$ is amino-(1-6C)alkyl, (1-6C)alkylamino-(1-6C)alkyl or di-[(1-6C)alkyl]amino-(1-6C)alkyl, the reaction, conveniently in the presence of a suitable base, of a compound of the Formula XIII

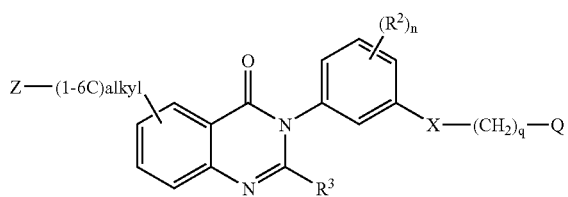

XIII wherein X, $R^2$, $R^3$, n, q and Q have any of the meanings defined in claim 1 and Z is a suitable leaving group with an appropriate amine or heterocycle.

8. A pharmaceutical composition which comprises an amide derivative of the Formula Ia or Ib, or a pharmaceutically-acceptable or in-vivo-cleavable ester formed on an available carboxy group thereof, as defined in any one of claims 1, 2 and 6, in association with a pharmaceutically-acceptable diluent or carrier.

9. A method of treating rheumatoid arthritis in a warm-blooded animal in need thereof, which comprises administering an effective amount of an amide derivative of the Formula Ia or Ib, or a pharmaceutically-acceptable salt or in-vivo-cleavable ester thereof, as defined any one of claims 1, 2 and 6.

10. A method of treating osteoarthritis in a warm-blooded animal in need thereof, which comprises administering an effective amount of an amide derivative of the Formula Ia or Ib, or a pharmaceutically-acceptable salt or in-vivo-cleavable ester thereof, as defined in any one of claims 1, 2 and 6.

11. A method of treating psoriasis in a warm-blooded animal in need thereof, which comprises administering an effective amount of an amide derivative of the Formula Ia or Ib, or a pharmaceutically-acceptable salt or in-vivo-cleavable ester thereof, as defined any one of claims 1, 2 and 6.

12. A method of treating chronic obstructive pulmonary disease in a warm-blooded animal in need thereof, which comprises administering an effective amount of an amide derivative of the Formula Ia or Ib, or a pharmaceutically-acceptable salt or in-vivo-cleavable ester thereof, as defined in any one of claims 1, 2 and 6.

* * * * *